US005624803A

United States Patent [19]
Noonberg et al.

[11] Patent Number: 5,624,803
[45] Date of Patent: Apr. 29, 1997

[54] IN VIVO OLIGONUCLEOTIDE GENERATOR, AND METHODS OF TESTING THE BINDING AFFINITY OF TRIPLEX FORMING OLIGONUCLEOTIDES DERIVED THEREFROM

[75] Inventors: Sarah B. Noonberg, Berkeley; C. Anthony Hunt, San Francisco, both of Calif.

[73] Assignee: The Regents of the University of California, Oakland, Calif.

[21] Appl. No.: 324,001

[22] Filed: Oct. 13, 1994

Related U.S. Application Data

[63] Continuation-in-part of Ser. No. 138,666, Oct. 14, 1993, abandoned.

[51] Int. Cl.$^6$ .............................. C12Q 1/68; C12N 15/63; C12N 15/11
[52] U.S. Cl. ............................ 435/6; 435/91.1; 435/320.1; 536/24.1
[58] Field of Search ..................... 435/6, 172.3, 320.1; 536/23.1, 24.1, 91.1

[56] References Cited

U.S. PATENT DOCUMENTS

| | | | |
|---|---|---|---|
| 5,190,931 | 3/1993 | Inouye | 435/91.32 |
| 5,272,065 | 12/1993 | Inouye et al. | 435/91.1 |
| 5,316,930 | 5/1994 | Loesch-Fries et al. | 435/172.3 |

FOREIGN PATENT DOCUMENTS

| | | |
|---|---|---|
| 0601585 | 6/1994 | European Pat. Off. . |
| 95/06744 | 3/1995 | WIPO . |
| 95/06718 | 3/1995 | WIPO . |

OTHER PUBLICATIONS

Case et al., "The unusual stability of the IS10 anti-sense RNA is critical for its function and is determined by the structure of its stem-domain" *EMBO J.* (1989) 8:4297–4305.
Chrisey et al., "Antisense technology: Principles and prospects for therapeutic development" *BioPharm* (1991) pp. 36–42.
Cooney et al., "Site-specific oligonucleotide binding represses transcription of the human c–myc gene in vitro" *Science* (1988) 241:456–459.
Das et al., "Upstream regulatory elements are necessary and sufficient for transcription of a U6 RNA gene by RNA polymerase III" *EMBO J.* (1988) 7:503–512.
Durland et al., "Binding of triple helix forming oligonucleotides to sites in gene promoters" *Biochem.* (1991) 30:9246–9255.
Duval-Valentin et al., "Specific inhibition of transcription by triple helix–forming oligonucleotides" *Proc. Natl. Acad. Sci. USA* (1992) 89:504–508.
Hannon et al., "Multiple cis–acting elements are required for RNA polymerase III transcription of the gene encoding H1 RNA, the RNA component of human RNase P" *J. Biol. Chem.* (1991) 266:22796–22799.

Hélène, "The anti-gene strategy: control of gene expression by triplex-forming-oligonucleotides" *Anti-Cancer Drug Design* (1991) 6:569–584.
Izant, "Chimeric antisense RNAs" *Gene Regulation: Biology of Antisense RNA and DNA* (1992) Erickson, R.P. et al., eds., Raven Press, New York, pp. 183–195.
Jennings et al., "Inhibition of SV40 replicon function by engineered antisense RNA transcribed by RNA polymerase III" *EMBO J.* (1987) 6:3043–3047.
Junker et al., "Reduction in replication of the human immunodeficiency virus type 1 in human cell lines by polymerase III–driven transcription of chimeric tRNA–antisense RNA genes" *Antisense Res. & Develop.* (1994) 4:165–172.
Kunkel et al., "U6 small nuclear RNA is transcribed by RNA polymerase III" *Proc. Natl. Acad. USA* (1986) 83:8575–8579.
Kunkel et al., "Transcription of a human U6 small nuclear RNA gene in vivo withstands deletion of intragenic sequences but not for an upstream TATATA box" *Nucleic Acids Res.* (1989) 17:7371–7379.
Marshallsay et al., "Characterization of the U3 and U6 snRNA genes from wheat: U3snRNA genes in monocot plants are transcribed by RNA polymerase III" *Plant Mol. Biol.* (1992) 19:973–983.
Moffat, "Making sense of antisense" *Science* (1991) 253:510–511.
Murphy et al., "The in vitro transcription of the 7SK RNA gene by RNA polymerase III is dependent only on the presence of an upstream promoter" *Cell* (1987) 51:81–87.
Noonberg et al., "Detection of triplex–forming RNA oligonucleotides by triplex blotting" *BioTechniques* (1994) 16:1070–1072.
Noonberg et al., "In vivo generation of highly abundant sequence-specific oligonucleotides for antisense and triplex gene regulation" *Nucleic Acids Res.* (1994) 22:2830–2836.
Sullenger et al., "Expression of chimeric tRNA–driven antisense transcripts renders NIH 3T3 cells highly resistant to Moloney murine leukemia virus replication" *Mol. & Cell. Biol.* (1990) 10:6512–6523.
Terns et al., "Multiple cis–acting signals for export of pre–U1 snRNA from the nucleus" *Genes & Development* (1993) 7:1898–1908.
Williard et al., "Paradoxical production of target protein using antisense RNA expression vectors" *Gene* (1994) 149:21–24.
Willis, "RNA polymerase III. Genes, factors and transcriptional specificity" *Eur. J. Biochem.* (1993) 212:1–11.
Yuan et al., "5' flanking sequences of human MRP/7–2 RNA gene are required and sufficient for the transcription by RNA polymerase III" *Biochim. Biophys. Acta* (1991) 1089:33–39.
Lyamichev et al, *Nucleic Acids Res.* 16: 2165 (1988).

*Primary Examiner*—James Martinell

[57] ABSTRACT

The present invention encompasses improved methods and materials for the delivering of antisense, triplex, and/or ribozyme oligonucleotides intracellularly, and RNA polymerase III-based constructs termed "oligonucleotide generators" to accomplish the delivery of oligonucleotides. Also encompassed by the present invention are methods for screening oligonucleotide sequences that are candidates for triplex formation.

28 Claims, 32 Drawing Sheets

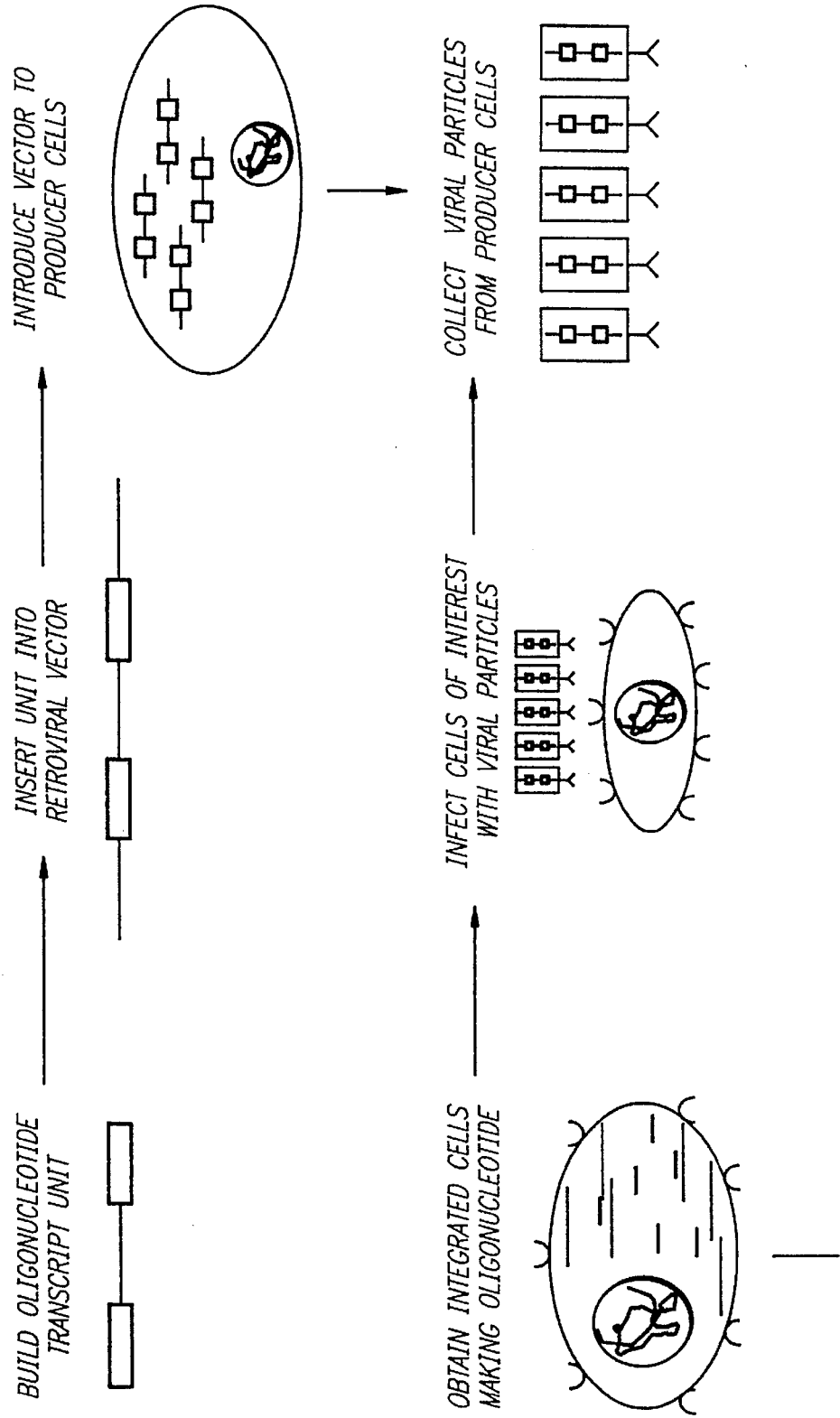

FIG. 3

HER2 PROMOTER FRAGMENT

-68                                                                              -19
3' TCCTCTTCCTCCTCCACCTCCTCCTCCCGACGAACTCCTCCTTCATATTCTTA
5' AGGAGAAGGAGGAGGTGGAGGAGGAGGGCTGCTTGAGGAAGTATAAGAAT

5' UCCUCUUCCUCCUCCCCCUCCUCUCCC    CU-RICH TRIPLEX FORMING RNA

3' AGGAGAAGGAGGAGGAGGGG          GA-RICH TRIPLEX FORMING RNA

THE U6 SMALL NUCLEAR RNA GENE

THE CHIMERIC OLIGONUCLEOTIDE PRODUCING GENE

THE U6ON OLIGONUCLEOTIDE

FIG. 9A

```
  u c
 u   g
  CG
  GC
 c UA
  CG
  GC
  UA20                           40              u
1 GCAUAUccu:CGaccuccccuucccuucccuucccCUUC:::C   c
    UAUAccuuGC::::::::::::::::::::::::GAAGuacG  c
                                              u a
  U
  U 80                                              60
  U        U6CTcon  ENERGY = -12.72 kcal
  U        (U60N    ENERGY = -12.46 kcal)
```

```
1                  20                              a g
 GuGcuCGCUUCg:GCAgCACAUau:::CCuCGaC:::AUG a   c
 C:CuuGCGAAGuaCGUaGUGUAagaacGG:GC:GgacUAC    a
                                          u u
 A              60                      40
 U
 A 80
 UUUUU
        U6AS  ENERGY = -30.83 kcal
        (mU6  ENERGY = -26.48 kcal)
```

FIG. 10

HER2 PROMOTER MAP AND
TRIPLEX RNA OLIGONUCLEOTIDE

TRIPLEX RNA OLIGONUCLEOTIDE

5' UCCUCUUCCUCCUCCCCUCCUCCUCCC 3'

-77                                                                                                           -20
5' CCCAATCACAGGAGAAGGAGGAGGAGGGCTGCTTGAGGAAGTATAAGAA 3'
3' GGGTTAGTGTCCTCTTCCTCCTCCACCTCCTCCCGACGAACTCCTTCATATTCTT 5'

CAAT                    ets-              TATA
BOX                   ELEMENT          BOX

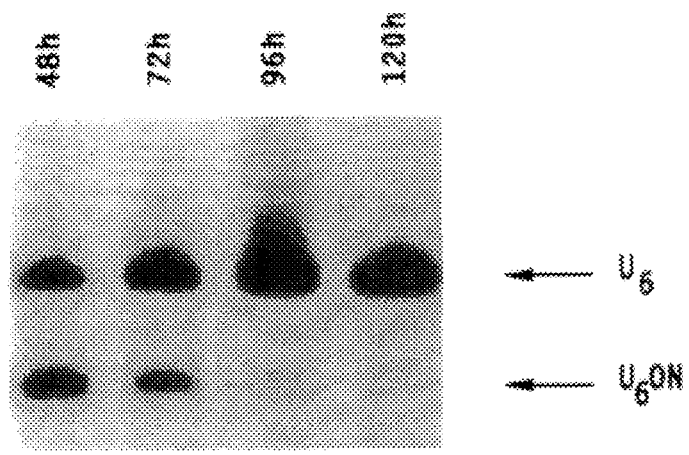
FIG. 12C
FIG. 14A
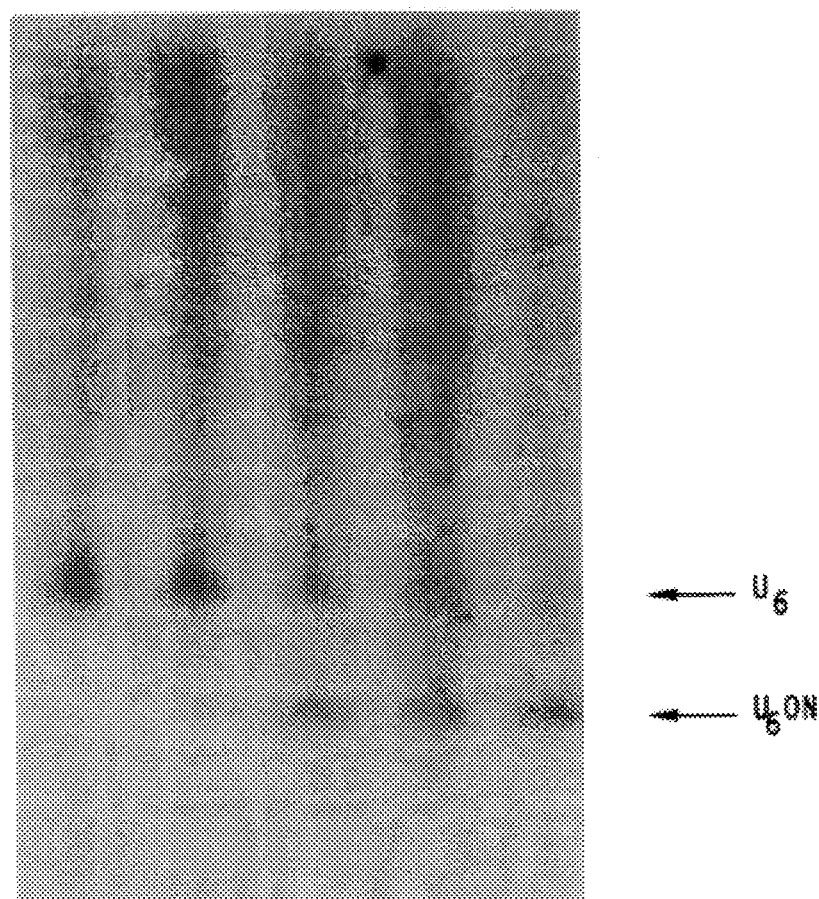

POSSIBLE FACTORS IN LIMITING SUPPLY:

RNA POLYMERASE III (RpolIII)
TFIIIB CONTAINING THE TATA BINDING PROTEIN (TBP)
PROXIMAL SEQUENCE ELEMENT BINDING PROTEIN (PBP)
UPSTREAM ENHANCERS (OctI,?)
OTHER UNCHARACTERIZED TRANSCRIPTIONAL FACTORS (?)
5′ CAPPING ENZYME, CO-FACTORS
LUPUS ASSOCIATED ANTIGEN (La)

FIG. 24

```
                    -76                                    -34
3'  GGTTAGTGTCTCTTCCTCTTCCACCTCCTCCTCCCGACGAAC
5'  CCAATCACAGGAGAAGGAGGAGGTGGAGGAGGAGGGCTTG

5'      UCCUCUUCCUCUCCCCUCCCUCCC...     CU-RICH RNA

3'      AGGAGAAGGAGGAGGGGAGGAGGAGGG...  GA-RICH RNA

5'      GGGCCCCCCCUCGAGGUCGACGGUAUCG... CONTROL RNA
```

FIG. 27A

U6 PARENT GENE

| | | | |
|---|---|---|---|
| -240 | TTCCCATGAT | TCCTTCATAT | TTGCATATAC |
| -210 | GATACAAGGC | TGTTAGAGAG | ATAATTAGAA |
| -180 | TTAATTTGAC | TGTAAACACA | AAGATATTAG |
| -150 | TACAAAATAC | GTGACGTAGA | AAGTAATAAT |
| -120 | TTCTTGGGTA | GTTTGCAGTT | TTTAAAATTA |
| -90 | TGTTTTAAAA | TGGACTATCA | TATGCTTACC |
| -60 | GTAACTTGAA | AGTATTTCGA | TTTCTTGGCT |
| -30 | TTATATATCT | TGTGGAAAGG | ACGAAACACC |
| +1 | GTGCTCGCTT | CGGCAGCACA | TATCCTCGAG |
| +31 | CATGGCCCCT | GCGCAAGGAT | GACACGCAAA |
| +61 | TGCATGAAGC | GTTCCATATT | TTT 83 NUCLEOTIDES |

FIG. 27B

U60N GENERATOR

| | | | |
|---|---|---|---|
| -240 | TTCCCATGAT | TCCTTCATAT | TTGCATATAC |
| -210 | GATACAAGGC | TGTTAGAGAG | ATAATTAGAA |
| -180 | TTAATTTGAC | TGTAAACACA | AAGATATTAG |
| -150 | TACAAAATAC | GTGACGTAGA | AAGTAATAAT |
| -120 | TTCTTGGGTA | GTTTGCAGTT | TTTAAAATTA |
| -90 | TGTTTTAAAA | TGGACTATCA | TATGCTTACC |
| -60 | GTAACTTGAA | AGTATTTCGA | TTTCTTGGCT |
| -30 | TTATATATCT | TGTGGAAAGG | ACGAAACACC |
| +1 | GTGCTCGCTT | CGGCAGCACA | TATCCTCGAC |
| +31 | TCCTCTTCCT | CCTCCACCTC | CTCCTCCCAT |
| +61 | GCATGAAGCG | TTCCATATTT | TT 82 NUCLEOTIDES |

IN VIVO OLIGONUCLEOTIDE GENERATOR, AND METHODS OF TESTING THE BINDING AFFINITY OF TRIPLEX FORMING OLIGONUCLEOTIDES DERIVED THEREFROM

CROSS-REFERENCE TO RELATED APPLICATION

This application is a continuation-in-part of U.S. application Ser. No. 08/138,666, filed Oct. 14, 1993, now abandoned. The disclosure of the above-referenced patent application is hereby incorporated in its entirety herein by reference.

TECHNICAL FIELD

This invention relates to gene regulation technologies, gene therapies, and methods of measuring triplex binding. Specifically the invention relates to the use of U6-type RNA polymerase III promoters in constructs that produce intracellular oligonucleotides, particularly antisense, triplex-binding, and/or ribozyme RNA transcripts, which are relatively free of disruptive RNA secondary structure in their binding domains. Specifically the invention also relates to a method for screening oligonucleotide sequences that are candidates for triplex formation with a double-stranded DNA target site.

BACKGROUND

There are three main strategies for using oligonucleotides to affect gene regulation. These strategies involve the use of antisense oligonucleotides, triplex (or antigene) oligonucleotides, and ribozymes. Each strategy has its inherent advantages and limitations, and each has a growing base of experimental successes.

Antisense Oligonucleotides

Antisense oligonucleotides are the earliest examples of oligonucleotide-based approaches to gene regulation. Not only were they the first to be tested for biological activity in the laboratory and the clinic, but also the antisense concept may have first arisen in prokaryotes. Naturally occurring antisense RNA has been detected in E. coli bacteria as well as in colE1 and IS10 plasmids. In these strains, regions of transcribed RNA in the antisense orientation serve to regulate the translation of RNA in the sense orientation (Inouye, M. (1988) Gene 72:25–34; and Simons, R. W. and Kleckner, N. (1988) Annual Rev. Gen. 22:567–600). Similar naturally occurring antisense regulation strategies have now been identified in several eukaryotic genes as well (Bentley, D. L. and Groudine, M. (1986) Nature 321:702–706; Kimelman, D. Gene regulation: Biology of Antisense RNA and DNA, R. P. Erickson, J. G. Izant, eds. (Raven Press, New York) pp. 1–10). Given that the normal messenger RNA (mRNA) transcribed from DNA is referred to as the "sense" RNA strand, oppositely oriented RNA are termed antisense RNA. Antisense oligonucleotides, then, refer to specific sequences of DNA or RNA which can bind in a Watson-Crick fashion to a sequence on a target mRNA.

In forming a double-stranded region on the mRNA, subsequent steps of protein synthesis may be interrupted by any of a variety of mechanisms. Interruption may occur by sterically blocking ribosome assembly or progression, sterically blocking intron/exon junctions and splice-sites needed for the processing of premature mRNA, or by invoking the cellular enzyme RNAse H that specifically cleaves mRNA in mRNA/DNA hybrids. The potential of antisense oligonucleotides to enact specific inhibition of protein synthesis is reflected in the tremendous number of publications which have appeared in the nearly 20 years since the earliest report of an antisense effect against the Rous Sarcoma Virus (Zamecnik, P. C. and Stephenson, M. L. (1978) Proc. Natl. Acad. Sci. USA 75:280–284; and for general reference on antisense oligonucleotides see: Moffat, A. S. (1991) Science 253:510–511; Chrisey, L. A. and Hawkins, J. W. (1991) Biopharm. 36–42; Oligonucleotides: Antisense Inhibitors of Gene Expression (1989) J. S. Cohen, ed. (MacMillan Press, London); and Stein, C. A. and Cheng, Y. C. (1993) Science 261:1004–1012). Antisense RNA and DNA has been demonstrated to lead as much as 95% inhibition of specific mRNA translation. In some cases, the antisense strategy has led to upregulated levels of the corresponding protein (Williard, R. L. et al. (1994) Gene (in press)).

A single gene encoded in DNA can, and most often will, be transcribed multiple times, giving rise to many copies of mRNA. In turn, a single mRNA molecule can, and most often will, be translated multiple times giving rise to many copies of the corresponding protein. Therefore, amplification can take place both at the DNA->mRNA level, and also at the mRNA->protein level. Antisense oligonucleotides can be very effective at blocking the translation of RNA and reducing the amount of protein synthesized, but they must be present within the cell in sufficient numbers to account for the previous DNA->mRNA amplification step. If a cell contains a compensatory response to lower levels of a given protein, feedback may upregulate the transcription of the corresponding RNA, increase mRNA stability, or signal for an increase in ribosomal assembly—all of which may serve to diminish the efficacy of an antisense approach. Given this constraint, it is unlikely that 100% inhibition of target gene expression could be achieved. To achieve this maximal level of inhibition, one must backstep and posit a strategy in which mRNA transcription (and thus the first level of amplification) is prevented. Such a strategy can be theoretically achieved by triple helix-forming (triplex) oligonucleotides.

Triplex Oligonucleotides

The development of triplex oligonucleotides as inhibitors of gene expression is receiving considerable, albeit delayed, attention. In 1957, Felsenfeld, Davies, and Rich described a surprisingly stable structure composed of three homopolymeric nucleic acid strands (Felsenfeld, G. et al. (1957) J. Am. Chem. Soc. 79:2023–2024). Two of these strands formed normal Watson-Crick hydrogen bonds, while the third strand was associated by what are now called Hoogsteen hydrogen bonds. Later studies confirmed and elaborated upon these findings, and determined that a pyrimidine-rich third strand could reside in the major groove of homopurine/homopyrimidine double-stranded DNA or RNA without perturbation of underlying Watson-Crick base-pairs. The binding was found to be pH-dependent (when cytosine residues were involved), and oriented parallel to the corresponding purine strand of the double-stranded helix (Lyamichev, V. I. et al. (1986) J. Biomol. Struct. and Dynam. 3:667–669; and Moser, H. E. and Dervan, P. B. (1987) Science 238:645–650). Nearly three decades passed before several laboratories began to use triplex oligonucleotides both to create a new class of sequence-specific DNA cleaving tools (Moser, H. E. and Dervan, P. B. (1987) Science 238:645–650; Strobel, S. A. and Dervan, P. B. (1990) Science 249:73–73; Strobel, S. A. and Dervan, P. B. (1991) Nature 350:172–174; and Dervan, P. B. Oligonucleotides: Antisense Inhibitors of Gene Expression, J. S. Cohen, ed. (Macmillan Press, London) pp. 197–210) as well as to mediate specific gene regulation at the level of the promoter (Durland, R. H. et al. (1991) Biochem. 30:9246–9255; Duval-Valentin, G. et al. (1992) Proc. Natl. Acad. Sci. USA 89:504–508; and Maher, L. J. et al. (1989) Science 245:725–730).

Subsequently, a number of reports emerged citing the ability of a sequence-specific pyrimidine-rich oligonucleotide to inhibit the binding of DNA binding proteins and in vitro gene transcription and elongation (Maher, L. J. et al. (1992) Biochem. 31:70–81; Young SL et al. (1991) Proc. Natl. Acad. Sci. USA 88:10023–10026; and Cooney, M. et al. (1988) Science 241:456–459). In addition to the pyrimidine-rich third strand binding motif previously described, a second triplex binding motif was identified involving a purine-rich third strand bound in a Mg++ dependent, pH-independent fashion (Chamberlin, M. J. and Patterson D. L. (1965) J. Mol. Biol. 12:410–428; Cooney, M. et al. (1988) Science 241:456–459; and Beal, P. A. and Dervan, P. B. (1991) Science 251:1360–1363). Orientation was shown to be antiparallel when the third strand was composed of G and A residues and dependent upon GpA steps in the target sequence when the third strand was composed of G and T residues (Sun, J. S. et al. (1991) C. R. Acad. Sci. Paris Serial III 313:585–590). A growing number of reports of in vivo inhibition of gene expression have been cited using triplex oligonucleotides of this second binding motif, while only triplex oligonucleotides conjugated to crosslinking agents have shown similar capabilities when using the first binding motif (Postel, E. H. et al. (1991) Proc. Natl. Acad. Sci. USA 88:8227–8231; McShan, W. M. et al. (1992) J. Biol. Chem. 267:5712–5721; Ing, N. H. et al. (1993) Nuc. Acids Res. 21:2789–2796; Roy, C. (1993) Nuc. Acids Res. 21:2845–2852); and Grigoriev, M. et al. (1993) Proc. Natl. Acad. Sci. USA 90:3501–3505).

While the majority of reports which cite triplex-based repression of transcription both in vitro and in vivo have utilized DNA triplex oligonucleotides on DNA double-stranded targets, recent research indicates that the thermodynamics of binding may favor an RNA third strand over a DNA third strand should a pyrimidine-rich binding motif be chosen (Roberts, R. W. and Crothers, D. M. (1992) Science 258:1463–1467; and Escude, C. et al. (1993) Nuc. Acids Res. 21:5547–5553). However, RNA purine-rich oligonucleotides have not been shown to form triplex structures with DNA double-stranded targets under any known conditions (Escude, C. et al. (1993) Nuc. Acids Res. 21:5547–5553; and Noonberg, S. B. et al. (1994) BioTechniques 16:1070–1073), but have been shown to form triplex structures with RNA homopurine/hompyrimidine duplexes and DNA/RNA hybrid duplexes (Chamberlin, M. J. and Patterson, D. L. (1965) J. Mol. Biol. 12:410–428). Such results underscore the importance of differing sugar backbones on triplex formation and stability.

A great deal of research effort and resources are being devoted to triplex oligonucleotides due to their potential to abolish completely the expression of a specific protein, especially when conjugated to intercalating agents which can crosslink the underlying DNA at a given triplex site (Grigoriev, M. et al. (1993) Proc. Natl. Acad. Sci. USA 90:3501–3505; and Helene, C. and Toulme, J. J. in Oligonucleotides: Antisense Inhibitors of Gene Expression, J. S. Cohen, ed. (Macmillan Press, London) pp. 137–172). Whether the triplex structure is permanent or in a binding equilibrium, triplex formation may inhibit the expression of a given gene in a variety of mechanisms: steric interference with transcription factor binding and assembly on promoter targets, alteration of duplex rigidity and inability for non-adjacent DNA binding proteins to associate, alteration of major and minor grooves to prevent neighboring transcription factor binding, and inhibition of elongation of the transcription complex producing truncated mRNA transcripts. In addition, a covalent complex may induce DNA repair elements to cleave out the linkage and thus inactivate a regulatory region of a gene.

Ribozymes

First identified within the RNA of Tetrahymenae (Kruger, K. (1982) Cell 31:147–157), ribozymes are able to perform self-cleavage reactions without additional protein enzyme or catalytic elements. This feature suggests that ribozymes may represent the first self-replicating entity. Ribozymes have now been isolated (primarily from viral sources) in various species of plants, fungi, and animals, all sharing the same capacity for catalytic activity without additional protein co-factors (Foster, A. C. and Symons, R. H. (1987) Cell 49:211–220). Their possible role in selective gene regulation stems from the ability to couple the catalytic RNA center domain to flanking RNA sequences designed to target an mRNA molecule by Watson-Crick base-pairing. Thus, the ribozyme can bind and cleave a target mRNA without self-impairment. Like antisense oligonucleotides, ribozymes also act on mRNA as opposed to DNA, and therefore do not affect the initial amplification step of transcription. And like antisense oligonucleotides, it may be near impossible to achieve 100% inhibition of target gene expression using a ribozyme strategy. However, unlike antisense oligonucleotides, ribozymes have the potential to quickly, permanently, and repetitively inactivate substrate mRNA. These differences may allow for the detection of significant biological activity at far lower concentrations intracellularly.

As with antisense and triplex oligonucleotides, a growing number of reports of ribozyme-mediated suppression of protein synthesis are appearing (Cotten, M. and Birnstiel, M. L.(1989) EMBO J. 8:3861–3868; Sarver, M. et al. (1990) Science 247:1222–1224; Cameron, F. H. and Jennings, P. A. (1989) Proc Natl Acad Sci USA 86:9139–9143; and Haseloff, J. and Gerlach, W. L. Nature 334: 585–591).

Increasing attention has been drawn to employing antisense, ribozyme, and triplex forming oligonucleotides in strategies for specific gene regulation. Oligonucleotides may specifically bind to viral DNA and RNA sequences involved in viral replication and pathogenicity, cellular oncogenic DNA and RNA sequences involved in neoplastic cell proliferation and differentiation, and various protein coding DNA and RNA sequences involved in disease pathophysiology. Oligonucleotides are thought to have potential utility in antiviral, anticancer, and antiprotein therapeutics.

Historically, oligonucleotides have been introduced into cells in one of three ways: by addition to the extracellular media, by invasive techniques such as electroporation or microinjection, or by integration of antisense mRNA vectors into the host chromosome. Each of these methods has its advantages and limitations. The first method, the addition of oligonucleotides to the media bathing the cells, induces little cellular damage and delivers short nucleic acid sequences, but the mechanisms of oligonucleotide uptake have poor efficiency and the cost of oligonucleotide synthesis is significant.

The second class of techniques, microinjection and electroporation, can greatly increase the efficiency of uptake of small oligonucleotides into the cell, but may cause significant cellular injury and disruption of normal cellular function. The third class of techniques, integration of the target gene and RNA polymerase II promotor in an antisense orientation via plasmids or retroviral vectors, can provide stable transcripts in healthy cells, but these transcripts retain their full length and can be expected to display considerable secondary structure, masking key antisense regions. In addition, RNA polymerase II transcripts are not continually produced, and transcriptional frequency is quite low in comparison to RNA products from polymerases I and III.

Interest in the biological activity of triplex-forming oligonucleotides has been steadily increasing, owing in part to their potential as artificial repressors of gene expression (Helene, C. (1991) Anticancer Drug Design 6:569–584; Maher III, L. J. et al. (1989) Science 245:725–730; Postel, E. H. et al. (1991) Proc. Natl. Acad. Sci. USA 88:8227–8231; and Ing, N. H. et al. (1993) Nucleic Acids Res. 21:2789–2796) as well as mediators of site-specific DNA cleavage (Moser, H. E. and Dervan, P. B. (1987) Science 238:645–650; and Strobel, S. A. and Dervan, P. B. (1991) Nature 350:172–174).

The potential of triplex and antisense oligonucleotides to inhibit selectively protein synthesis from a specified target gene has generated significant enthusiasm for their development as experimental therapeutics. Inhibition of expression of virally-derived proteins (Zamecnik & Stephenson (1978) Proc. Natl. Acad. Sci. USA 75: 280–284; Agrawal, S. (1991) In Prospects for Antisense Nucleic Acid Therapy of Cancer and AIDS. Eric Wickstrom, ed. (Wiley-Liss, New York), pp. 143–158; and McShan, W. M. et al. (1992) J. Biol. Chem. 267: 5712–5721) or endogenously activated oncogenes that contribute to cancer induction and/or progression (Helene, C. (1991) Anticancer Drug Design 6: 569–584; Postel, E. H. et al. (1991) Proc. Natl. Acad. Sci. USA 88: 8227–8231; and Calabretta, B. (1991) Cancer Research 51: 4505–4510) represent two particularly active areas of applied research, although the technology is also a powerful basic science research tool for the functional assessment of specific genes in cellular growth and differentiation (Simons, M. et al. (1992) Nature 359: 67–70).

While sufficient evidence indicates that oligonucleotides can cross the multiple cellular membrane barriers needed to reach their intracellular targets (Loke, S. L. et al. (1989) Proc. Natl. Acad. Sci. USA 86: 3474–3478; Yakubov, L. et al. (1989) Proc. Natl. Acad. Sci. USA 86: 6454–6458; Wu-Pong, S. et al. (1992) Pharmaceutical Research 9: 1010–1017; and Noonberg, S. B. et al. (1993) J. Invest. Dermatol. 101: 727–731), a growing number of reports suggest that this uptake process is highly inefficient and may exhibit cell-type specificity and heterogeneity (Noonberg, S. B. et al. (1993) J. Invest. Dermatol. 101: 727–731; Krieg, A. M. et al. (1991) Antisense Research and Development 1: 161–171; and Iverson, P. L. et al. (1992) Antisense Research and Development 2: 211–222). In addition, imaging studies demonstrate that the typical pattern of oligonucleotide uptake results in oligonucleotide compartmentalization within punctate vesicles believed to be of endosomal origin (Loke, S. L. et al. (1989) Proc. Natl. Acad. Sci. USA 86: 3474–3478; and Yakubov, L. et al. (1989) Proc. Natl. Acad. Sci. USA 86: 6454–6458), sequestered from their DNA or RNA targets, and subject to eventual lysosomal fusion and nuclease degradation. Rapid extracellular degradation has also been noted (Wickstrom, E. (1986) J. Biochem. Biophys. Meth. 13: 97–102). Biological activity is thought to arise from the small fraction of full-length oligonucleotide that either escapes from endosomes and rapidly accumulates in the nucleus, or enters the cytoplasm by another process and similarly accumulates intranuclearly. Oligonucleotide/ nucleic acid target interactions can thus occur en route to or within the nucleus.

Current strategies for the delivery of nucleic acid for antisense gene regulation fall into 1 of 2 major classes: direct extracellular addition of short DNA oligonucleotides (or analogues thereof) to cell culture media (as described in the previous chapter), or cellular gene transfection which is transcribed by RNA polymerase II into a long antisense transcript (or mRNA with antisense insert). Strategies for the delivery of nucleic acids for triplex gene regulation fall entirely into the first class, while strategies for the delivery of nucleic acid for ribozyme gene regulation fall entirely into the second class. Both classes have clear advantages, but both are also handicapped by limitations which have yet to be adequately circumvented (Table I).

TABLE I

Advantages and Limitations to Current Nucleic Acid Delivery Strategies

| | Advantages | Limitations |
|---|---|---|
| Oligodeoxyribonucleotides | Easy introduction to cells. | Uptake can be inefficient, heterogeneous. |
| | Minimal secondary structure concerns. | Rapid intra/extracellular degradation. |
| | No transfection required. | Possible toxicity. |
| | Accommodates chemical analogues. | Noncontinuous administration. |
| | Can be used for antisense or triplex strategies. | High cost of synthesis and purification. |
| Polymerase II transcripts | Intracellular expression. | Variable expression. |
| | Can be inducible. | Rapid intracellular degradation. |
| | Can be made permanent. | Long transcripts with variable start and stop positions. |
| | Inexpensive. | Considerable secondary structure can mask binding regions. |

Perhaps the biggest advantage of extracellular addition of oligonucleotides translates into the biggest disadvantage of intracellular generation of polymerase II transcripts— namely the length of the nucleic acid delivered. Oligonucleotides are, by their very name, short fragments of nucleic acid, and are thus generally capable of weak or predictable secondary and/or intermolecular structures. As such, their binding regions are expected to display increased accessibility to an intracellular nucleic acid target (whose accessibility may be difficult to predict). In contrast, polymerase II transcripts are generally very long (>1 kilobase) with highly variable trailing 3' sequences. These long and variable transcripts inevitably lead to complex secondary and tertiary structures which may mask key binding sequences. In most cases, a structural prediction of these long transcripts cannot be accurately determined.

Analogously, perhaps the biggest advantage of intracellular generation of polymerase II transcripts translates into the biggest disadvantage of extracellular addition of oligonucleotides—namely the site of nucleic acid delivery. Polymerase II transcripts are, by their very nature, generated intracellularly and thus do not need to cross the cell membrane barrier. For nuclear targets, the transcript is already in the correct subcellular compartment, while for cytoplasmic targets, the transcript must be actively or passively transported across the nuclear membrane. In contrast, extracellularly-added oligonucleotides must first cross the cell membrane, a process which has been shown to be inefficient, heterogeneous, cell-type specific, and to often lead to endosomal sequestration and subsequent lysosomal degradation. In addition, nucleic acid from both strategies are also susceptible to rapid degradation by cellular endonucleases and exonucleases, and both strategies may give rise to low or variable intracellular nucleic acid concentrations.

A logical question then becomes, can one design a system which combines the major advantages of both strategies while eliminating the major disadvantages? In positing such a system, one can put forth the following design criteria:

1. The system must be capable of delivering short nucleic acids of a pre-specified sequence and length to allow for adequate secondary structure prediction.

2. The system must be capable of delivering nucleic acid intracellularly.

3. The system must be capable of delivering nucleic acids of sufficient intracellular stability against nuclease degradation.

4. The system must be capable of delivering nucleic acids in high yield without cell-type specificity.

SUMMARY OF THE INVENTION

We have developed a system, here termed an "oligonucleotide generator", or an "in vivo oligonucleotide generator" for intracellular generation of short sequence-specific oligonucleotides in extremely high yield for the purposes of gene regulation. The invention provides for a continuous and abundant supply of short genetic fragments for use in any of a variety of gene regulation strategies.

According to the oligonucleotide generator invention, RNA polymerase III based promoter and terminator genetic sequences are used with one or more antisense, ribozyme, or triplex forming oligonucleotides as the coding regions. The constructs in some embodiments of the invention are provided with self-complementary ends to enhance stability.

We have developed a method, here termed "triplex blotting", for detection of triplex-forming RNA using radiolabeled double-stranded DNA probes within a background of total cellular RNA. Triplex blotting provides for detection of single cellular or in vitro generated RNA species, electrophoretically separated and immobilized on filters with radiolabeled triplex-forming double-stranded DNA probes.

The triplex blotting invention provides for comparison of relative binding affinities of various triplex-forming RNAs, for screening potential RNA sequences for triplex formation with double-stranded DNA targets, and for confirming the specificity of triplex formation of a DNA target probe within total cellular RNA. The benefits of triplex blotting include: sensitive and specific detection of homopurine/homopyrimidine RNA sequences; rapid screening of duplex DNA target sequences against triplex forming RNAs, with direct comparison of relative binding affinities; and confirmation of specificity of triplex formation amidst a background of total cellular RNA.

The present invention encompasses, constructs for generating a specific oligonucleotide within a cell, which construct comprises a nucleotide sequence from which the transcript is the specific oligonucleotide, said nucleotide sequence being flanked in the 5' direction by a stabilizing region and in the 3' direction by a termination sequence, and a promoter, which initiates transcription by RNA polymerase III, and which promoter is in the 5' direction from the stabilizing region.

The present invention further encompasses oligonucleotide generators, comprising from 5' to 3': (a) a U6-type RNA polymerase III promoter; (b) a specific nucleotide sequence from which a specific oligonucleotide can be transcribed; and (c) a termination sequence; wherein the components of the oligonucleotide generator are operably linked; and wherein the oligonucleotide generator is capable of being transcribed by RNA polymerass III to produce a transcript comprising the specific oligonucleotide.

The present invention encompasses methods for generating oligonucleotides intracellularly, comprising administering an oligonucleotide generator of the invention, in a form that permits entry of the oligonucleotides into a target cell.

The present invention encompasses generator vectors, comprising from 5' to 3': (a) a U6-type promoter; (b) a stabilizing region from which a hairpin-forming sequence can be transcribed; and (c) a termination sequence; wherein the components of the generator vector are operably linked.

The present invention encompasses methods of measuring triplex formation, which method comprises: (a) attaching a single-stranded nucleic acid to a solid support; (b) contacting the solid support with a fluid comprising a labeled double-stranded probe; (c) separating the unbound probe from the solid support; and (d) quantifying the amount of labeled double-stranded probe bound to the solid support.

The present invention encompasses methods of measuring triplex blotting, which method comprises: (a) attaching a double-stranded nucleic acid to a solid support; (b) contacting the solid support with a fluid comprising a labeled single-stranded probe; (c) separating the unbound probe from the solid support; and (d) quantifying the amount of labeled single-stranded probe bound to the solid support.

BRIEF DESCRIPTION OF THE DRAWINGS

FIG. 3 (SEQ ID NO:10 through SEQ ID NO:13) is a diagram showing a double-stranded DNA probe and triplex forming RNAs. The 50 base-pair double-stranded probe corresponds to bases −68 to −19 on the HER2/c-erb B2/neu proto-oncogene. The region in bold refers to the homopurine/homopyrimidine tract involved in triplex formation. The CU-rich and GA-rich RNA sequences correspond to pyrimidine (parallel) or purine (antiparallel) third strand triplex binding motifs, respectively.

FIG. 4 is a second diagram presenting an overview of the oligonucleotide generator system according to the invention. The structure of the U6 snRNA gene, the chimeric U6ON gene and the resulting U6ON transcript are shown.

FIG. 10 (SEQ ID NO:16 through SEQ ID NO:18) is a diagram of the HER2 proto-oncogene promoter map with a triplex RNA oligonucleotide.

FIG. 11 is a graph representing the effects of the U6ON and U6CTcon oligonucleotide generators on CAT activity in cells expressing CAT from an HER2 promoter.

FIG. 12 is two graphs and two half-tone reproductions of Northern blots, which demonstrate the effect of the U6ON generator on endogenous HER2 mRNA and cell growth in MDA 453 cells. FIG. 12C demonstrates the temporal pattern of U6ON expression after transient transfection.

FIG. 18 is a series of three graphs, illustrating the results of dynamic simulation of U6 and U6ON expression in 293. The dynamic modelling program Stella was used to solve the differential equations described in the Examples section. Data was then output to Cricket Graph software and graphically displayed

FIG. 24 (SEQ ID NO:19 through SEQ ID NO:23) is a diagram illustrating a double-stranded DNA probe and triplex forming RNAs. The 43-bp double-stranded DNA probe corresponds to bases −76 to −34 on the HER2/c-erb B2/neu proto-oncogene promoter. The region in bold refers to the homopurine/homopyrimidine tract involved in triplex formation. The CU-rich RNA sequence corresponds to the pyrimidine-rich (parallel) third strand triplex binding motif.

FIG. 26 is a set of two half-tone reproductions of autoradiograms, demonstrating triplex blotting versus Northern blotting with SKBR3 total cellular RNA. Cells were transfected with either 0 μg, 10 μg or 20 μg of the modified U6 plasmid which generates an 82 nucleotide triplex-forming CU-rich RNA oligonucleotide (lanes 2 and 3) or 20 μg of promoterless plasmid DNA (lane 1).

FIG. 27 (SEQ ID NO:24 and SEQ ID NO:25) is a set of two diagrams displaying (FIG. 27A) the sequence of the mU6 parent vector from which oligonucleotide-producing genes are made, and (FIG. 27B) the sequence of the U6ON generator.

DETAILED DESCRIPTION OF THE INVENTION

Figure 1B:
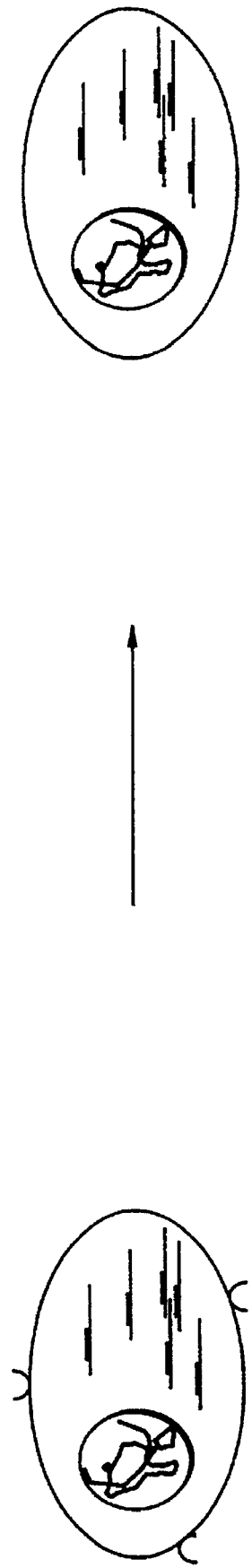
FIG. 1 is a diagram presenting an overview of the oligonucleotide generator system according to the invention, and provides an example of its use.
Figure 1B:
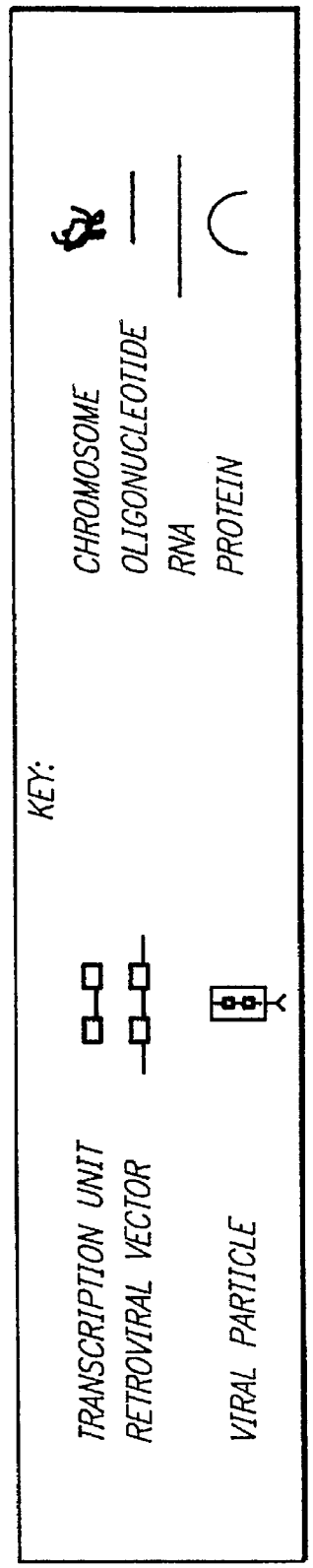

An improved method for delivery of oligonucleotides, preferably antisense or triplex oligonucleotides, was developed in order to circumvent the obstacles of extracellular degradation, cellular uptake, and intracellular sequestration. This new method is sufficiently general to provide for ribozyme delivery as well. The strategy was designed with the following criteria in mind: (a) oligonucleotides should be generated in high yield within the cell nucleus without significant cell type specificity; (b) they should be sufficiently stable; (c) they should contain minimal secondary structure that could mask binding regions; and (d) they should be of a pre-determined and well-defined sequence and length.

These criteria were satisfied by constructing one of the preferred embodiments of the oligonucleotide generator invention, containing regulatory regions from the human U6 small nuclear RNA (snRNA) gene and a synthetic double-stranded insert bearing the oligonucleotide to be generated. U6 snRNA, which normally functions in conjunction with several small nuclear riboproteins (snRNPs) in the splicing of premature messenger RNA (Manniatis & Reed (1987) Nature 325: 673–678), is transcribed in high yield by RNA polymerase III, requires only upstream promoter sequences for initiation, and terminates cleanly upon reaching a string of 4–6 thymine residues (Kunkel, G. et al. (1986) Proc. Natl. Acad. Sci. USA 83: 8575–8579; Reddy, R. et al. (1987) J. Biol. Chem. 262: 75–81; Kunkel & Pederson (1989) Nucleic Acids Res. 17: 7371–7379; and Willis, I. M. (1993) European J. of Biochem. 212: 1–11.) Transcript stability is strongly enhanced by 5' γ-monomethyl phosphate capping (Singh & Reddy (1989) Proc. Natl. Acad. Sci. USA 86: 8280–8283; and Singh, R. et al. (1990) Mol. Cell Biol. 10: 939–946) which is directed by a 5' self-complementary hairpin followed by a conserved hexameric AUAUAC sequence (Shumyatsky, G. et al. (1993) Nucleic Acids Res.

21: 4756–4761). Within this description of the present invention the abundant production, intranuclear localization, kinetics of expression, capping, and insert-specific stability of transcripts generated from an oligonucleotide generator of the invention were characterized.

In a general aspect, the oligonucleotide generators of the invention encompass a construct for producing a specific oligonucleotide within a cell, which construct comprises (a) an U6-type RNA polymerase III promoter; (b) a specific nucleotide sequence from which the specific oligonucleotide is transcribed; and (c) a termination sequence; wherein the components of the construct are operably linked and positioned from 5' to 3' in the order of (a), (b), and (c).

The terms "U6-type RNA polymerase III promoter" and "U6-type promoter" are used interchangeably herein to refer to a promoter which is able to initiate transcription by RNA polymerase III from a position upstream of the transcribed DNA. "U6-type promoters" have been referred to in the literature, in at least one instance, as RNA polymerase III, type III promoters (Willis, I. (1993) FEBS 212: 1–11). The "U6-type promoter" contains regulatory elements which are necessary and sufficient to facilitate transcription by RNA polymerase III, but these regulatory elements are not themselves transcribed. Thus, U6-type RNA polymerase III promoters include the following promoters: naturally-occurring U6 from higher order eukaryotes (Das et al. (1988) EMBO J. 7(2): 503–512), 7SK (Murphy et al. Cell 51:81–87), H1 RNA gene (Hannon, G. et al. (1991) J. Biol. Chem. 266(34): 22796–22799), U3 snRNA genes in plants (Marshallsay C. et al. (1992) Plant Molecular Biology 19(6): 973–983), and MRP gene (Yuan, Y. and Reddy, R. Biochem. et Biophys. Acta 1089(1): 33–39), as well as any recombinant promoter sequence which is able to initiate transcription by RNA polymerase III without itself being transcribed. Preferably, naturally-occurring U6 promoter is used as the U6-type RNA polymerase III promoter.

Figure 4A:
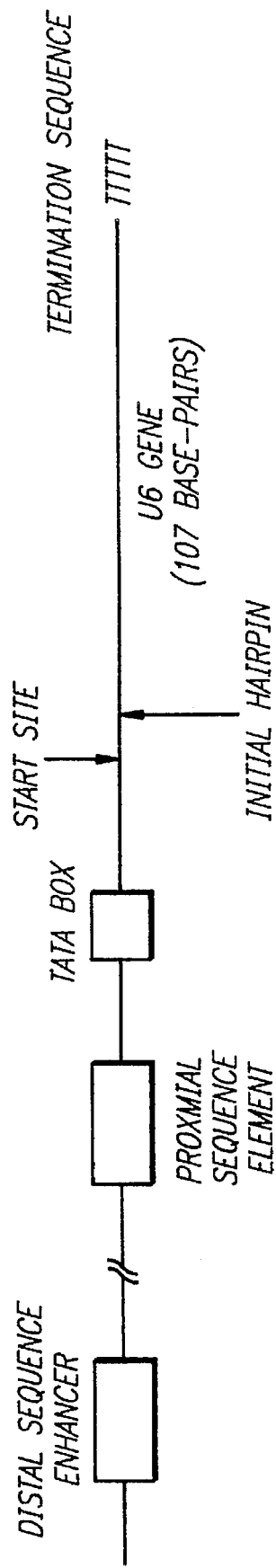
FIG. 4A. shows the U6 gene has three critical promoter elements necessary for efficient transcription, a 5' self-complementary hairpin sequence sufficient for capping, and a string of 5 thymidine residues necessary for termination.
Figure 4B:
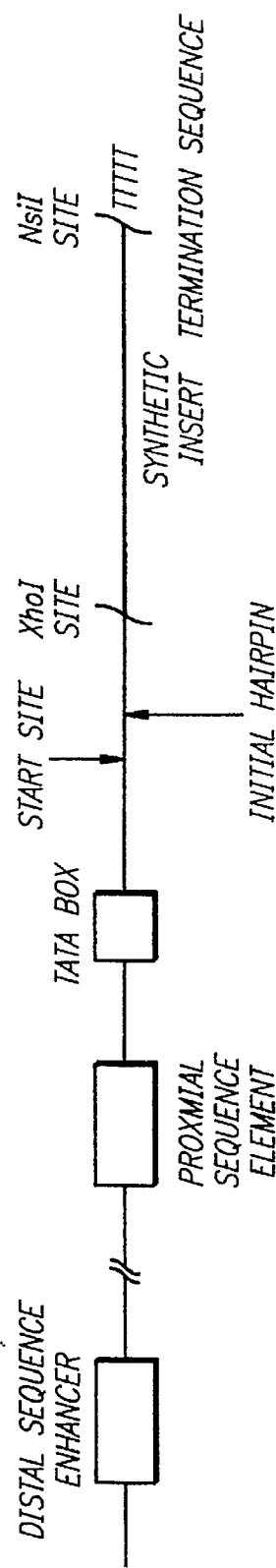
FIG. 4B demonstrates the elements which were retained in the construction of the chimeric gene, while its internal sequence was mutated to produce two unique restriction sites for inserting oligonucleotide sequences (bold line).

Recombinant U6-type promoters for use in the oligonucleotide generators of the invention will usually have the distal sequence enhancer, proximal sequence element and TATA box as displayed in FIG. 4B. The proximal sequence element and TATA box are required for Polymerase III transcription, and the relative position of these elements to each other and the start site are relatively inflexible. The distal sequence enhancer, however, can be deleted in part or completely, as well as moved closer to or farther away from the proximal sequence element, particularly if a reduction in the level of transcription is desired.

The oligonucleotide generators of the present invention can be used to facilitate delivery of oligonucleotides to any type of eukaryotic cell. The choice of a specific U6-type promoter is made on the basis of the target cell (cell to be transfected with the generator). U6-type promoters derived from a species that is closely related or at least has a similar promoter sequence to that of the target cell type are preferably used if maximal transcription of the specific oligonucleotide is desired. For example, human U6 promoters, when integrated into an oligonucleotide generator of the invention, would provide higher levels of transcription in human cells, but would be less effective in plant cells. Conversely, a plant U6 promoter would provide higher levels of oligonucleotide production in a plant than a mammalian system.

In a general aspect, the invention also features a construct for generating a specific oligonucleotide within a cell, which construct includes a nucleotide sequence from which the transcript is the specific oligonucleotide, flanked on the 5' end by a stabilizing region and on the 3' end by a termination sequence, and a promoter at the 5' end of the stabilizing region.

In preferred embodiments, the promoter and the stabilizing region are derived from a RNA polymerase III gene, and in particular embodiments it is derived from a human U6 small nuclear RNA gene. In particularly preferred embodiments the stabilizing region comprises the first approximately 25 nucleotides of the human U6 small nuclear RNA gene, as this includes a portion that forms a stable hairpin in the product and makes a "cap" that prevents degradation of the product at the 5' end. Alternatively, any hairpin-forming sequence can be used, and needn't be derived from a native source.

Generally, the optional "stabilizing region" of the oligonucleotide generator can be of any length, so long as the resulting RNA transcript of the oligonucleotide generator is predicted to form a hairpin structure by a computer program that models and predicts secondary structure of RNA. These computer programs include, for example, the algorithm described in Example 8. While longer stabilizing regions can be used, they are generally between about 16 and about 50 nucleotides in length. Most preferably the segments of the stabilizing region that are predicted to form base pairs in the resulting RNA transcript are continuous and perfectly complimentary, containing no mismatches. However, such mismatches are tolerated within the segments of the stabilizing region that are predicted to form base pairs, so long as they do not completely disrupt the hairpin structure as predicted by the computer modeling program. Usually the mismatched bases are less than about 1 in 5 of the nucleotides in the complimentary regions of the predicted hairpin structure, and almost always less than about 1 in 4.

A "stabilizing region" when present is preferably able to reduce the rate of intracellular degradation for the resulting RNA transcript as compared with an identical RNA transcript that does not contain the region transcribed from the stabilizing region. Methods of measuring the intracellular degradation rates of RNA are known in the art, and include the methods described in Example 11.

As described above there is a portion of the 5' end of the U6 gene that "makes a 'cap' that prevents degradation of the product at the 5' end", and is included in some preferred embodiments of the oligonucleotide generators of the invention. The stability of the resulting RNA transcripts is strongly enhanced by this 5' γ-monomethyl phosphate capping, which is directed by a 5' self-complementary hairpin followed by a conserved hexameric AUAUAC or AUAUCC sequence, preferably AUAUAC sequence, in the RNA transcript. Thus, when present in a oligonucleotide generator or generator vector of the invention the sequence on the coding strand for the capping segment is ATATCC or ATATAC. This optional "capping segment" in the oligonucleotide generators of the invention is usually only operable when it is immediately downstream of the hairpin structure of a stabilizing region, although the first two nucleotides of the capping segment may form part of the hairpin structure. When the "capping segment" is present, the hairpin structure of the stabilizing region is preferably about 20 to about 30 nucleotides in length, more preferably about 20 nucleotides in length, most preferably the hairpin structure from the 5' end of the U6 transcript.

The "specific oligonucleotide" may be any oligonucleotide that is desired to be transcribed within the cell and includes, for example, a triplex-forming oligonucleotide, an antisense oligonucleotide, a ribozyme, or a combination of these. Thus, the oligonucleotide generators of the present invention can be used to deliver RNA oligonucleotides for any purpose. For example, the oligonucleotide generators of the invention may be used to deliver tumor suppressing RNAs (Rastinejad, F. et al. (1993) Cell 75: 1107–1117; and Wickens, M. and Takayama, K. (1994) Nature 367: 17–18). Particularly favorable results are obtained using the construct of the invention for intracellular production of oligonucleotides in the size range between about 10 and about 60 nucleotides (and more particularly in the range between about 20 and 50 nucleotides), although the success of the invention is not strictly dependent upon the length of the oligonucleotide product. Oligonucleotide products are usually less than about 500 nucleotides in length.

In preferred embodiments, the termination region includes, in addition to a termination sequence (e.g., TTTT), a sequence between the termination sequence and the 3' end of the oligonucleotide sequence, to provide a 3' tail on the product; this aids in protecting the product from degradation at the 3' end; and the tail may be constructed to form a hairpin or other protective structure. Thus, the termination region includes at a minimum a transcription termination sequence recognized by RNA polymerase III, i.e. a stretch of four to six thymine nucleotides on the coding strand of the oligonucleotide generator.

The optional region of the oligonucleotide generator that provides the "3' tail" on the RNA transcript may be designed such that it forms a hairpin of any size, generally between about 16 and about 50 nucleotides in length. Also this region may be designed to form a lariat structure by base pairing with the nucleotides transcribed from a stabilizing region or a region of the transcript that is upstream of the specific oligonucleotide. Preferably, when a lariat forming 3' tail is used, the oligonucleotide generator also provides for the transcription of a hairpin structure in the 5' stabilizing region immediately followed by a capping segment. Thus, some of the RNA transcript may be capped with 5' γ-monomethyl phosphate prior to the formation of the more thermodynamically stable lariat structure.

The oligonucleotide generators of the invention can optionally be designed such that it produces a transcript with a predicted lariat conformation, wherein the stem of the lariat formed by the Watson-Crick base pairing of a 3' tail in the termination region and a portion of the transcript which is upstream of the specific oligonucleotide. The stem of the lariat structure may be of any length as long as a stable lariat structure is predicted by a computer program that models and predicts secondary structure of RNA. These computer programs include, for example, the algorithm described in Example 9. While longer stem regions can be used, the lariat stem is generally between about 8 and about 30 nucleotides in length. Most preferably, the stem of the lariat is predicted to form continuous base pairs for the stems entire length, containing no mismatches. However, such mismatches are tolerated within the segments of the lariat stem that are predicted to form base pairs, so long as they do not completely disrupt the lariat structure as predicted by the computer modeling program. Usually the mismatched bases are less than about 1 in 5 of the nucleotides in the lariat stem, and almost always less than about 1 in 4 of the nucleotides in the lariat stem.

Thus, the present invention encompasses oligonucleotide generators, comprising from 5' to 3': (a) an U6-type RNA polymerase III promoter; (b) a specific nucleotide sequence from which a specific oligonucleotide can be transcribed; and (c) a termination sequence; wherein the components of the oligonucleotide generator are operably linked; and wherein the oligonucleotide generator is capable of being transcribed by RNA polymerase III to produce a transcript comprising the specific oligonucleotide; and further comprising: a 5' tail from which a first lariat-forming sequence can be transcribed; and a 3' tail from which a second lariat-forming sequence can be transcribed; wherein the 5' tail is operably linked and positioned between the U6-type RNA polymerase III promoter and the specific nucleotide sequence; wherein the 3' tail is operably linked and positioned between the specific nucleotide sequence and the termination sequence; wherein the oligonucleotide generator is capable of being transcribed by RNA polymerase III to produce a transcript comprising from 5' to 3' the first lariat-forming sequence, the specific oligonucleotide, and the second lariat-forming sequence; and wherein the transcript is predicted to from a stable lariat structure by Watson-Crick base pairing between the nucleotides of the first lariat-forming region and the second lariat-forming region.

In particularly preferred embodiments, the stabilizing and termination portions of the construct are derived from the same source, and the construct is made by providing a vector containing, in sequence but not necessarily contiguous sequence, a promoter of the U6-type, a stabilizing 5' portion of the source gene (which may preferably be a part of a type III gene such as the first ~25 nucleotides of the human U6 gene), a XhoI site, a NsiI site, and a 3' portion of the source gene including at least a termination sequence (which may preferably be a part of the same type III gene such as a ~20 nucleotide 3' portion of the human U6 gene). Of course, the XhoI and NsiI restriction sites can be replaced with any first and second unique restriction enzyme sites to facilitate insertion of the specific nucleotide sequence.

Thus, in another general aspect, the present invention encompasses vectors which comprise any of the oligonucleotide generators described herein with the specific nucleotide sequence removed. These "generator vectors" may be used to construct an oligonucleotide generator of the invention. Preferably these generator vectors comprise two unique restriction enzyme sites, one on each side of the position of the generator vector into which the specific nucleotide sequence must be inserted to form an oligonucleotide generator of the invention. These unique restriction enzyme sites, when present, serve to facilitate insertion of the specific nucleotide sequence into the generator vector. More preferably the two restriction enzyme sites are not recognized by the same enzyme.

The U6 gene was chosen to provide the regulatory components for some of the preferred embodiments of the invention, as it is transcribed in nearly all mammalian cells in high yield; is transcribed constitutively; requires only upstream promoter sequences for transcription; and initiates and terminates cleanly and precisely (Kunkel, G. et al. (1986) Proc. Natl. Acad. Sci. USA 83: 8575–8579; Reddy, R. et al. (1987) J. Biol. Chem. 262: 75–81; Kunkel & Pederson (1989) Nucleic Acids Res. 17: 7371–7379; and Willis, I. M. (1993) European J. of Biochem. 212: 1–11.) In addition, the U6 gene contains a sequence-specific signal that directs the 5' capping of transcripts by a γ-monomethyl phosphate which greatly augments transcript stability (Singh & Reddy (1989) Proc. Natl. Acad. Sci. USA 86: 8280–8283; Singh, R. et al. (1990) Mol. Cell Biol. 10: 939–946; and Shumyatsky, G. et al. (1993) Nucleic Acids Res. 21: 756–4761). The output of this gene results in the abundant intracellular production of short, sequence-specific RNA oligonucleotides containing a 5' nuclease-resistant γ-monomethyl phosphate cap.

In another general aspect, the invention features a method for intracellularly generating an oligonucleotide of interest in a subject or in cells or tissues derived from a subject, including administering to the subject the construct according to the invention in a form that permits entry of the construct into the subject's cells. The administration may be carried out by any of various techniques known, for example, in the art of gene therapy (see, for example, J. W. Larrick and Kathy L. Burck, Gene Therapy, Application of Molecular Biology, Elsevier, Holland, 1991); or by administration in immunoliposomes, according to techniques known in the immunotherapeutic art, wherein the immunoliposome may be targeted to, and its contents delivered into, a particular cell type (such as, for example, a breast cancer cell); or by localized injection at a site for treatment; or by way of mucosally-lined passages; or via the airways, for example; all depending upon the particular treatment.

Advantages of the oligonucleotide generator of the invention include high yield and continuous production of oligonucleotides within the cell, and minimal secondary structure within binding regions on the oligonucleotide products, except where the secondary structure is an important functional part of a ribozyme contained in the specific oligonucleotide.

Viral integration into the chromosome of the cell can, according to the invention, confer permanence to the oligonucleotide-based antiviral, anticancer, or antiprotein gene regulation.

Figure 2A:
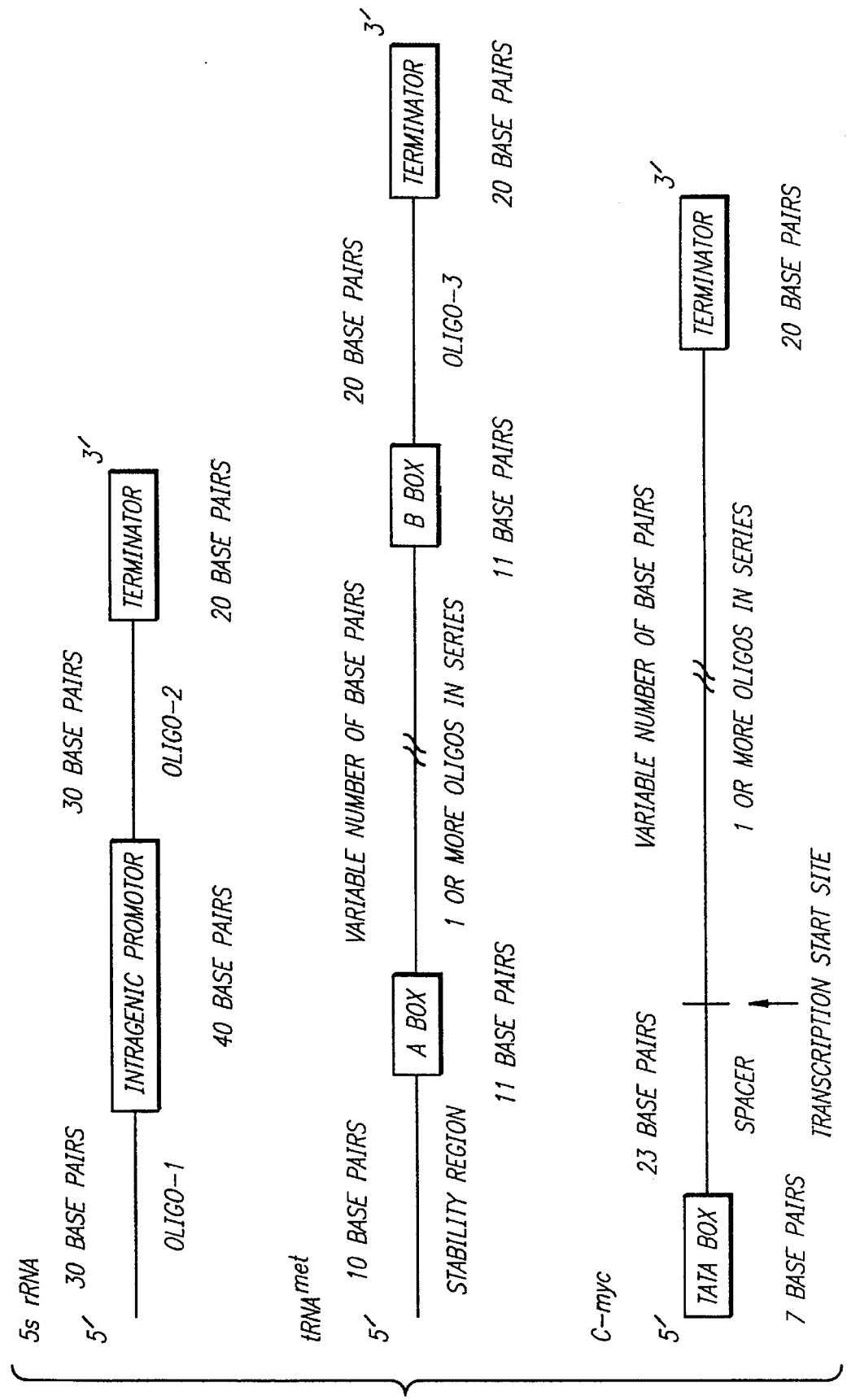
FIG. 2 is a diagram illustrating in further detail the invention shown in overview in FIG. 1, demonstrating exemplary transcript configurations and promoter and terminator sequences (SEQ ID NO:8 and SEQ ID NO:9) according to the invention.
Figure 2B:
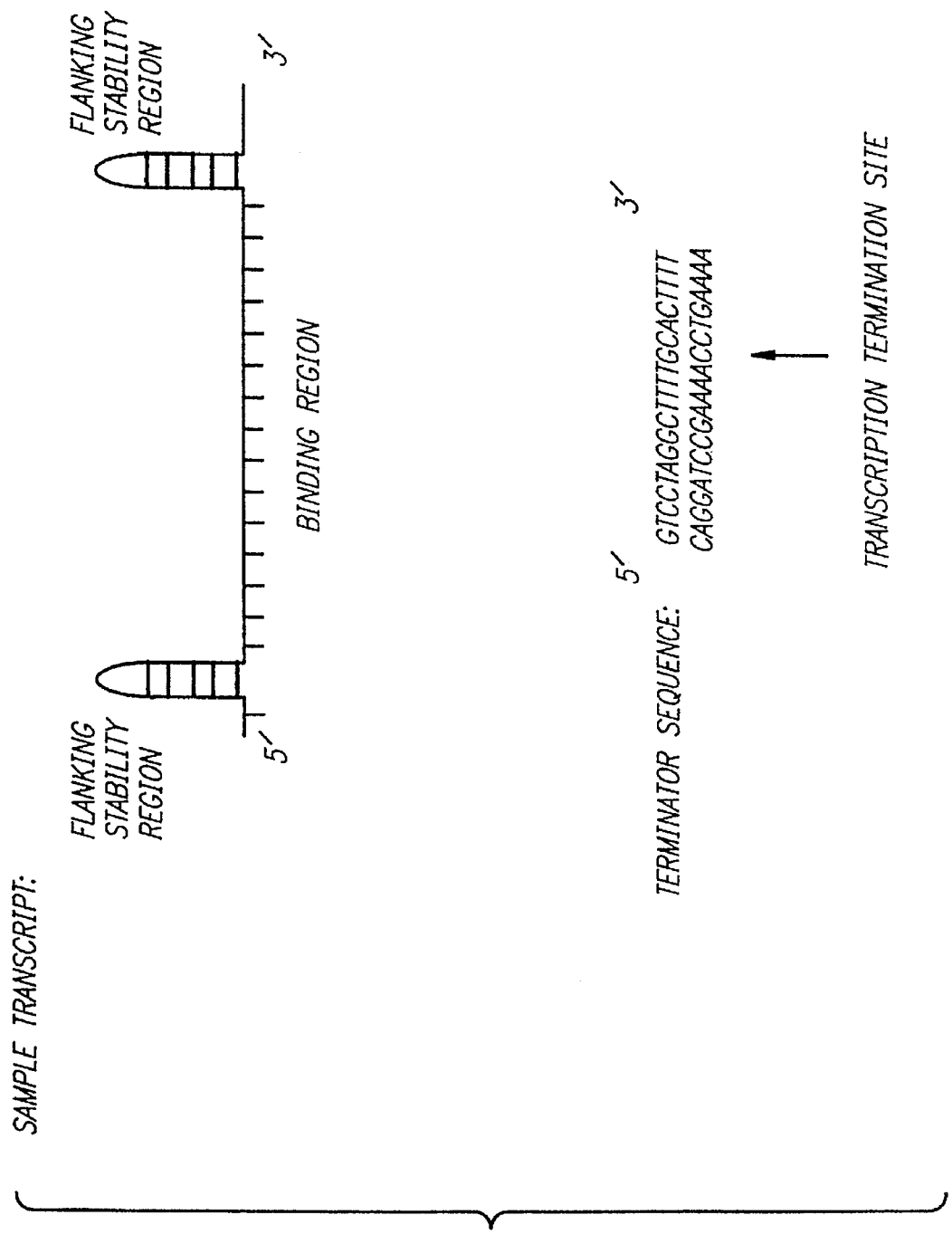

The boxed regions in FIG. 2 (i.e. A box, TATA box) represent natural invariant promotor and terminator sequences with their lengths in base pairs identified below. The straight line regions represent areas where sequence-specific oligonucleotide portions can be inserted. These oligonucleotide portions may be any oligonucleotide to be transcribed, for example, triplex forming oligonucleotides, antisense oligonucleotides, ribozymes, or a combination thereof. The oligonucleotides can be designed for binding to different regions of different DNA or RNA targets, to different regions of the same DNA or RNA target, or to the same region of the same DNA or RNA target. Decisions as to vector design would be based upon whether the experimenter wanted to hit multiple targets broadly or a single target intensely. In addition, as shown in FIG. 2, self complementary ends can be generated on the oligonucleotide which may form small double-stranded hairpin loops. Such double-stranded ends will protect against exonuclease activity, prolong oligonucleotide half-life within the cell, and prevent other oligonucleotide secondary structures from masking key binding regions.

Once the promotor and oligonucleotide sequences have been attached in the correct orientation, they can be inserted into a viral vector (such as an adenovirus or retrovirus) and integrated into the chromosomes of the cells of interest as, for example, the methods described by Sullenger et al. (1990) Molecular and Cellular Biology 10(12): 6512–6523. The result of the integration would produce a continual and large supply of short length oligonucleotides generated by the cell's own transcriptional machinery based upon natural RNA polymerase III promotion initiation, and termination sequences. By varying the multiplicity of viral vector infection, the degree of gene regulation can be modulated.

The advantages of such a RNA polymerase III system for generating antisense and triplex forming oligonucleotides are manifold. RNA polymerase III transcribes at a nearly constant rate and high frequency in almost all mammalian cell types, in marked contrast to the widely used RNA polymerase II based systems which transcribe at lower frequencies and are highly variable with time and cell type. The RNA polymerase III transcription initiation and termination processes are also highly efficient allowing for clean transcription start and stop sites, usually within 1–2 nucleotides. This feature too stands in contrast with RNA polymerase II approaches which generate widely varying transcript lengths with long polyadenylated tails and often hundreds to thousands of trailing 31 nucleotides. In addition, since RNA polymerase III normally generates transcripts that are both selectively transported to the cytoplasm (rRNA, tRNA) and maintained in the nucleus (various snRNA), it may be possible to utilize similar sequences to keep the designed oligonucleotide sequences primarily in the cell compartment of interest.

Several reports have emerged citing the ability of a transfer RNA (tRNA) gene to be used as a carrier for an antisense oligonucleotide (Izant, J. G. (1992) In Gene Regulation: Biological Activity of Antisense RNA and DNA. R. P. Erickson, J. G. Izant, eds. Raven Press (New York), pp. 183–196; and Sullenger, B. et al. (1990) Mol. Cell. Biol. 10: 6512–6523). In one case the oligonucleotide was placed within one of the hairpin loops in the internal region of the gene (Izant, J. G. (1992) In Gene Regulation: Biological Activity of Antisense RNA and DNA. R. P. Erickson, J. G. Izant, eds. Raven Press (New York), pp. 183–196), in another instance, the oligonucleotide was placed on the 3' tailing region of the tRNA (Sullenger, B. et al. (1990) Mol. Cell. Biol. 10: 6512–6523). Both reports demonstrate an antisense effect against a target mRNA using these RNA transcripts, but did not result in the RNase H-mediated cleavage of the target. As with the U6 system, these approaches utilize polymerase III for oligonucleotide production. However, in both of these systems, the oligonucleotide is within a much larger sequence containing key promoter elements. Consequently, the antisense binding sequence is constrained to regions where the tRNA can be transcribed normally, and is likely masked by structure of the much larger tRNA sequence, or interfere with intragenic promoter function. In addition, these tRNA strategies may result in oligonucleotides which are close enough in structure to native tRNA molecules to disrupt translation of mRNA into proteins or result in the transport of the chimeric oligonucleotide out of the nucleus.

By contrast, U6 and 7SK -based systems require no internal promoter as opposed to the tRNA chimeric genes, and thus can be composed almost entirely of the oligonucleotide of interest. This feature is important in determining and designing the secondary structure of the transcript to maximize the oligonucleotide binding sequence while also maximizing stabilizing flanking sequences. In one preferred embodiment, a 5' U6 flanking sequence was maintained to invoke the enzyme(s) which recognize and cap the transcript. Another technique which may provide both oligonucleotide accessibility and stability is to build in a 5' and 3' self-complementary hairpin, creating a lariat-like structure with the oligonucleotide within the loop. As the RNA is small, secondary structure prediction algorithms have utility in the design of these transcripts. The U6 system also has nearly all of the native U6 deleted from the resulting chimeric gene. This feature eliminates the possible sequestering of oligonucleotide within the active spliceosome, as well as eliminates possible toxicity from dysfunctional chimeric U6 RNA that can carry out only a subset of the functions of the native U6 RNA.

There is another chimeric gene that has been developed by others, which utilizes the promoter of U2 snRNA gene (Izant, J. G. (1992) In Gene Regulation: Biological Activity of Antisense RNA and DNA. R. P. Erickson, J. G. Izant, eds. Raven Press (New York), pp. 183–196). Like the U6-based chimeric gene, the promoter is entirely upstream, but unlike the U6-based chimeric gene, it is transcribed by RNA polymerase II. These chimeric genes also retain nearly all of the native U2 gene which is considerably longer and more complex in structure than is the tRNA gene. Thus, accurate predictions of structure and accessibility of these oligonucleotides are significantly more difficult to obtain a priori. However, the kinetics of expression, stability, intracellular localization, and absolute RNA transcript levels have not been characterized in these chimeric genes.

In the oligonucleotide generators of the invention, the optional use of viral integration allows for the modulation of infection with the oligonucleotide generator, and thus the amount of transcripts generated. Such a feature will be invaluable in generating dose-response curves to a given target. Viral integration will also generate cells that are healthy and otherwise functioning and replicating normally, while producing the constant supply of oligonucleotides. As opposed to plasmid transfection techniques, the integration is permanent and does not require continuous selective pressure. Once the producer lines of virally integrated cells are generated, a variety of primary cells and cell lines can be infected, a variety of combination and concentrations of infection can be tried, and the effect of various strategies of gene regulation can be compared (i.e. antisense versus triplex).

An additional advantage arises from the capability to hit multiple targets by the use of more than one oligonucleotide sequence within a transcript. Multiple sequences could target the start codon, a splice site, and the ribosomal binding sequence within a single mRNA, thus increasing the likelihood of blocking subsequent translation of that protein. Alternatively, multiple mRNA's could be used as targets leading to downregulation of multiple proteins along a common pathway.

We have designed, constructed, and tested a system for the intracellular generation of short sequence-specific oligonucleotides in extremely high yield for the purposes of gene regulation. The system, when transfected into cells by electroporation, produces the desired oligonucleotide in high quantity. We have analyzed the production of our transcript by both Northern and RNAse Protection assays, and both analyses show that the quantity of oligonucleotide produced is at least several orders of magnitude higher than the quantity of a typical messenger RNA. However, should lower concentrations be warranted, smaller doses of our system result in a lower quantity of the oligonucleotide. Experimentation has also shown that the oligonucleotide is sufficiently stable (i.e., it is composed of only one strong band; no degradation products are observable), and is of an exact "user-definable" length.

This system has the advantage of user flexibility in oligonucleotide sequence, length, and yield not capable with current intracellular nucleic acid delivery techniques. Its intracellular location and seemingly constant production bypass uptake and sequestration concerns which limit the utility of current extracellular nucleic acid delivery techniques. This system is also compatible with viral integration for conferring permanence in oligonucleotide generation. We expect our system to result in enhanced capacity for gene regulation by antisense, triplex, or any other application of oligonucleotides in cells.

The in vivo oligonucleotide generator according to the invention can be used for permanently downregulating or upregulating cellular proteins of interest. Examples of effective antisense, triplex-forming, and rybozyme oligonucleotides, as well as strategies for developing new efficacious oligonucleotides are known in the art and are thus not described exhaustively herein. Examples of proteins for which downregulation might be indicated include transplantation antigens (e.g. ICAM, MHC classes I and II antigens), hormones, cellular adhesion molecules, clotting proteins, oncogene products, and proteins of viruses which form latent infections in human, including but not limited to Herpes, HIV, CMV, and human papilloma viruses. Information concerning the use of oligonucleotides to downregulate transplantation antigens is found in PCT/US 93/00797. Examples of proteins for which upregulation might be indicated include underexpressed proteins in deficiency states.

The in vivo oligonucleotide generator according to the invention can be used for control of viral, parasitic or mycotic replication, by targeting key replication and protein sequences (such as for example the T antigen in SV40) and to prevent viral infection by downregulating necessary attachment proteins.

The in vivo oligonucleotide generator according to the invention can be used to block the proliferative effect of cellular or viral oncogenes such as myc, myb, or fos and therefore reduce or prevent neoplasm growth and tissue invasion.

The in vivo oligonucleotide generator according to the invention can be used to create new genetically altered organisms, cells and tissues, useful for example in agriculture and in human and veterinary medicine.

In the Examples section below we demonstrate that the levels of production of the RNA transcripts, e.g. U6ON, produced by the oligonucleotide generators of the invention can rival and even exceed those of the native U6 snRNA ($5 \times 10^4$ to $5 \times 10^6$ copies/cell) and, like native U6 RNA, these RNA oligonucleotides can be capped and remain intranuclear in controlled concentrations which may range from 160 µM to 16 mM. U6ON production occurs rapidly upon transfection and can still be detected up to one week after transfection, as 50% inactivation of the parent plasmid from steady-state requires approximately 4 days. This long-lived production suggests that in slowly growing cell populations, longer time points (i.e., longer than the typical 48 to 72 hours) may be used for measuring a biological response from a transient transfection of the oligonucleotide generator. In addition, this long-lived production may allow for the detection of biological effects of antisense or triplex oligonucleotides after transient transfection, even when the target mRNA and/or protein is fairly stable. For example the half-life of U6ON transcripts is estimated to be 1 hour; however, transcript stability is dependent upon the sequence of the oligonucleotide insert.

The sequence of the insert is able to affect the ability of the transcript to retain the initial 5' hairpin structure, and thus the ability to obtain a 5' cap. Correlations have been observed between RNA secondary structure predictions and experimental determinations of transcript levels containing different oligonucleotide insert sequences. When the algorithm predicted the loss of the 5' hairpin, dramatic decreases in transcript levels were seen experimentally after electroporation and Northern blotting. Low transcript levels reflect either a decrease in production or an increase in degradation. As the U6 gene has consistently been shown to require only upstream promoter sequences for transcription (Kunkel & Pederson (1989) Nucleic Acids Res. 17: 7371–7379; and Willis, I. M. (1993) European J. of Biochem. 212: 1–11), the low transcript levels seen with some oligonucleotide insert sequences cannot be due to a decrease in production, and must therefore are due to an increase in degradation. U6 stability has been attributed primarily to its 5' cap and its extensive hybridization with self+U4 (Terns, M. P. et al. (1993) Genes and Development 7: 1898–1908). As all of the chimeric oligonucleotide generator genes have the U6/U4+ self hybridization regions deleted, it becomes more likely that differences in stability are due to the presence or absence of a 5' cap. Finally, correlations between modeling studies and experimental data point toward the retention of a 5' hairpin structure as a means of linking oligonucleotide sequence, retention of the 5' cap, transcript stability, and thus, absolute transcript levels. Consequently, in the design of an oligonucleotide insert, the overall secondary structure of the RNA transcript has importance in optimizing transcript stability and steady-state transcript levels.

There are a variety of potential applications for a system which generates sequence-specific short RNA oligonucleotides in high yield within the cell nucleus. For example, antisense oligonucleotides can be generated intracellularly in levels several orders of magnitude greater than typical sense mRNA molecules and far greater than antisense mRNA generated by more traditional vectors that rely on RNA polymerase II for transcription. In addition, the ability to produce short transcripts minimizes the chances that the binding region for a targeted biological effect is masked by secondary structure which can occur with much larger antisense mRNA transcripts that do not have pre-determined length or sequence.

The present invention also provides a means for the generation of intranuclear triplex RNA oligonucleotides. Pyrimidine-rich triplex RNA oligonucleotides which bind in a parallel fashion with respect to the corresponding purine strand of a homopurine/homopyrimidine duplex (Felsenfeld, G. et al. (1957) J. Am. Chem. Soc. 79:2023–2024), have a greatly increased binding affinity over their triplex DNA oligonucleotide counterparts (Roberts & Crothers (1992) Science 258: 1463–1467; and Escude, C. et al. (1993) Nucleic Acids Res. 21: 5547–5553). The high concentration of a triplex RNA oligonucleotide which is both generated and retained in the nucleus in vast excess over its DNA duplex target may drive triplex binding to a critical element on a gene promoter, and block subsequent gene expression.

In addition to antisense and triplex oligonucleotides, the vectors of the present invention may be used in generating longer length ribozyme transcripts for use in binding and cleaving target mRNA. Combinations of triplex and antisense oligonucleotides as well as ribozymes targeted to a single gene may also yield synergistic approaches to the selective repression of gene expression.

Other potential uses of the present invention include the quenching of specific single-stranded nucleic acid binding proteins by short RNA sequences, or generating self-complementary RNA hairpins that can mimic known DNA binding consensus sequences, thus quenching specific DNA binding transcription factors. These embodiments of the present invention rely on the nuclear localization of abundant and sufficiently stable oligonucleotides with short and fully defined sequences to allow for reasonable approximation of secondary structure.

Triplex Blotting

In another aspect, the invention features a method for screening oligonucleotide sequences that are candidates for triplex formation with a double-stranded DNA target site, including steps of identifying a sequence corresponding to the target site, producing and isolating oligonucleotide sequences that appear likely to bind to the target site, prehybridizing and hybridizing the isolated oligonucleotide sequences with a labeled double-stranded probe having the sequence of the target site, removing unbound probe from the oligonucleotide sequences, and detecting the label to identify probe-bound oligonucleotides.

In its most general aspects the triplex blotting invention described herein embodies two different methods of measuring triplex formation and the strength of triplex binding. The first method comprises (a) attaching a single-stranded nucleic acid to a solid support; (b) contacting the solid support with a fluid comprising a labeled double-stranded probe; (c) separating the unbound probe from the solid support; and (d) quantifying the amount of labeled double-stranded probe bound to the solid support. The second method comprises (a) attaching a double-stranded nucleic acid to a solid support; (b) contacting the solid support with a fluid comprising a labeled single-stranded probe; (c) separating the unbound probe from the solid support; and (d) quantifying the amount of labeled single-stranded probe bound to the solid support.

The attachment of single and double-stranded nucleic acids to solid supports can be accomplished by any method known in the art including, but not limited to, Northern blotting transfer techniques, slot or dot blotting techniques, or by the nucleic acid chip technology of Affymax. The single-stranded nucleic acid used in the triplex blotting method of the invention can be either DNA or RNA. The double-stranded nucleic acid used in the triplex blotting method of the invention can be DNA:DNA, DNA:RNA, or RNA:RNA duplexes. In all cases modified nucleotides, and nucleotide linking groups (groups to replace internucleotide phosphodiester linkages) can be used.

The label on the labeled single and double-stranded probes can be any nucleic acid label known in the art including, but not limited to, radionuclides (e.g. $^{32}P$ and $^{35}S$), fluorescent dyes, and biotin.

The separation of the unbound probe from the solid support can be accomplished by any washing technique known in the art for use with Northern, Southern and slot blotting. Such washing techniques may include multiple washes at increasing stringencies while monitoring the ratio of specifically bound labeled probe to background labeled probe, for example with a geiger counter for probes labeled with $^{32}P$ as is typically done with Northern blotting. Increasing stringency can be accomplished by reducing the concentration of salts generally, and Na$^+$ particularly, by increasing the temperature, or by increasing the pH.

The quantification of the amount of labeled single- or double-stranded probe bound to the solid support may be preformed by any method known in the art for the quantification of the particular label used. For example in the case of a radionuclide the quantification can be performed by autoradiography followed by densitometry or scintillation counting.

In one preferred embodiment of the triplex blotting invention described herein, is for use in drug screening assays. For such assays, the single-stranded nucleic acid is attached to the solid support and the double-stranded nucleic acid is labeled and used as a probe. In this case the probe is designed to mimic a particular target site for triplex binding. A large number of single-stranded nucleic acids with different sequences are attached to one or more solid supports in an ordered and cataloged manner. The solid support is contacted with a fluid comprising the labeled double-stranded probe/target site. After the unbound probe is separated from the solid support, the amount of labeled double-stranded probe bound to each different single-stranded nucleic acid is quantified. The single-stranded nucleic acid with the highest amount of labeled double-stranded probe bound to its position on the solid support is the best candidate for a triplex-forming oligonucleotide.

The practice of the present invention will employ, unless otherwise indicated, conventional techniques of protein chemistry, molecular biology, microbiology and recombinant DNA technology, which are known to one of ordinary skill in the art. Such techniques are explained fully in the literature. See, e.g., R. K. Scopes, Protein Purification Principles and Practice, 2nd ed. (Springer-Verlag 1987); S. Colowick and N. Kaplan, Eds., Methods in Enzymology (Academic Press, Inc.); Sambrook, Fritsch & Maniatis, Molecular Cloning: A Laboratory Manual, 2nd ed. (Cold Spring Harbor Laboratory Press 1989); M. J. Gait, Ed., Oligonucleotide Synthesis (1984); and D. M. Weir and C. C. Blackwell, Eds., Handbook of Experimental Immunology, Vols. I–IV (Blackwell Scientific Publications 1986).

All patents, patent applications and publications mentioned herein, whether supra or infra, are hereby incorporated herein by reference in their entirety.

Described below are examples of the present invention which are provided for illustrative purposes, and not to limit the scope of the present invention. In light of the disclosure, numerous embodiments within the scope of the claims will be apparent to those of ordinary skill in the art.

EXAMPLES

Example 1

Initial Characterization of In Vivo Oligonucleotide Generator

Expression and Lack of Toxicity

Tests of the system using several different cell populations (breast cancer MDA453 cells; human embryonic kidney 293 cells) and have produced comparable results. Normal U6 small nuclear RNA which utilizes identical transcriptional assemblies were unaffected by transfections of up to 20 µg of the chimeric ON-producing gene; Cells producing the oligonucleotide grow normally and demonstrate no morphologic changes at these levels of transfection.

Kinetics

We have examined how fast the oligonucleotide generator can produce RNA oligonucleotides after cell transfection with the parent plasmid. We electroplated cells and examined total RNA at 12 hours, 24 hours, and 48 hours post-transfection. Using a system substantially as described above, the oligonucleotide generator reaches a near steady-state level at about 12 hours post-transfection. These data indicate that the oligonucleotide is formed rapidly, and therefore may have immediate activity once the system is introduced into cells.

Dose-response

We have examined the effect of increasing the amount of the oligonucleotide generator in cells with respect to RNA oligonucleotide levels in cells 48 hours after transfection. To summarize, when cells are transfected with 0, 5, 10, 20, or 40 micrograms of the generator using a system substantially as described above, the amount of RNA oligonucleotide isolated from cells increases linearly. Thus, it is possible to drive cells to produce enormous levels of a single RNA oligonucleotide. At 40 microgram transfections, we estimate that we can produce on the order of 1–5 million copies per cell. This level is very far in excess of that achievable with typical mRNA species.

Effect of the Oligonucleotide Generator on the Cells

As the oligonucleotide generator produces such high levels of RNA oligonucleotides in the cell, we examined the effect of the oligonucleotide generator on two parameters, namely, cell growth and normal U6 RNA levels. After transfection of $10^7$ cells with 0, 5, or 10 micrograms of an oligonucleotide generator substantially as described above, no effect on the ability of cells to divide and grow normally was detected, and no significant effect on native U6 levels, which might have indicated competition for transcription factors, was detected. However, at levels of transfection $\geq 20$ µg of the U6ON generator, cellular levels of U6 RNA decreased. Further analysis indicated that this decrease was due to a lessened stability of the cellular U6 RNA.

Example 2

Targeting the HER2 Proto-Oncogene Promoter with Triple Helix Forming Oligonucleotide Oligonucleotides designed to form local triple helices with the HER2 promoter and interfere with transcription factor binding may potentially inhibit HER2 receptor expression and growth of HER2 overexpressing breast cancers.

We have identified, using promoter deletion mapping, a 125 base-pair core proximal promoter region capable of conferring greater than 30 fold variation in HER2 transcriptional activity. Within this region are several putative protein binding sites (including CAAT, TATA, and a GAGGAA ets-related response element), essential for promotor activity, which both surround and overlap a 41 base-pair purine-rich sequence. Gel mobility shift experiments demonstrate that this 41 base-pair sequence is compatible with triple helix formation by both parallel (pyrimidine-rich) and antiparallel (purine-rich) triplex binding motifs.

We tested oligonucleotides ranging in length from 26 to 41 nucleotides. Increasing oligonucleotide length corresponds with increasing gel retardation, however triplex formation is relatively unaffected by length, demonstrating only sequence-specificity. Antiparallel triplex formation is strongly dependent upon $Mg^{++}$ (0.1 to 10mM), while parallel triplex formation has an additional sensitivity to pH, demonstrating significant loss of hybridization from pH 7.0 to 8.0. These triple helix forming oligonucleotides can inhibit binding of ets-related proteins such as PU.1 to the HER2 promoter.

In addition, transfection of synthetic genes capable of constitutively generating short triple helix forming oligonucleotide transcripts is testing the ability of these oligonucleotides to downregulate both native HER2 receptor levels as well as a co-transfected HER2-driven chloramphenicol acetyltransferase reporter gene. Triple helix forming oligonucleotides and effect of HER2 downregulation on proliferation and tumorigenicity of HER2-positive breast cancer cells have a therapeutic potential.

Example 3

Construction of the Chimeric U6ON Gene

The human U6 gene cloned within the SmaI site of pGem1 (Promega, Madison, Wis.), along with a mutant human U6 gene with bases +25 to +55 replaced by an XhoI restriction site (with A/C substitution at base 24) were generously provided by G. Kunkel and T. Pederson (Kunkel & Pederson (1989) Nucleic Acids Res. 17: 7371–7379). The mutant U6 gene was recloned into a pBluescript (Stratagene, La Jolla, Calif.) vector to produce single-stranded phage and to allow two site-directed mutations at bases +86 and +88 (T to G and G to A, respectively) to create a unique NsiI restriction site. This plasmid, mU6, was then recloned back into pGEM1, cut with XhoI and NsiI, and religated with a synthetic 38 bp duplex fragment bearing 5' XhoI and 3' NsiI compatible overhanging ends (Keystone Laboratories, Menlo Park, Calif.). Incorporation of the synthetic oligonucleotide was verified by Maxam and Gilbert dideoxy DNA sequencing. The resulting transcript arising from this vector, U6ON, is 25 nucleotides shorter than native U6 RNA (82 vs. 107). Sequences of the upper strand of U6ON and other various inserts are as listed:

U6ON:(SEQ ID NO:1)
  5' TCGACTCCTCTTCCTCCTCCACCTCCTC-CTCCCATGCA 3'
U6CTcon(SEQ ID NO:2):
  5' TCGACCTCCCTTCCCTTCCCTTCCCCT-TCCTCCATGCA 3'
U6AS(SEQ ID NO:3):
  5' TCGACATGAGCATTCATCAGGCGGGCAA-GAATGTGATGCA 3'
MU6(SEQ ID NO:4):
  5' TCGAGCATGGCCCCTGCGCAAGGATGA-CACGCAAATGCA 3'

Figure 4C:
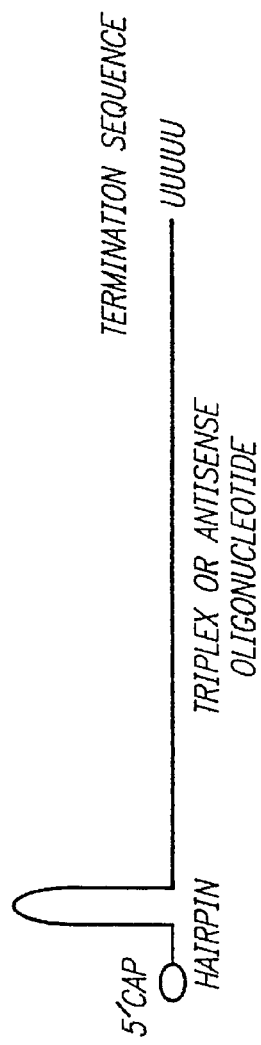
FIG. 4C shows the resulting oligonucleotide which may retain the 5' hairpin, followed by the oligonucleotide (bold line) and the native U6 uridine-rich sequence.

FIG. 4 illustrates schematically the structure of the native U6 snRNA gene, the modifications involved in generating the chimeric gene, and the resulting RNA oligonucleotide transcript, U6ON. As shown, the upstream promoter and enhancer regulatory regions, the initial 25 bp (with A/C substitution at base 24), and the terminal 19 bp of the native U6 gene were retained in the chimeric gene. Mutagenesis and restriction digest removed the remaining native U6 internal sequence in order to create a hybrid of native and synthetic sequences in a gene designed to express any oligonucleotide of interest. As shown in FIG. 4C, the transcribed RNA oligonucleotide was designed to retain the original 5' hairpin, in order to obtain the 5' γ-monomethyl phosphate cap. This initial sequence is followed by the sequence-specific oligonucleotide and the native U6 uridine-rich 3' terminus. The total length of the resulting transcript is a function of the synthetic oligonucleotide inserted, a 38 bp duplex was inserted yielding a U6ON of 82 nucleotides.

Example 4

Cell Culture and Gene Transfection

The human embryonic kidney cell line, 293, and the human breast cancer cell line, MDA453 (ATCC, Rockville, Md.), were transfected by electroporation (250 V, 960 µF) with 5 µg to 40 µg of the chimeric gene or promoterless plasmid DNA. Cell viability after transfection ranged from 40-60% (with 293 cells showing slightly higher tolerance to electroporation than MDA453 cells) and was unaltered by increasing gene transfection dosage up to 40 µg/$10^7$ cells. 293 cells were cultured in minimal essential media with Earle's basic salt solution, 10% fetal calf serum supplemented with 100 U/ml penicillin and streptomycin in 5% $CO_2$ incubators. MDA453 cells were cultured in Leibovitz L-15 media with 10% fetal calf serum supplemented with 100 U/ml penicillin and streptomycin in the absence of $CO_2$. Where indicated, cell counts were obtained by Coulter counting.

Example 5

RNA Isolation and Northern Blotting

Total cellular RNA was isolated 48 hours after transfection by the guanidinium isothiocyanate/cesium chloride centrifugation technique (Glisin, V. R. et al. (1974) Biochemistry 13: 2633–2643). RNA (10–20 µg, as indicated in Brief Description of the Drawings) was electrophoresed in 8% polyacrylamide/7 M urea gels, electroblotted onto nylon filters (Amersham, Arlington Heights, Ill.) in 8 mM $Na_2HPO_4$/17 mM $NaH_2PO_4$ buffer for 3 hours at 350 mA, and then UV cross-linked onto the filters for 2 min. Probes to detect native U6 and the generated RNA oligonucleotide were radiolabeled by random-priming from an 800 bp BamHI/EcoRI fragment taken from the original U6 gene or the chimeric gene within pGem1. After membrane hybridization and autoradiography, bands were either quantitated by scanning densitometry or cut from the filter for scintillation counting.

To prepare nuclear and cytoplasmic RNA fractions, transfected cells were electroporated with 10 µg of the chimeric gene and after 48 hours, cells were washed twice in phosphate buffered saline (PBS) without calcium or magnesium, and the nuclei extracted by gentle hypotonic lysis (Maniatis, T. (1989) Molecular Cloning: a laboratory manual. T. Maniatis, E. Fritsch, J. Sambrook, eds. Cold Spring Harbor Press (New York: Cold Spring Harbor)). After 15 seconds of vortexing and 5 min at 4° C., nuclei were pelleted and rewashed in PBS. RNA from the nuclear pellets and the aqueous cytoplasmic fraction was separately extracted in 4 M guanidinium isothiocyanate/cesium chloride.

Example 6

Cellular Transcription Arrest

Intracellular stabilities of U6ON and normal U6 were assessed by halting cellular transcription with 10 µg/ml of Actinomycin D (Sigma, St. Louis, Mo.) administered to cell cultures 48 hours after transfection. Cells were harvested and total cellular RNA was isolated at 0, 0.5, 1, 2, and 4 hour time points after Actinomycin D treatment. Northern blotting was performed to quantitate U6 and U6ON transcript levels.

Example 7

RNA immunoprecipitation 293 cells were transfected with 20 µg of the chimeric gene or promoterless plasmid DNA, and after 48 hours, total cellular RNA was isolated. 20 µg of this RNA was used for immunoprecipitation with 0.5 mg of a 5' γ-monomethyl phosphate cap-specific antibody, generously provided by R. Reddy. Incubation and precipitation conditions were followed as previously described for this antibody (Gupta, S. et al. (1990) J. Biol. Chem. 265: 19137–19142).

Example 8

RNA Secondary Structure Prediction

Proposed secondary structures of the RNA oligonucleotides were obtained using the Martinez algorithm RNAFOLD (Martinez, H. (1990) Meth. in Enzymol. 183: 306–317). In all models, loop destabilization was allowed and a maximum "bulge" size of 30 nucleotides was permitted.

Example 9

Intracellular Generation of RNA Oligonucleotides
Generation in Two Cell Types

Figure 5A:
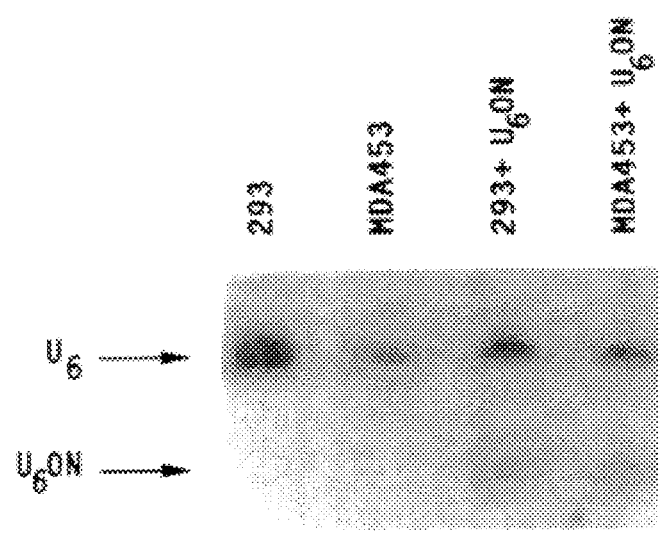
FIG. 5 is a half-tone reproduction of Northern blots which demonstrate the production and nuclear localization of the U6ON transcript. For FIG. 5A, MDA453 and 293 cells were transfected with either 10 μg of the chimeric U6ON gene or 10 μg of promoterless plasmid DNA. Total cellular RNA was isolated 48 hours later followed by Northern blotting with both U6 and U6ON radiolabeled probes. For FIG. 5B, MDA453 cells were transfected with increasing quantities of the chimeric gene followed by RNA isolation at 48 hours and Northern blotting as described above. All transfections contained 40 μg total DNA, with promoterless plasmid DNA supplementing the chimeric gene as necessary. For FIG. 5C, MDA453 cells were transfected with 10 μg of the chimeric gene and after 48 hours, RNA was separated into nuclear and cytoplasmic fractions. The nuclear fraction shown above contained the U6ON transcript along with the native U6 snRNA. All Northern blots were generated from 10 μg of RNA loaded/well.

MDA453 and 293 cells were transfected with either 10 µg of the chimeric U6ON gene or 10 µg of promoterless plasmid DNA as described in Example 5. Total cellular RNA was isolated 48 hours later followed by Northern blotting with both U6 and U6ON radiolabeled probes as described in Example 6. In FIG. 5A, the intracellular generation of this sequence-specific RNA oligonucleotide, U6ON, is shown in two different human cell lines, MDA453 and 293, following transfection with 10 μg of the chimeric gene. In this experiment and in other replications of this experiment with other human cell types, no cell-type specificity in production has been observed in any of 5 different human cell lines tested. However, transcript levels varied in accordance with the amount of chimeric gene transfected within the range of 5 to 40 μg plasmid DNA per $10^7$ cells.

Linear Correlation Between Transcription Rate and Transfection Dose

Figure 5B:
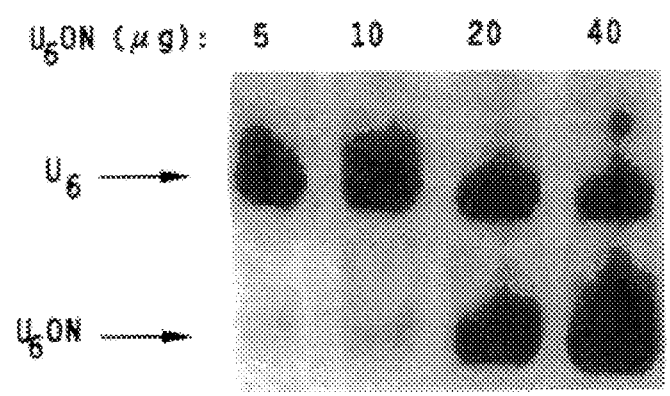

MDA453 cells were transfected with increasing quantities of the chimeric gene followed by RNA isolation at 48 hours and Northern blotting as described above in Examples 5 and 6. All transfections contained 40 μg total DNA, with promoterless plasmid DNA supplementing the chimeric gene as necessary. FIG. 5B illustrates that within this 8-fold range of transfected gene dosage, a near 100-fold linear variation in U6ON transcript levels is observed. Using native U6 RNA levels (known to be present at roughly $0.5 \times 10^6$ copies per cell (Sauterer, R. et al. (1988) Exptl. Cell Research 176: 344–359)) as a marker, densitometry was performed to compare the U6ON bands at each transfection level with the U6 band at the 5 μg gene transfection level. Previous results have shown that native U6 transcript levels do not vary upon transfection with 0, 5, or 10 μg U6ON gene transfection levels, but do show transient decreases in transcript levels after transfection with 20 to 40 μg of the U6ON gene). This analysis yields estimates of steady-state intracellular U6ON transcript levels to range from $5 \times 10^4$ to $5 \times 10^6$ copies/cell at 48 hours post-transfection, depending upon quantity of gene transfected. If nuclei are assumed to be spherical and to have an average diameter of 10 μm, these values correspond to an intranuclear (see FIG. 5C) concentration ranging from 160 μM to 16 mM. These calculations assume an even distribution of the U6ON gene throughout the electroporated cell population, as is found for the U6 gene. Thus, errors resulting from this assumption may lead to higher actual intracellular transcript concentrations.

Localization to the Nuclear Fraction

Figure 5C:
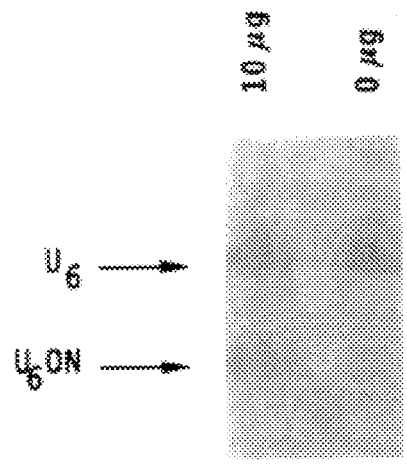

MDA453 cells were transfected with 10 μg of the chimeric gene and after 48 hours, RNA was separated into nuclear and cytoplasmic fractions as described in Example 6. The nuclear fraction shown above contained the U6ON transcript along with the native U6 snRNA. All Northern blots were generated as described in Example 6 from 10 μg of RNA loaded/well. As shown in FIG. 5C, when RNA from gene transfected or mock transfected MDA453 cells is separated into nuclear and cytoplasmic fractions, U6ON is found predominantly in the nuclear fraction, along with native U6. U6ON could not be detected to any significant extent in the cytoplasmic fraction. Moreover, the relative ratio of U6 to U6ON found in the nuclear fraction mirrors the ratio found in total cellular RNA samples.

Example 10

Kinetic Analysis of U6ON Expression

FIG. 6 illustrates the rapid production, steady-state levels, and decaying expression of U6ON in 293 cells and MDA453 cells.

Figure 6A:
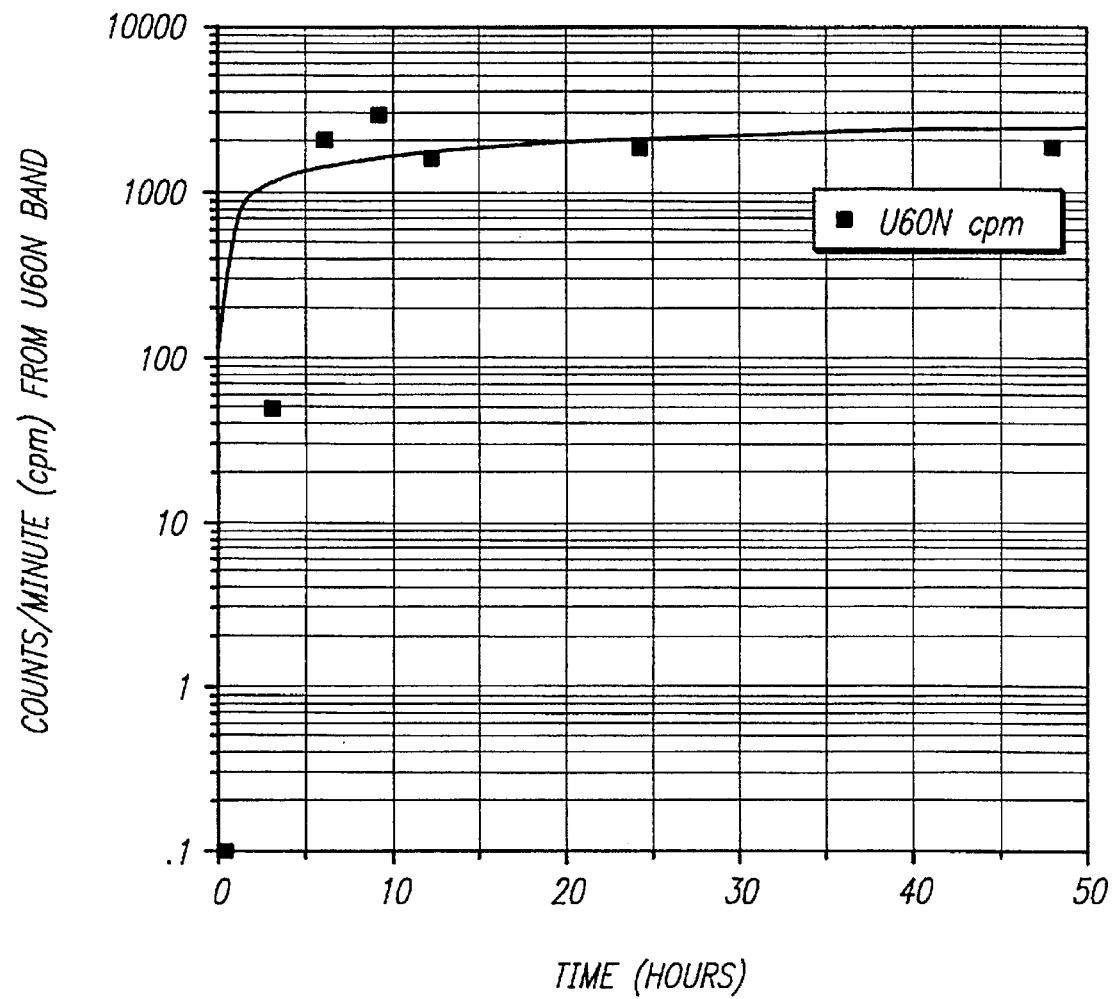
FIG. 6 is a graph and a half-tone reproduction of a Northern blot which demonstrates the kinetics of U6ON expression. For FIG. 6A, 293 cells were transfected with 20 μg of the chimeric gene and total cellular RNA was isolated at 0, 3, 6, 9, and 12 hours time points. After Northern blotting (10 mg RNA added/well) and autoradiography with a U6ON radiolabeled probe, the U6ON bands were cut from the filter and scintillation counted. For FIG. 6B, MDA453 cells were transfected with 20 mg of the chimeric gene and total cellular RNA was isolated at 48, 72, 96, 120, 144, and 168 hour time points. Northern blotting followed with 20 μg of RNA added/well.

Rapid Production and Steady State Levels 293 cells were transfected with 20 μg of the chimeric gene and total cellular RNA was isolated at 0, 3, 6, 9, and 12 hours time points. After Northern blotting (10 μg RNA added/well) and autoradiography with a U6ON radiolabeled probe, the U6ON bands were cut from the filter and scintillation counted. As shown in FIG. 6A, analysis over the first 48 hours post-transfection shows that U6ON expression from the chimeric gene begins within 3 hours post-transfection, and reaches steady-state levels in less than 10 hours. Between 12 hours and 48 hours post-transfection, steady-state U6ON levels are constant.

Decaying Expression

MDA453 cells were transfected with 20 μg of the chimeric gene and total cellular RNA was isolated at 48, 72, 96, 120, 144, and 168 hour time points. Northern blotting followed with 20 μg of RNA added/well. The Northern blot shown in FIG. 6B demonstrates the decline in U6ON transcript levels out to 168 hours post-transfection where production is diminished but still readily detectable.

Example 11

Intracellular Stabilities of the Chimeric Gene and the U6ON Transcript

Estimation of U6ON Degradation Rate

Figure 6B:
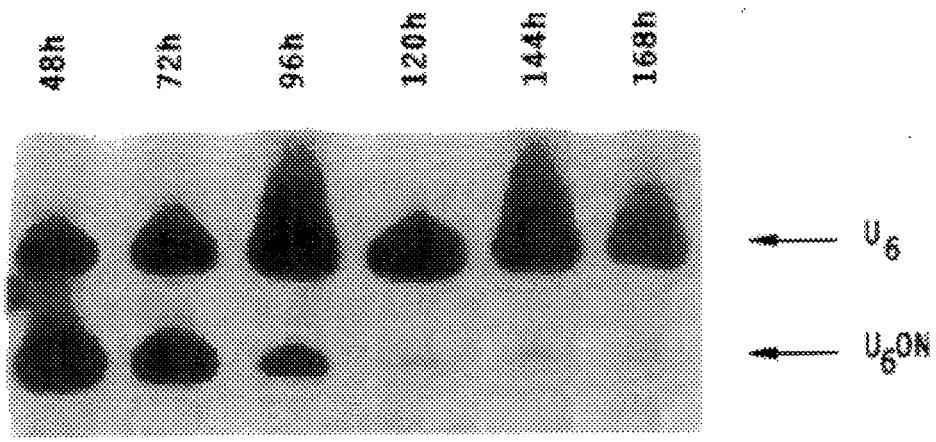

Cell counting in parallel with the RNA isolations of FIG. 6B allowed the U6ON band densities to be normalized to account for the dilutional effects of cell division. Normalized band densities were plotted as a function of time to determine the rate of chimeric gene degradation (or inactivation).

Figure 7B:
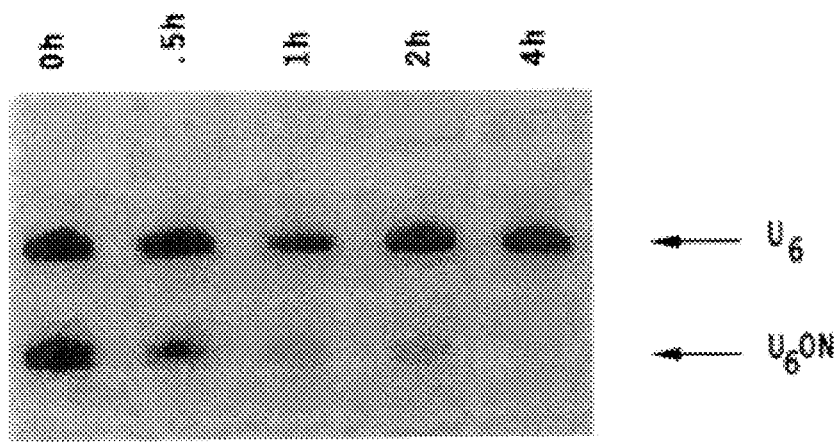
FIG. 7 is a graph and a half-tone reproduction of a Northern blot which demonstrates the intracellular stabilities of the chimeric gene and the U6ON transcript. For FIG. 7A, cell counting in parallel with the RNA isolations of FIG. 7B allowed the U6ON band densities to be normalized to account for the dilutional effects of cell division. Normalized band densities were plotted as a function of time to determine the rate of chimeric gene degradation (or inactivation). For FIG. 7B, 293 cells were transfected with 5 μg of the chimeric gene and after 48 hours, cellular transcription was halted by a 10 μg/ml treatment of Actinomycin D. At 0, 0.5, 1, 2, and 4 hour time points, RNA was isolated. Northern blotting (20 μg RNA/well) with U6 and U6ON radiolabeled probes, followed by densitometry of the U6ON bands, allowed for the determination of U6ON half-life.
Figure 7A:
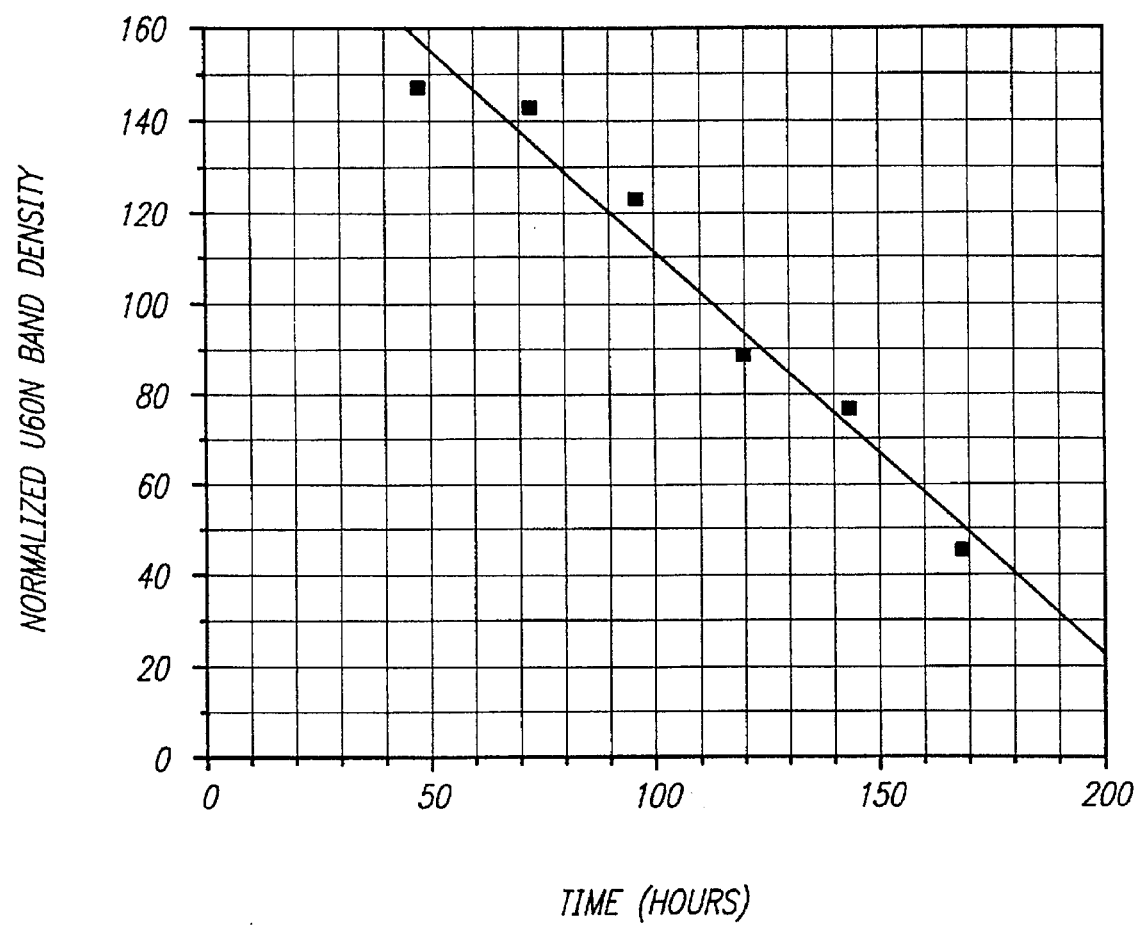

Specifically, intracellular stability of the transfected gene was estimated under the assumption that the observed decline in U6ON transcript levels between 48 hours and 168 hours (FIG. 6B) arises predominantly from two major causes: plasmid degradation (or functional inactivation) and the dilutional effect of cell division (given the equal amount of RNA loaded per lane). The dilutional effect of cell division was accounted for by cell counting in parallel with RNA isolation from 48 hours to 168 hours, and normalizing the Northern blot density values by these cell counts. (Normalized band density=[absolute cell count/cell count at 48 hours]* raw band density) The rate of plasmid degradation (or inactivation) was then estimated as the amount of time required for transcript levels to diminish by 50% from steady-state (48 hours) levels. Cell counting revealed a 38 hour average doubling time from 48 hours to 120 hours, after which time, cell confluence was reached. From 120 hours to 168 hours, absolute cell counts declined slightly. As shown in FIG. 7A, there was a relatively constant plasmid degradation (or inactivation) rate after this normalization procedure, suggesting a zero-order decay process with plasmid half-life ($\tau_{1/2}$) determinations dependent on the initial (48 hours) plasmid levels. Thus, given the above assumptions and constraints, after a 20 μg transfection of the chimeric gene into $10^7$ cells, approximately 50% of the chimeric gene remains functional after 96 hours (4 days). Variations of this estimate in different cell types would be expected.

Determination of U6ON half-life 293 cells were transfected with 5 μg of the chimeric gene and after 48 hours, cellular transcription was halted by a 10 μg/ml treatment of Actinomycin D, as described in Examples 5 and 7. At 0, 0.5, 1, 2, and 4 hours time points, RNA was isolated as described in Example 6. Northern blotting (20 μg RNA/well) with U6 and U6ON radiolabeled probes, followed by densitometry of the U6ON bands, allowed for the determination of U6ON half-life, as described in Example 6. Thus, the intracellular $\tau_{1/2}$ of the U6ON transcript was directly measured by halting cellular transcription with Actinomycin D treatment 48 hours after transfection with 5 µg of the chimeric gene, and monitoring the decay of intensity from the U6ON band in Northern blots. The native U6 band was also monitored as a control since its intracellular $\tau_{1/2}$ is known to be 16-24 hours (Sauterer, R. et al. (1988) Exptl. Cell Research 176: 344-359; and Terns, M. P. et al. (1993) Genes and Development 7: 1898-1908). FIG. 7B demonstrates the decline in U6ON band intensity between 0 hours and 4 hours following transcription arrest, indicating an intracellular $\tau_{1/2}$ of approximately 1 hour after quantitation by densitometry. This analysis also confirms the prolonged stability of native U6. Similar U6ON $\tau_{1/2}$ values were obtained when the experiment was repeated with 10 µg and 20 µg gene transfections. Such results indicate that increases in absolute U6ON steady-state transcript levels do not affect U6ON $\tau_{1/2}$ determinations, consistent with a first-order process of transcript degradation.

Example 12

Measurement of 5' γ-Monomethyl Phosphate Capping for U6ON

To determine whether the retention of the capping signal of native U6 in the U6ON gene allowed for the production of capped U6ON transcripts, RNA immunoprecipitations with a 5' γ-monomethyl phosphate cap-specific antibody were performed. This antibody has previously been shown to be specific for U6, 7SK, and several other unidentified transcripts which contain this unique 5' cap.

Figure 8:
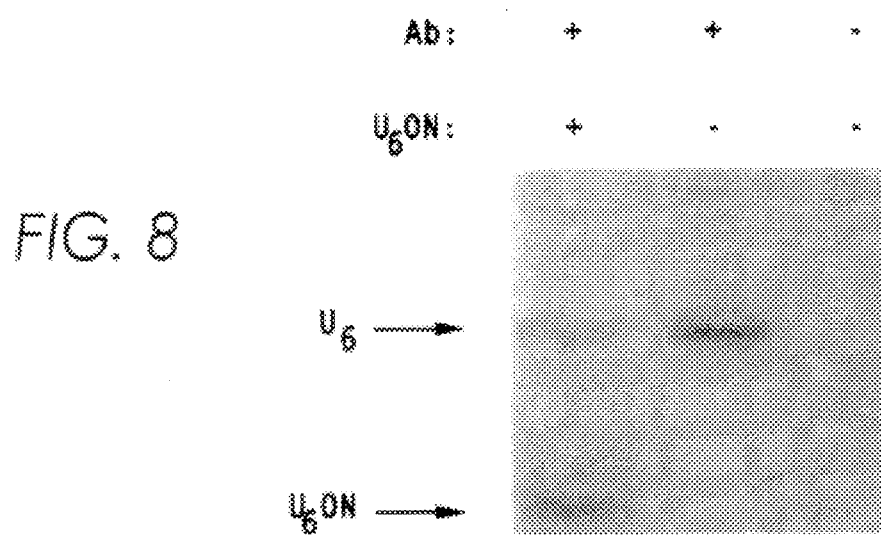
FIG. 8 is a half-tone reproduction of a Northern blot demonstrating the immunoprecipitation of the U6ON transcript with a 5'γ-monomethyl phosphate cap. Total cellular RNA samples isolated after a transfection with 20 μg of U6ON in 293 cells were immunoprecipitated with 0.5 mg of a U6 cap-specific antibody as previously described (Gupta et al. (1990), J. Biol. Chem. 265:19137–19142. Eric Wickstrom, ed. (Wiley-Liss, New York), pp. 143–158). Each immunoprecipitation required 20 μg of initial total cellular RNA. Immunoprecipitated RNA was used for Northern blotting with U6 and U6ON radiolabeled probes.

Total cellular RNA samples isolated after a transfection with 20 µg of U6ON in 293 cells were immunoprecipitated with 0.5 mg of a U6 cap-specific antibody as previously described (Gupta, S. et al. (1990) J. Biol. Chem. 265: 19137-19142) and as reviewed in brief in Example 8. Each immunoprecipitation required 20 µg of initial total cellular RNA. Immunoprecipitated RNA was used for Northern blotting with U6 and U6ON radiolabeled probes as described above in Example 6. As shown in FIG. 8, the U6ON transcript is specifically recognized and immunoprecipitated by this antibody after a 20 µg gene transfection in 293 cells, despite an A/C substitution at base 24. The relative decline in native U6 transcripts immunoprecipitated in the presence of U6ON may be attributed to limiting levels of the antibody, a transient decrease in U6 transcript levels at this higher transfection dose, or competition with U6 RNA for capping enzyme(s) and/or substrates.

Example 13

Insert Sequence-Specific Effects on Transcript Secondary Structure and Intracellular Transcript Levels As seen in FIG. 7, immunoprecipitating total cellular RNA with a U6 cap-specific antibody confirmed that the U6ON obtains the 5' γ-monomethyl phosphate cap structure found on native U6 RNA. However, insert sequences which favor disruption of the initial 5' hairpin for a longer and more stable stem-loop secondary structure may reduce overall transcript stability, and thus steady-state transcript levels.

Transcript Secondary Structure

As shown in FIG. 9A, the conformational output and associated energies of the RNA secondary structure prediction algorithm RNAFOLD (Martinez, H. (1990) Meth. in Enzymol. 183: 306-317), given two different oligonucleotide insert sequences, U6CTcon and U6AS. Despite the same initial nucleotide sequence derived from native U6 in both transcripts, the expected ability to retain the 5' initial hairpin within this sequence differs as a result of the downstream insert sequence. The overall structure and energy values obtained for U6ON and mU6, mirror U6CTcon and U6AS, respectively. Using this structure prediction program, a variety of chimeric genes which generate transcripts that are predicted to prefer one conformation over the other were then designed and constructed.

Predicted Secondary Structure Affects Intracellular Transcript Levels

RNA secondary structure was predicted for 4 different oligonucleotide transcripts and the corresponding chimeric genes were constructed. 20 µg of the chimeric genes were transfected into MDA453 cells, followed by Northern blotting (20 µg RNA added/well) 48 hours later with a U6 probe and a probe for each of the possible RNA transcripts.

Figure 9B:
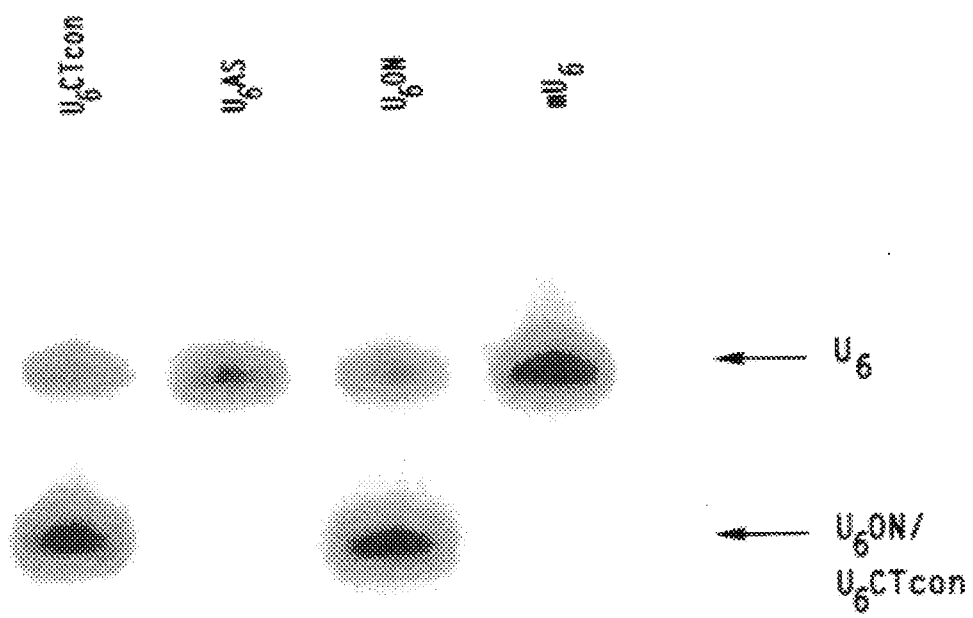
FIG. 9 (SEQ ID NO:14 and SEQ ID NO:15) is diagram of two predicted secondary structures for two RNA transcripts and a half-tone reproduction of a Northern blot, demonstrating the effects of the insert sequence on secondary structure and intracellular transcript levels. For FIG. 9A, RNA secondary structures and associated energies were predicted for two different constructs, U6CTcon and U6AS, using the program RNAFOLD (Martinez, H. (1990) Methods in Enzymology, 183, 306–317). Upper case letters refer to base-pairings, lower case letters refer to mismatches and colons refer to bulged regions. The energies of U6ON and mU6, which were found to have similar structural profiles to U6CTcon and U6AS, respectively, are given in parentheses. For FIG. 9B, RNA secondary structure was predicted for 4 different oligonucleotide transcripts and the corresponding chimeric genes were constructed. 20 μg of the chimeric genes were transfected into MDA453 cells, followed by Northern blotting (20 μg RNA added/well) 48 hours later with a U6 probe and a probe for each of the possible RNA transcripts.

As shown in FIG. 9B, when the algorithm predicts that the 5' hairpin is disrupted by downstream secondary structure (as in U6AS and mU6), steady-state transcript levels are drastically reduced. Only at very long film exposures (6 days) can the bands corresponding to mU6 and U6AS be observed.

Ten chimeric gene constructs have been created to test the hypothesis that the insert sequence can affect intracellular transcript stability and thus steady-state transcript levels by interfering with the formation of the initial 5' hairpin (6 of which the algorithm predicts to retain the initial 5' hairpin, and 4 of which the algorithm predicts to disrupt the initial 5' hairpin). Of these 10 constructs, 8 conform to the pattern of expression and stability shown in FIG. 9B in both MDA453 cells and 293 cells. The two constructs which did not conform were designed to generate stable RNA transcripts, but upon transfection and Northern blotting were found to generate unstable transcripts. All constructs designed to generate unstable transcripts gave rise to unstable transcripts. These disparities may arise from limitations in predicting a preferred RNA state from two competing states in vivo.

Example 14

Targeting the HER2 proto-Oncogene Promoter With Triplex RNA Oligonucleotides

Over the past two decades, multidisciplinary contributions from genetics, biology, and clinical medicine have led to a greatly improved understanding of the molecular mechanisms which underlie cancer induction and progression. Central to this improved understanding is the recognition of the role of proto-oncogenes in the control of cell growth and differentiation (Varmus, H. E. (1984) Ann. Rev. Gen. 18:553-612; Bishop, J. M. (1987) Science 235:305-308; Park, M. and Vande Woude, G. (1989) Cancer: Principles and Practice of Oncology, 3rd ed., In DeVita, V. T., Hellman, S, and Rosenberg, S. A. (eds), pp. 45-66; and Greenberg, M. E. and Ziff, E. B. (1984) Nature 311:433-436). There is considerable data linking the amplification and overexpression of a proto-oncogene with altered cell growth phenotypes (Erisman, M. D. et al. (1985) Mol. Cell. Biol. 5:1969-1976; and Brodeur, G. M. et al. (1984) Science 224:1121-1124).

In support of this link is evidence that several known proto-oncogenes encode growth factor receptors which couple extracellular protein stimuli (through receptor ligands) with intracellular signal cascades that lead to the synthesis of RNA and DNA necessary for increased cell growth and proliferation. One such proto-oncogene is known as HER2/c-erb B2/neu (hereafter referred to as HER2) which encodes a 185 kD, 1255 amino acid transmembrane receptor (Akiyama, T. et al. (19??) Science 232:1644–1646). The amplification and/or overexpression of HER2 is detected in 11% to 41% of human breast carcinomas (Gullick, W. A. et al. (1991) Brit. J. Cancer 63:434–438), and correlates strongly with increased breast tumor aggressiveness and reduced patient survival (Slamon, D.J. et al. (1987) Science 235:177–182).

The detection of HER2 amplification and/or overexpression in a significant percentage of breast carcinomas as well as the ability of HER2 to act as a potent prognostic factor of both overall and disease-free patient survival, are two compelling arguments in support of continued research on this proto-oncogene. An additional argument stems from recent pre-clinical and clinical evidence that downregulation of HER2 receptor levels by anti-HER2 monoclonal antibodies may have therapeutic value in managing HER2-positive breast cancer patients (Park, J. W. et al. (1991) Genes, Oncogenes, and Hormones: Advances in Cellular and Molecular Biology of Breast Cancer, Dickson, R. B. and Lippman (eds), pp. 193–211). Apart from the limited efficacy that may be anticipated from an antibody-based therapy, recent identification of HER2-positive tumor cells resistant to downregulation by anti-HER2 antibodies (Scott, G. K. et al. (1993) Mol. Cell. Biol. 13:2247–2257) demonstrates the need for a strategy which targets HER2 at the level of the gene rather than at the level of the mature protein.

The HER2 Promoter and Triplex RNA Oligonucleotides

A triplex approach to HER2 downregulation was chosen because of the unique HER2 promoter structure and because of a lack of information on suitable mRNA target sequences. Previous attempts at HER2 downregulation by antisense oligonucleotides were only partially, if at all, successful (Christopher C. Benz & Debu Tripathy, personal communication), and the secondary structure of HER2 has not been sufficiently well characterized to predict accessible mRNA sequences. Therefore, production of an anti-HER2 antisense RNA oligonucleotide was ruled out. Production of an anti-HER2 ribozyme was similarly ruled out both because of a lack of a priori knowledge of susceptible target sequences, as well as because of a necessity of producing a much longer RNA oligonucleotide containing the entire ribozyme.

However, both the sequence and structural/functional elements of the HER2 promoter have been well characterized (Scott, G. K. et al. (1994) J. Biol. Chem. 269: 19848–19858; Ishii, S. et al. (1987) Proc. Natl. Acad. Sci. USA 84: 4374–4378; and Hollywood, D. P. and Hurst, H. C. (1993) EMBO J. 12: 2369–2376) and were uniquely suited for a triplex approach to gene regulation. The critical region of the HER2 promoter has been localized to a 125 base-pair sequence which is capable of conferring a >30-fold variation in HER2 transcriptional activity (Scott, G. K. et al. (1994) J. Biol. Chem. 269: 19848–19858). Within this proximal promoter illustrated in FIG. 10 were several putative protein binding sites (including CAAT, TATA, and a GAGGAA ets-related response element) which surround a 28 base-pair homopurine/homopyrimidine sequence (with 1 central A/T inversion).

Given the structure of the HER2 promoter, should triplex formation occur in vivo, the net result of transcriptional repression could occur through one of several mechanisms. The RNA oligonucleotide could compete directly for binding on the promoter with one or more essential DNA binding transcription factors; the non-triplex-forming 5' or 3' tails of the RNA oligonucleotide could sterically interfere with protein/DNA binding or protein/protein associations; the RNA oligonucleotide could alter duplex rigidity, prevent DNA looping and inhibit association of CAAT and TATA binding proteins; and finally, triplex formation could alter the dimensions of the major and minor grooves and prevent or decrease protein binding on neighboring sites.

While the consensus binding sites illustrated in FIG. 10 did not directly overlap the triplex binding sequence, DNA methylation interference assays on the GAGGAA ets-related response element have demonstrated partial DMS methylation protection upstream to the last few guanines of the triplex target (Scott, G. K. et al. (1994) J. Biol. Chem. 269: 19848–19858). In addition, DNase I protection assays have shown clear footprinting within the triplex binding site (Hollywood, D. P. and Hurst, H. C. (1993) EMBO J. 12: 2369–2376), and a hypersensitivity site within the GAG-GAA response element. Moreover, initial experiments have demonstrated that DNA oligonucleotide-directed triplex formation on the HER2 promoter using a GT purine-rich binding motif could inhibit transcription factor binding to the ets-response element, and that this inhibition was enhanced in the presence of both nucleotide and non-nucleotide 5' "tails" attached to the triplex oligonucleotide. These "tails," were not found to confer increased inhibition through an increase in triplex binding affinity, but more likely through an increase in steric interference at the adjacent ets binding site. Such similar effects could also occur with the RNA 5' and 3' "tails" of U6ON. Finally, a recent report has demonstrated that triplex formation with a DNA oligonucleotide could inhibit transcription from the HER2 promoter in vitro (Ebbinghaus, S. W. et al. (19??) J. Clin. Invest. 92:2433–2439). These findings support the hypothesis that triplex formation on this promoter could mediate HER2 transcriptional repression in vivo.

The U6ON was tested for its ability to downregulate HER2 promoter activity. In the first set of experiments, the activity of the promoter was monitored by expression of a co-transfected reporter chloramphenicol acetyl transferase (CAT) gene to which different HER2 promoters was fused. This bacterial CAT gene is not found within the human genome; therefore, its expression in transfected cells was indicative of a functioning promoter. Two different promoter constructs were tested: the first was the minimal promoter extending 125 base-pairs from the transcriptional start site, and the second was a larger and stronger promoter extending 500 base-pairs from the transcriptional start site. Experiments were performed in both HER2-positive cells (MDA453) and HER2-negative cells (MCF-7). The effect of the anti-HER2 triplex RNA oligonucleotide, U6ON, was then compared with an anti-CAT antisense RNA oligonucleotide, U6AUG. These experiments provided an initial comparison of triplex and antisense data to a common gene.

In the second set of experiments, the activity of the promoter was monitored by examination of endogenous levels of HER2 RNA from 48 to 96 hours after transfection with the chimeric gene for U6ON or control DNA. As HER2 encodes a transmembrane growth factor receptor, RNA isolations were performed in parallel with cell counting to monitor the effect of U6ON on cell growth, and to correlate HER2 mRNA downregulation with growth rate alterations.

A variety of breast cancer cell lines exist which overexpress HER2 to varying extents. The HER2 overexpression can arise from either increased HER2 transcriptional activity or HER2 gene amplification. These phenomena may in fact be causally related, although the exact mechanism through which this might occur has not been clearly delineated.

MDA453 is a prototypical HER2-positive cell line which demonstrates both HER2 overexpression and HER2 gene amplification. These cells are easily transfected by a variety of methods, are relatively homogenous in size and shape, and have previously been demonstrated to be capable of driving transcription from a reporter gene fused to HER2 (Scott, G. K. et al. (1994) J. Biol. Chem. 269:19848–19858). For these reasons they were chosen as a model HER2-positive cell line for testing the effects of RNA oligonucleotides on HER2 promoter activity. MCF-7 cells are also easily transfected, are widely used in breast cancer research, and have previously been shown to be incapable of driving significant transcription from a reporter gene fused to HER2 (Scott, G. K. et al. (1994) J. Biol. Chem. 269:19848–19858). For these reasons they were chosen as a model HER2-negative cell line for testing the effects of RNA oligonucleotides on HER2 promoter activity.

Materials and Methods

Unless otherwise noted the material and methods used in Example 14 are described in the preceding Examples.

Construction of U6AUG

The chimeric gene producing an RNA oligonucleotide referred to as U6AUG was designed as an antisense CAT oligonucleotide to a particularly GC-rich sequence just upstream from the CAT gene stop site. The ATG start site could not be used as an antisense RNA oligonucleotide as it is surrounded by runs of T residues. However, that sequence was used to generate U6mini. The Martinez RNA secondary structure prediction algorithm was implemented to ensure that the GC-rich antisense oligonucleotide did not interfere with the formation of the initial 5' hairpin. Northern blotting with 10 to 20 µg gene transfections in MDA453 cells then confirmed that the RNA oligonucleotide, U6AUG, was indeed abundantly produced, stable, and gave rise to an expression profile similar to that described for U6ON. The sequence of the upper strand of the inserted duplex fragment was:

5' TCGACCGCCCCGCCCTGCCACTCATCG-CAGTACATGCA 3'(SEQ ID NO:5)

The digestion, ligation, and sequencing of this gene was as described in the Examples above.

MCF-7 cell culture

MCF-7 cells were maintained before and after electroporation in DME medium with 1 g/L glucose, supplemented with 10% fetal calf serum, 100 U/ml of penicillin/ streptomycin, and 10 µg/ml insulin at 37° C., 5% $CO_2$.

β-HCG quatitation

Determination of cellular β-HCG was performed 48 hours after MDA453 cell electroporation with 2 µg of the β-HCG gene added to 20 µg of the chimeric oligonucleotide producing gene or promoterless control DNA using the Tandem R total β-HCG immunoradiometric assay (Hybritech, San Diego, Calif.). In this kit, anti-β-HCG antibodies are coupled to plastic beads which are then incubated with the supernatant from transfected cells. A secondary $I^{125}$ radiolabeled anti-β-HCG antibody is then added, and after a 1 hour incubation at 37° C., beads are washed in 0.01% sodium azide and quantitated by a gamma counting.

CAT Assays

Each CAT assay used 10 to 20 µg of the chimeric gene co-transfected by electroporation with 20 µg of the CAT gene and 2 µg of the β-HCG gene per approximately $3 \times 10^6$ cells. Total DNA concentrations were constant for all electroporations by supplementing where necessary with promoterless plasmid DNA. Cells were harvested 48 hours after transfection by freeze thaw lysis in 100 mM Tris, pH 7.6, 2% Triton X. Cell lysates were then collected and microcentrifuged (12,000 xg) for 10 min at 4° C., and supernatants were heated to 65° C. for 10 min to inactivate cellular proteases. Each sample was then overlaid with 100 mM Tris, pH 7.6, 1 mM chloramphenicol (Sigma), and 1 µCi of [$^3$H]-acetyl coenzyme A (Dupont/NEN Research Products), followed by the addition of 5 ml of Econofluor water immiscible scintillation fluid (Dupont/NEN Research Products). Samples were immediately scintillation counted for 1 min to obtain baseline values, followed by incubation at 37° C. and counting at regular intervals (20–30 min) for 2 to 3 hours. CAT activity values were obtained by normalizing the slope of counts vs. time for each sample with corresponding β-HCG values obtained as described above.

Effect of RNA oligonucleotides on HER2-driven CAT Expression

Figure 11A:
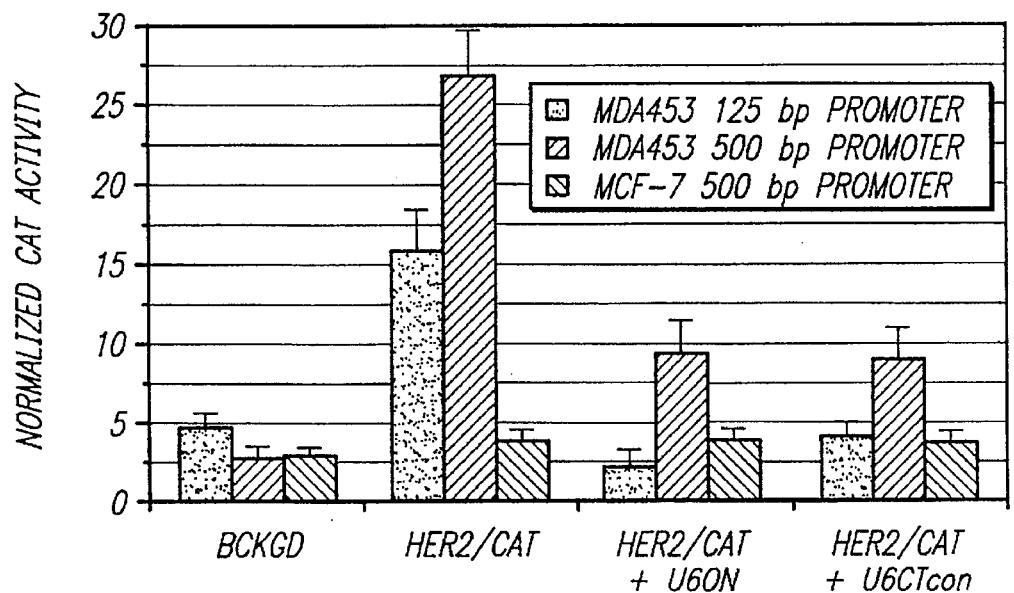
FIG. 11A illustrates the CAT activity arising from the minimal 125 bp HER2 promoter and the stronger 500 bp HER2 promoter in MDA453 and MCF-7 cells 48 hours after co-transfection with 20 μg of either U6ON or U6CTcon. Promoterless plasmid DNA was used to equalize DNA concentrations. Both U6ON and U6CTcon RNA oligonucleotides demonstrated virtually 100% downregulation of the minimal promoter and roughly 65 to 70% downregulation of the stronger 500 bp promoter.

FIG. 11A illustrates the CAT activity arising from the minimal 125 bp HER2 promoter and the stronger 500 bp HER2 promoter in MDA453 and MCF-7 cells 48 hours after co-transfection with 20 µg of either U6ON or U6CTcon. Promoterless plasmid DNA was used to equalize DNA concentrations. Both U6ON and U6CTcon RNA oligonucleotides demonstrated virtually 100% downregulation of the minimal promoter and roughly 65 to 70% downregulation of the stronger 500 bp promoter. As expected, no CAT activity was found in MCF-7 cells in either the presence or absence of RNA oligonucleotides. Interestingly, β-HCG levels, which were used to normalize cell populations for transfection efficiency were not similarly downregulated. Thus, the HER2/CAT downregulation cannot be attributed to a general downregulation of protein synthesis. Successive repetitions of this CAT assay using these two chimeric gene constructs with the 500 bp promoter have produced similar patterns of downregulation (ranging from roughly 45% to 75%).

Figure 11B:
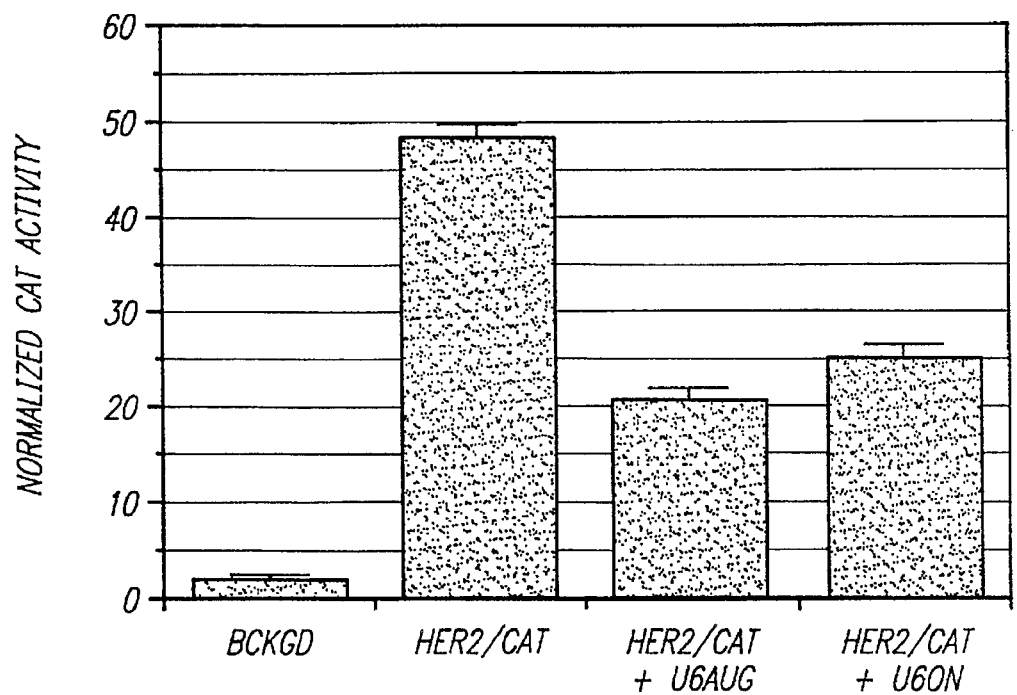
FIG. 11B illustrates the HER2/CAT downregulation of the stronger 500 bp promoter by triplex and antisense RNA oligonucleotides after co-transfection with 10 μg of either U6ON or U6AUG.

FIG. 11B compares HER2/CAT downregulation of the stronger 500 bp promoter by triplex and antisense RNA oligonucleotides after co-transfection with 10 µg of either U6ON or U6AUG. The antisense RNA oligonucleotide produced 57% downregulation whereas the U6ON produced 49% downregulation. Successive repetitions of this CAT assay have demonstrated similar patterns of downregulation. While absolute levels vary, in each case the antisense RNA oligonucleotide continually demonstrates 5 to 15% greater downregulation than the triplex RNA oligonucleotide. As proper controls are still lacking, the significance of these observations has yet to be determined.

Figure 12A:
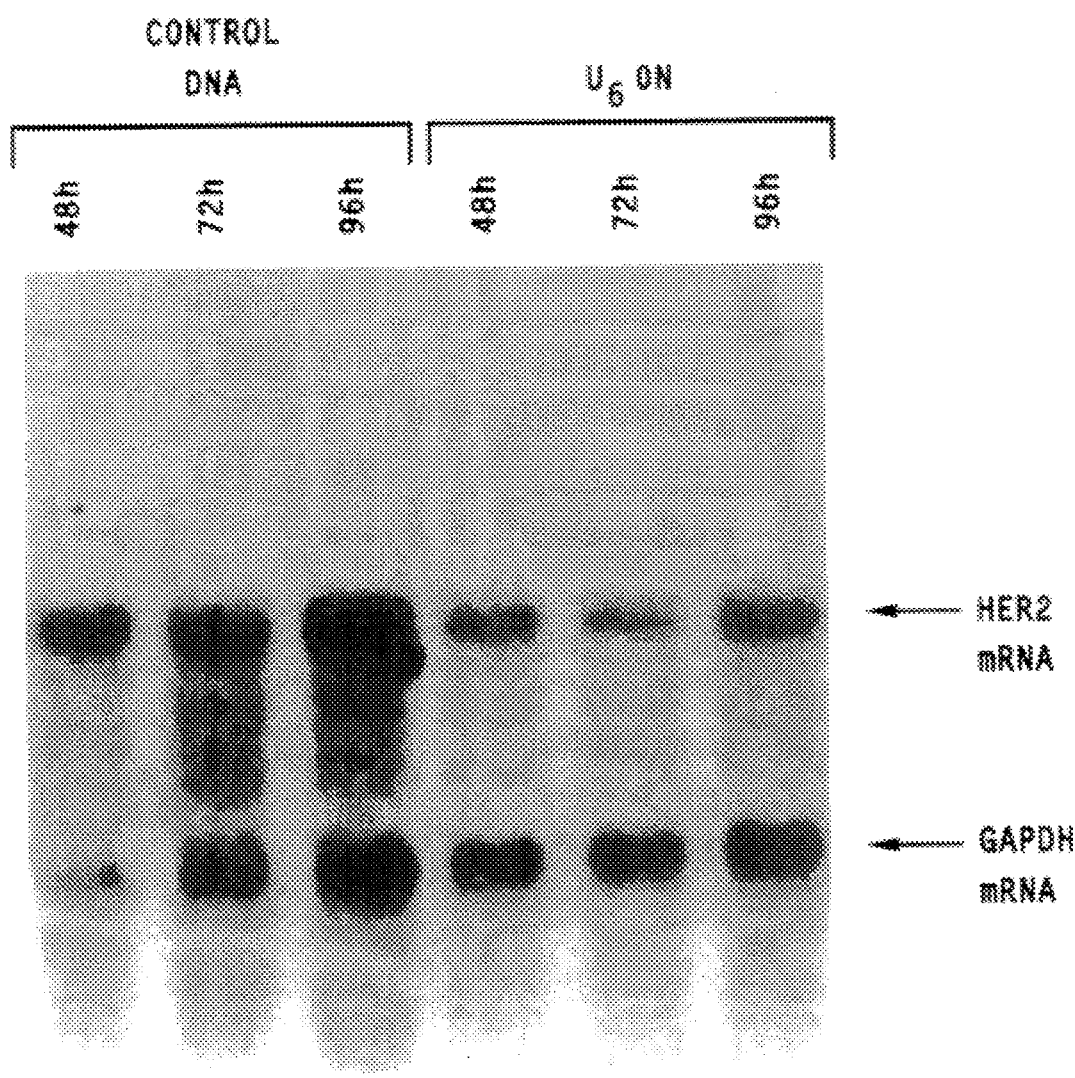
FIG. 12A is a Northern blot, which compares the levels GAPDH and HER2 RNA from 48 to 96 hours after transfection with the U6ON oligonucleotide generator, as compared with control DNA.
Figure 12B:
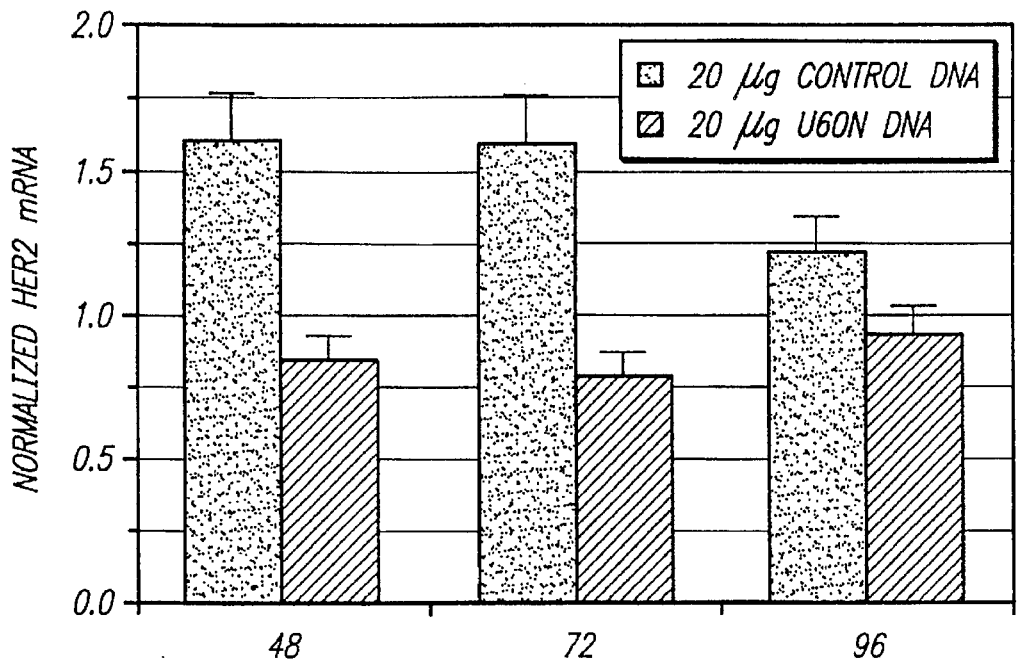
FIG. 12B is a graph demonstrating the HER2 RNA values from FIG. 12A after normalization for the GAPDH levels.
Figure 12D:
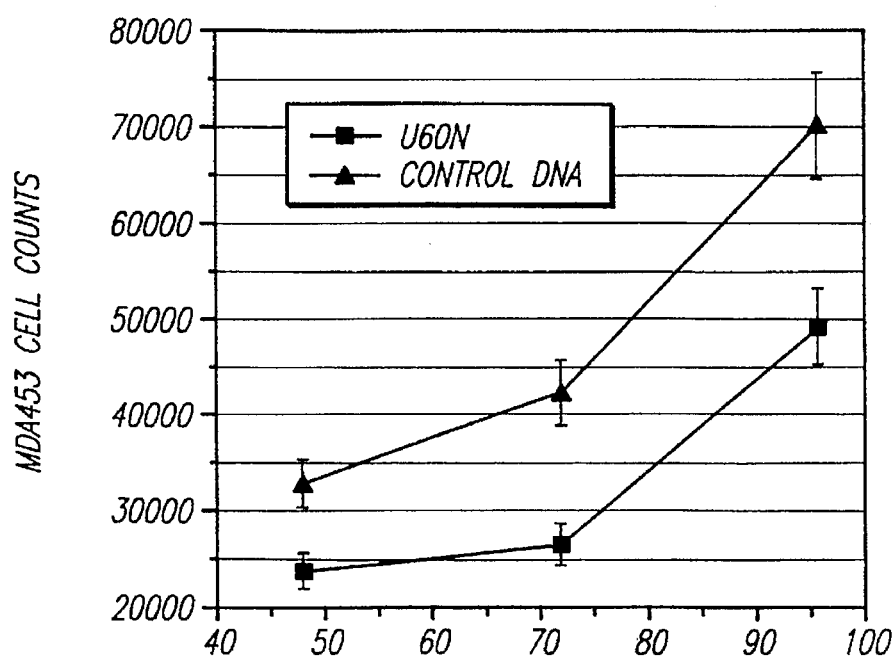
FIG. 12D demonstrates the cell growth rate in U6ON transfected cells versus control cells between 48 hours and 96 hours.

FIG. 12 illustrates the effect of U6ON on endogenous levels of HER2 mRNA and cell growth in MDA453 cells. As seen from the Northern blot (FIG. 12A), GAPDH levels are not significantly altered by the presence of the RNA oligonucleotide from 48 to 96 hours after gene transfection. Note also that no indication of unspliced GAPDH or HER2 could be detected despite a 20 µg gene transfection, suggesting that U6 was present and functioning within the spliceosome. However, after normalization with GAPDH levels, a relative decrease in HER2 levels was seen in the U6ON transfected cells when compared to cells transfected with equal amounts of promoterless plasmid DNA (FIG. 12B). This decrease in HER2 RNA was most prominent at 48 hours (47.5% downregulation) and 72 hours (50.8% downregulation), but declines in significance at 96 hours (24.1% downregulation). Given the long $t_{1/2}$ of intracellular HER2 mRNA (roughly 24 hours), complete promoter shut down immediately upon transfection could only lead to a maximum of 75% downregulation. Thus, the nearly 50% downregulation at 48 hours indicated that initially, the promoter was operating at only one-third of its normal rate.

This pattern of high HER2 downregulation at 48 hours and 72 hours and low HER2 downregulation at 96 hours HER2 was reflective of the corresponding decline in intracellular U6ON levels at 48 h, 72 h, and 96 hours shown in the Northern blot of FIG. 12C. As demonstrated in FIG. 6B, a 20 μg U6ON transfection in MDA453 cells lead to nearly equal levels of U6 and U6ON at 48 hours post-transfection, with U6 slightly reduced from normal levels. Earlier rough calculations estimated an intracellular U6ON concentration of $5 \times 10^5$ copies of U6ON/cell leading to an intranuclear U6ON concentration of 1.6 mM. That such mass accumulation of an RNA oligonucleotide within the nucleus appears to affect the production of HER2 without affecting the production of GAPDH demonstrates a degree of specificity of U6ON. Cell counts obtained in parallel with RNA isolations (FIG. 12D) showed a corresponding decrease in cell growth in U6ON transfected cells versus control cells between 48 hours and 72 hours (11.7% versus 28.8%), but a rebound in growth rate between 72 hours and 96 hours (85% versus 65%).

Example 15

Effect of Intracellular RNA Oligonucleotides on Native U6 Levels: Evidence that U6 Transcription and Capping are Uncoupled In Vivo The effect of producing high concentrations (160 μM to 16 mM) of intranuclear RNA oligonucleotides generated from a plasmid bearing the regulatory promoter, capping, and termination sequences of the human U6 gene on native U6 RNA levels was studied. Native U6 RNA levels were unaffected by transfections of up to 20 μg of the chimeric oligonucleotide-producing gene, but U6 RNA levels decreased substantially after transfections of 20 μg to 40 μg of the chimeric gene. These effects were seen within 24 hours after gene transfection and persisted unchanged up to 48 hours after gene transfection. U6 RNA levels returned to native levels after 72 to 96 hours. These decreases in U6 RNA were determined to result primarily from a decrease in U6 RNA stability rather than a decrease in U6 RNA production. U6 RNA stability was found to be titratable in the presence of increasing levels of stable RNA oligonucleotides bearing a 5' γ-monomethyl phosphate cap, but were normal and unchanged for unstable RNA oligonucleotides whose secondary structure may inhibit capping. These results on U6 RNA differential stability in the presence of capped RNA oligonucleotides strongly suggest that in vivo transcription and capping are uncoupled for U6 RNA.

Short, sequence-specific RNA oligonucleotides can be generated in high yield within the cell nucleus using an expression system derived from the U6 gene. As the U6 gene requires only upstream elements for initiation and elongation by RNA Polymerase III, and stops cleanly upon reaching a string of 4 or more thymine residues (Kunkel G, et al. (1986) Proc. Natl. Acad. Sci. 83:8575–8579; Reddy R, et al. (1987) J. Biol Chem. 262:75–81; Kunkel G and Pederson T. (1989) Nuc. Acids Res. 17:7371–7379), its internal sequence can be removed and be replaced by an oligonucleotide sequence designed to target cellular DNA or RNA. In addition, the retention of an initial native U6 hairpin and the majority of an adjacent hexameric sequence will allow for efficient 5' γ-monomethyl phosphate capping (Singh, R. and Reddy, R. (1989) Proc. Natl. Acad. Sci. USA 86:8280'8283; Singh, R. et al. (1990) Mol. Cell. Biol. 10:939–946). As all of the regulatory elements of U6 are retained in the chimeric oligonucleotide-producing gene, one could expect that as the quantity of gene transfected is increased, one or more of the regulatory elements of U6 would come under limiting supply. The experiments of this section seek to determine which of these elements is most limiting, and at what transfected gene dose this element becomes limiting.

U6 is a unique mammalian gene as it appears to represent an intermediate between standard class II genes and class III genes (Dahlberg, J. E. and Lund, E. (1992) Science 254:1462–1463). U6 is transcribed by RNA polymerase III and stops at runs of thymines; however, unlike almost all other class III genes, it contains no functional internal control region. While there is a region within the gene with homology to the "box A" sequence of other class III genes, it is either vestigial or coincidental since it can be deleted without loss of wild type expression (Kunkel, G. and Pederson, T. (1989) Nuc. Acids Res. 17:7371–7379). In addition, like standard class II genes, the U6 promoter contains a TATA box (located at position −30) which is essential for promoter activity. Interestingly, the exact location of this TATA box is slightly altered with respect to the position of class II gene TATA boxes, and alteration of this U6 TATA box converts the gene from a class III gene to a class II gene (Lobo, S. M. and Hernandez, N. (1989) Cell 58:55–67). As in class II and class III genes, as well as class I genes, U6 transcription requires a TATA box binding factor (TBP) (Rigby, P. W. (1993) Cell 72:7–10). This factor is a subunit within the transcription factor TFIIIB also essential for initiation.

In addition to RNA polymerase III and TFIIIB, U6 transcription requires an as yet unpurified factor referred to as the proximal sequence element binding factor (PBP) which binds strongly to a highly conserved element adjacent to the TATA box (located at −60). This element has been shown to confer species specificity to the U6 gene, as well as to ensure initiation at the proper starting nucleotide (Simmen, K. A. et al. (1992) J. Mol. Biol. 223:873–884; and Goomer, R. S. and Kunkel, G. R. (1992) Nuc. Acids Res. 20:4903–4912). The last known promoter element necessary for efficient U6 transcription is referred to as the distal control region (DCR) which resides at roughly −244 to −149 and contains binding sites for the transcription activator Oct1 (Danzeiser, D. A. et al. (1993) Mol. Cell. Biol. 13:4670–4678). Two other transcription factors, TFIID and TFIIA have been shown to stimulate U6 expression in vitro, but their roles in in vivo U6 expression have not been elucidated (Simmen, K. A. et al. (1991) EMBO J. 10:1853–1862). All of these U6 promoter elements are also found in the promoter of the chimeric oligonucleotide-producing gene, and all of these factors are expected to play identical roles in the initiation and elongation of the RNA oligonucleotide.

Figure 13:
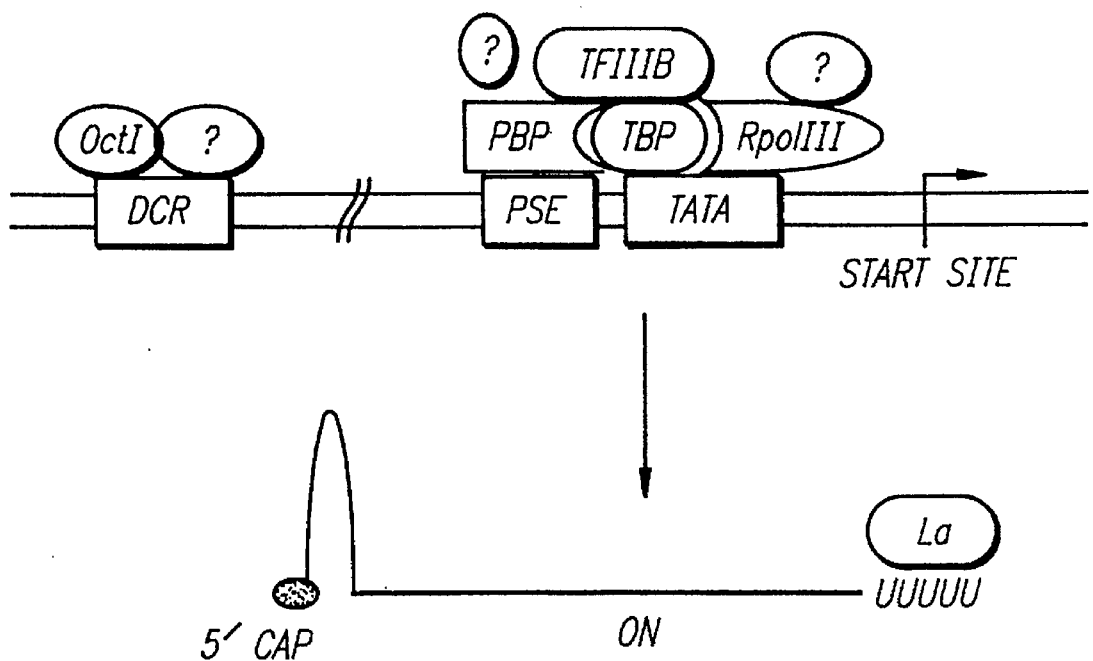
FIG. 13 is a diagram detailing the promoter, termination, and capping factors of the chimeric gene (oligonucleotide generator). This drawing illustrates schematically a possible configurations of the needed transcriptional factors of both the U6 gene and the chimeric RNA-oligonucleotide producing gene.

The chimeric gene also shares the initial 25 nucleotides and adjacent hexameric sequence (with 1 C to A mismatch at base position 24) and potential for 5' capping with the U6 gene. Thus, both the recently purified capping enzyme (Shimba, S. and Reddy, R. (1994) J. Biol. Chem. 269:12419–12423) and the capping substrate(s) are expected to function identically for both genes. A final shared element is the Lupus-associated (La) antigen (Rinke, J. and Steitz, J. (1982) Cell 49:149–159). This 55 kD protein has been shown to bind transiently to the uridine-rich tail of U6. It may function to protect the 3' end of nascent transcripts from nuclease degradation, or to participate in 3' post-transcriptional modifications such as the addition of uridine residues and a terminal 2'-3' cyclic phosphate (Lund, E. and Dahlberg, J. E. Science 255:327–330). Regardless of activity, it may be expected to function in both nascent U6 as well as nascent RNA oligonucleotides. A summary of the factors shared by both genes and/or transcripts is provided in FIG. 13.

As the entire U6 sequence from +26 to +87 was deleted in creating the chimeric oligonucleotide-producing gene, putative catalytic elements and U4 and U2 hybridization regions within this deleted sequence are not found within the RNA oligonucleotide (Datta, B. and Weiner, A. M. Nature 352:821–824; and Sontheimer, E. J. and Steitz, J. A. (1993) Science 262:1989–1996). As these elements are essential for U6 splicing activity within the splicing apparatus, neither splicing nor association with U2 or U4 are expected with the RNA oligonucleotide.

By monitoring U6 RNA levels and U6 RNA stability in the presence and absence of both the capped (U6ON) and the presumably non-capped (U6AS) RNA oligonucleotides, information was obtained on the dose-dependent effects of RNA oligonucleotide production. At ≧20 µg of transfected chimeric U6ON gene, a dose-dependent decrease in total U6 RNA levels was observed. This decrease was attributed primarily to a decrease in U6 RNA stability rather than a decrease in U6 production as no decrease in U6 RNA levels was found upon transfection with ≧20 µg of the chimeric U6AS gene. U6 stability has previously been described as resulting from the nuclease-resistant 5' cap and the extensive 3' hybridizations (Terns, M. P. et al. (1993) Genes and Devt. 7:1898–1908). Since U6ON can be 5' capped but cannot hybridize with itself or with, competition for capping enzymes and/or cofactors is assumed, and the 5' capping apparatus is deemed the factor in most limiting supply.

Figure 16:
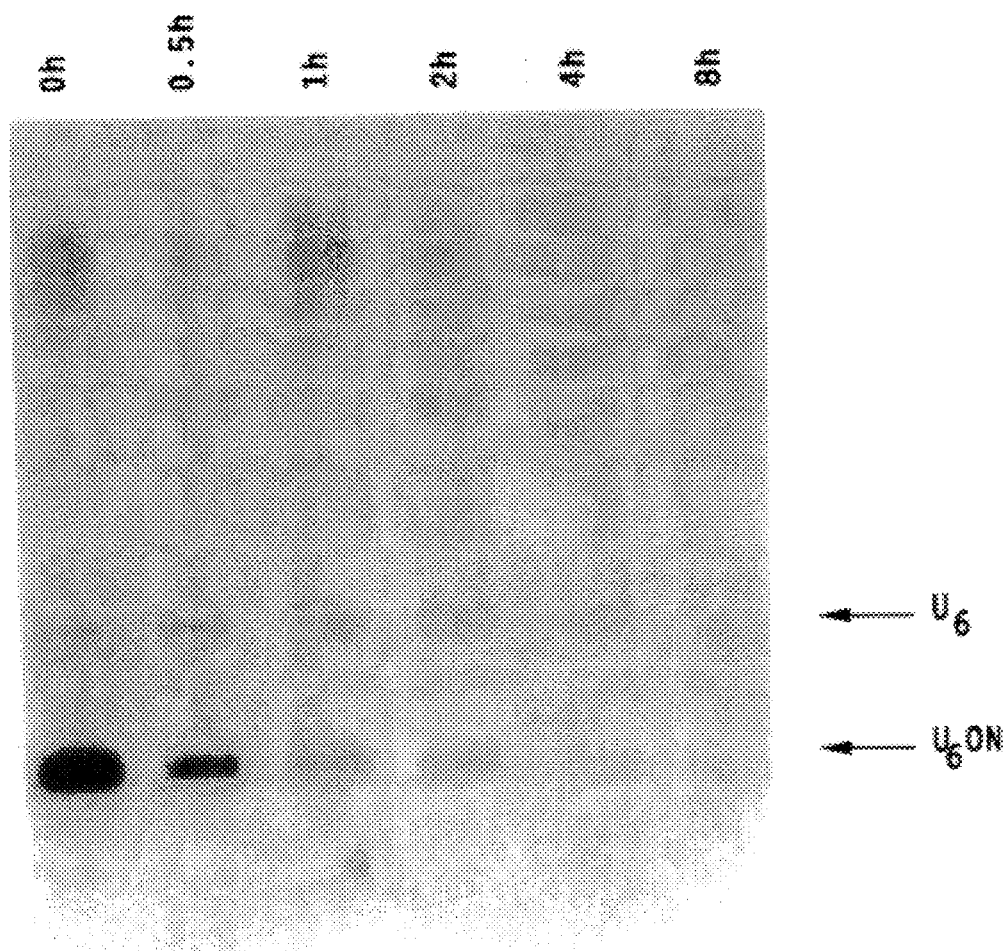
FIG. 16 is a half-tone reproduction of a Northern blot, demonstrating that U6ON can downregulate U6 stability. 293 cells were transfected with 20 μg of the chimeric gene for U6ON followed 48 hours later by 10 μg/ml treatment with Actinomycin D to mediate total transcription arrest. RNA isolations followed at 0 hour, 0.5 hour, 1 hour, 2 hour, 4 hour, and 8 hour time points followed by Northern blotting.

The most likely explanation—that the capping apparatus was saturated and thus RNA stability is reduced at high levels of U6ON gene transfection, but not at high levels of U6AS gene transfection—was tested by examining the half-life, $t_{1/2}$, of U6 RNA in the presence of U6ON. FIG. 16 illustrates the dramatic reduction in $t_{1/2}$ seen 48 hours after a 20 µg U6ON gene transfection followed by transcription arrest by Actinomycin D in 293 cells. The normal $t_{1/2}$ value for U6 has previously been determined to range from 16 to 24 hours. The $t_{1/2}$ value estimated after scanning densitometry of this Northern blot was roughly 3 hours. A similar dramatic decrease in U6 stability (9-fold) has previously been reported in characterizing capped vs. non-capped in vitro generated U6 RNA after microinjection into Xenopus oocytes (Shumyatsky, G. et al. (1993) Nucleic Acids Res 21: 4756–4761).

Materials and Methods

All relevant details on cells and cell culture, electroporation, transcription arrest, RNA isolation, Northern blotting, and secondary structure prediction are described in the Examples above. The capped intracellular RNA oligonucleotide consists of the same CU-rich sequence referred to as U6ON. The non-capped intracellular RNA oligonucleotide consists of the same mixed nucleotide sequence as that used in FIG. 9 and is similarly referred to as U6AS. The following Method is pertinent to Example 15 in particular.

Dynamical Modeling of U6 and U6ON

Simple linear first and second order differential equations were derived to describe the expression of both U6 and U6ON, and dynamical simulations were performed using the modelling program STELLA (High Performance Systems, Hanover, N.H.). In these models, steady-state values of RNA levels were assumed to be a function of only two variables, production (i.e., from transcription) and decay (i.e., from nuclease degradation). Production, P, was assumed to be a function of the initiation rate constant, $K_i$, and gene copy number, gcn, and the decay rate constant $K_d$, was determined from the experimentally derived values of $t_{1/2}$, assuming a first order model of degradation.

$$d[U6]/dt = K_i*gcn - K_d*[U6] = P - K_d*[U6]$$

$$d[U6ON]/dt = K_i*gcn - K_d*[U6ON]$$

For both U6 and U6ON, the initiation rate constant, $K_i$ was assumed to be constant and to represent constitutive transcription. The rate of elongation was eliminated from these models as the process of initiation was assumed to be the rate limiting step in transcription. Thus, the rate of initiation was assumed to represent the rate of production of a single complete U6 or U6ON RNA molecule from its genomic template. For U6, the gene copy number, and thus P was held constant, whereas for U6ON, the gene copy number was assumed to be directly coupled and vary linearly with gene transfection dose. Initial values of U6ON were set to 0 and initial values of U6 were set to the normal value of $0.5 \times 10^6$ copies/cell. U6 gene expression was assumed to be equally present in 100% of the cell population and to be unaffected by the physical process of electroporation. Electroporation was assumed to result in U6ON gene expression with a transfection efficiency of 70% of the cell population. Differential equations were solved by Euler's method.

Results

Figure 14B:
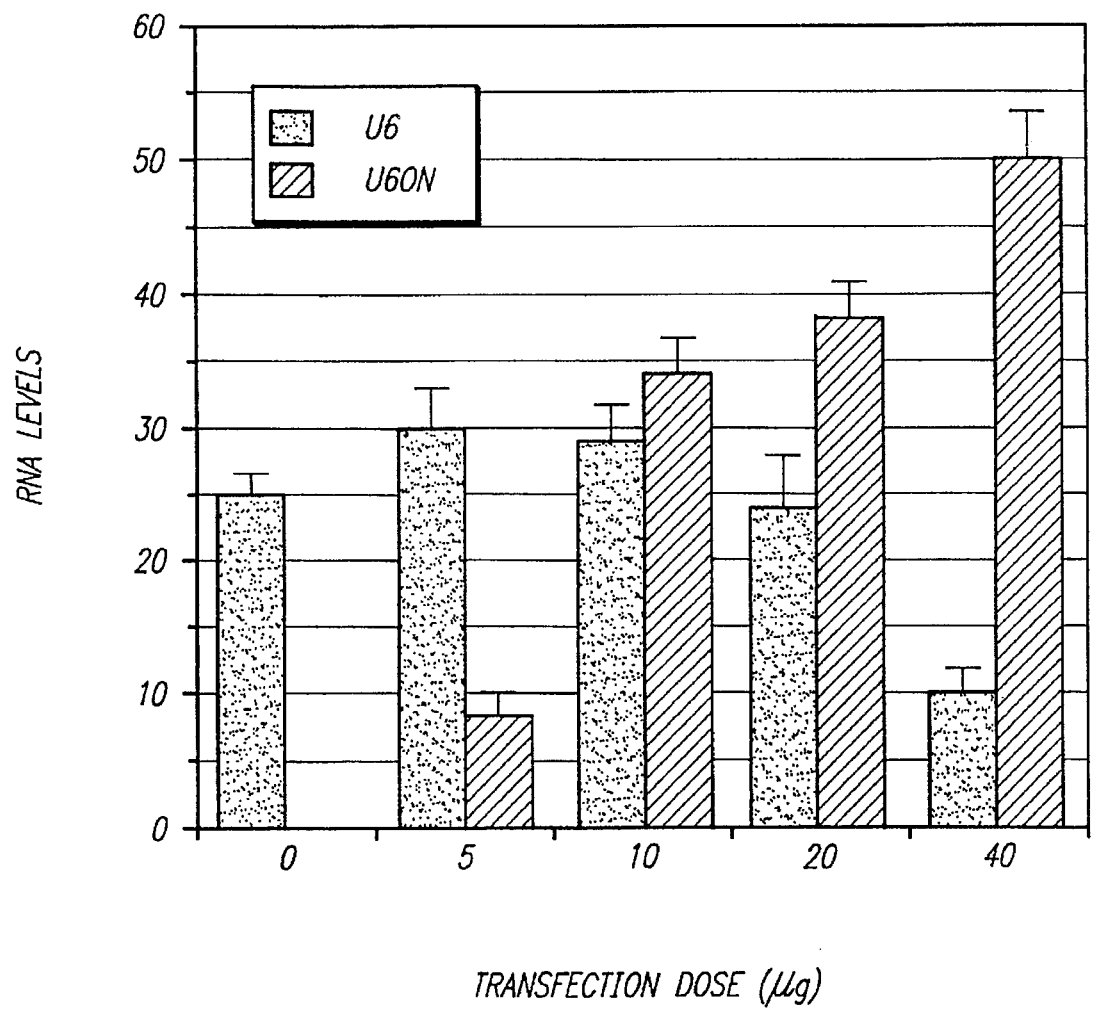
FIG. 14 is a half-tone reproduction of a Northern blot and a graph which demonstrate the dose dependence of gene transfection on U6 and U6ON in 293 cells. Cells were transfected with 40 μg of DNA which contained 5 to 40 μg of the chimeric gene or promoterless plasmid DNA. RNA was isolated 48 hours after transfection. After Northern blotting with U6 and U6ON probes (FIG. 14A), densitometry was performed to quantitate the relative downregulation of U6 with concurrent upregulation of U6ON and the data was presented in FIG. 14B. Error bars arise from standard deviation of densitometry data and slight inequalities in RNA loading, normalized by ethidium bromide staining.

FIG. 14A and 14B demonstrate the effect of increasing quantities of the transfected gene for U6ON in human 293 cells. Results demonstrate that the levels of U6 RNA remain relatively constant up to 10 to 20 µg transfection doses, but cause a decrease in U6 RNA levels at transfection doses of 20 to 40 µg. The RNA in each case was isolated 48 hours after electroporation; however, isolation at 24 hours also produced identical trends of U6ON upregulation with concurrent U6 downregulation.

Example 13 presented evidence that the sequence of the inserted oligonucleotide can effect the stability of the resulting intracellular RNA transcript by interfering with formation of an initial hairpin and disrupting the necessary signal for capping (FIGS. 9A and 9B). Several genes were designed to contain this interfering oligonucleotide sequence, the prototype of which was termed U6AS. The generation of this unstable U6AS transcript was used to determine whether this dose-dependent decrease in total U6 RNA levels was a result of a decrease in production (i.e., saturation of a requisite transcription factor or polymerase) or an increase in degradation (i.e., greater accessibility to exonucleases and/or endonucleases).

Figure 15:
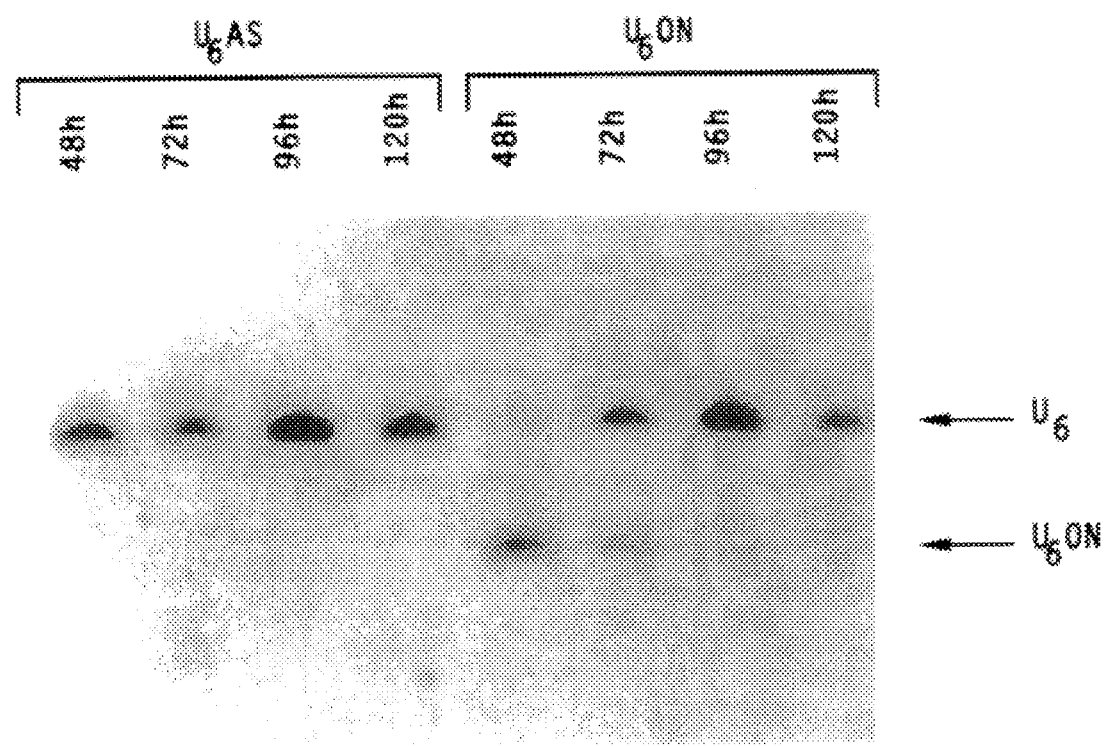
FIG. 15 is a half-tone reproduction of a Northern blot, demonstrating that U6 levels vary as a function of RNA oligonucleotide stability. 293 cells were treated with 20 μg of the gene for U6AS (lanes 1–4) or U6ON (lanes 5 to 8) followed by RNA isolation at 48 hour, 72 hour, 96 hour, and 120 hours time points. U6AS has previously been shown to be an unstable RNA oligonucleotide while U6ON has been shown to be a stable and 5' capped RNA oligonucleotide.

FIG. 15 illustrates the differences in U6 RNA profiles 48 hours to 120 hours after transfection with 20 µg of either the U6AS gene or the U6ON gene in 293 cells. (The pattern was also verified with another stable RNA oligonucleotide, U6CTcon.) Whereas U6 RNA levels remained relatively unaffected by the presence of the unstable and presumed non-capped U6AS, U6 RNA levels were drastically reduced and then rebound in the presence of the stable capped U6ON. Given that U6AS and U6ON differ only in the 28 nucleotide internal oligonucleotide sequence and their ability to retain the initial 5' hairpin needed for capping, not in the upstream promoter or termination signals, saturation of transcription factors, RNA polymerase III, the La antigen, or the poorly characterized post-transcriptional modification apparatus were unlikely as an explanations for the disparity in U6 levels.

Figure 17:
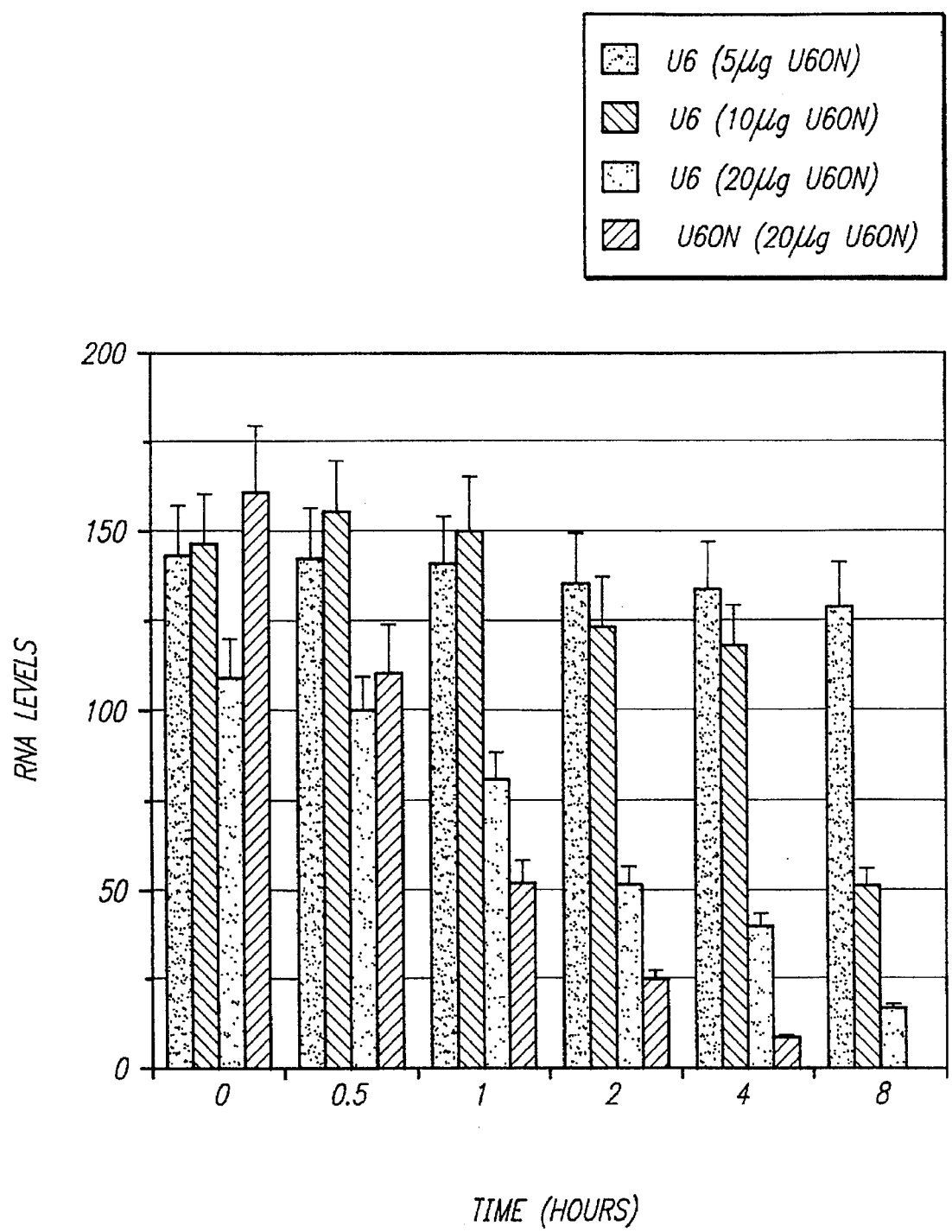
FIG. 17 is a graph demonstrating that U6 stability is titratable by U6ON levels. The experiment presented in FIG. 16 was repeated using 10 μg and 5 μg chimeric gene transfection doses. After performing individual Northern blots, data was amassed and quantitated by densitometry.

FIG. 17 demonstrates graphically the profiles of U6 degradation as U6ON gene transfection doses were reduced from 20 µg down to 5 µg. As the dose was lowered, the U6 RNA stability increased to its native level, consistent with the trends presented in FIG. 14. The stability of U6ON after a 20 μg gene transfection dose was shown in the graph, but similar profiles were seen after 10 μg and 5 μg gene transfections. No effect on normal U6 RNA stability was seen 48 hours after a 20 μg U6AS gene transfection. Transcription arrests were not carried out for time points longer than 8 hours to avoid significant artifacts due to cellular dysfunction (such as reduced levels of cellular nucleases) as a result of the Actinomycin D treatment.

FIG. 18 demonstrates the simulated output of U6 and U6ON given different parameters of decay rate constant (derived from different $t_{1/2}$ values) and gene copy number (derived from transfection dose). While these models were highly simplified, they corroborate previously determined experimental parameters of U6ON expression; they provided broad estimates as to the gene copy number of both the human U6 gene and the electroporated U6ON gene, and their rates of transcription initiation; and they gave schematic representation to the effect of large quantities of U6ON upon U6.

Figure 18A:
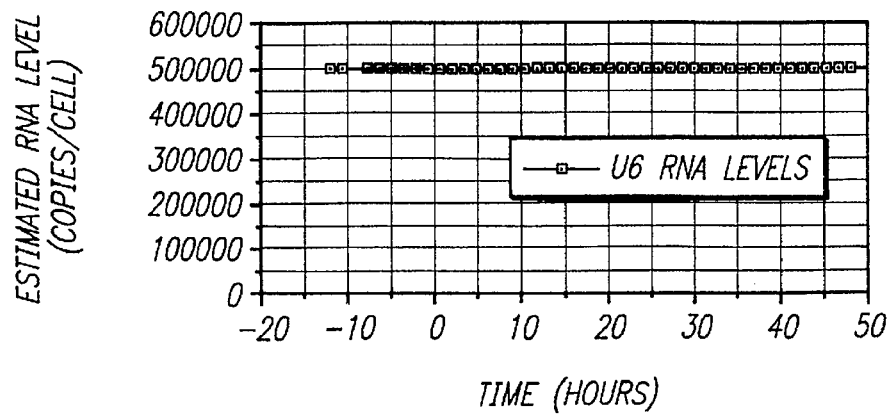
FIG. 18A shows steady-state levels of U6 expression.

In FIG. 18A, the steady-state production of U6 is displayed. This RNA has previously been demonstrated to be present at roughly $0.5 \times 10^6$ copies/cell with a $t_{1/2}$ value of roughly 24 hours. Using these values, a production flow rate, P, of 4 transcripts/second was derived. The exact copy number of the human U6 gene was not known explicitly due to the presence of many pseudogenes, but was estimated to range between 2 and 10 based on comparisons with other species (Saluz, H. et al. (1988) Nuc. Acids Res. 16: 3582; and Das, G. et al. (1987) J. Biol. Chem. 262: 1187–1193). This lead to an estimate of transcription initiation rate, $K_i$, of 0.4 to 2 initiations/second/gene copy. As the contribution to transcript production by elongation was assumed negligible, $K_i$ estimations referred to the rate of production of a completed full length transcript from a single gene copy. These $K_i$ estimations were reasonably consistent with those previously made for the U1 and U2 genes, present in similar intranuclear concentrations with similar $t_{1/2}$ values (Dahlberg, J. E. and Lund, E. (1988) Structure and function of major and minor small nuclear ribonucleoprotein particles, Springer-verlag, Berlin).

Figure 18B:
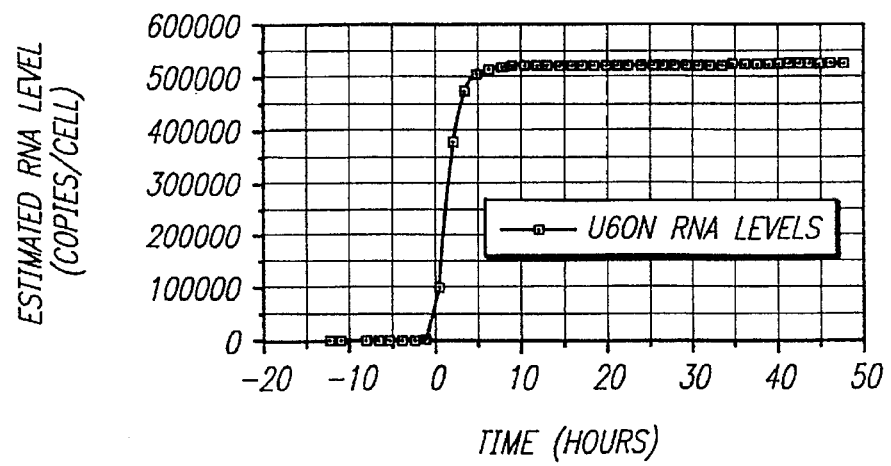
FIG. 18B shows transient and steady-state levels of U6ON expression.

In FIG. 18B, the profile of U6ON expression after a 20 μg gene transfection was depicted using $K_d$ and $K_i^*gcn$ values experimentally derived in Example 14 from production rates (FIG. 7A) and $t_{1/2}$ values (FIG. 7B), respectively. Implementing these parameters and simulating production for 48 hours produces a steady-state production levels very similar to that shown in Example 10 (FIG. 5B) i.e. slightly above U6 levels. Here, the $K_i^*gcn$ value was roughly 100. If constitutive expression is assumed, $K_i$ was identical for U6 and U6ON, and therefore 0.4 to 2 initiations/second/gene copy. This lead to an estimation of 50 to 250 functional U6ON-producing genes/cell after transfection in the electropotation conditions described above.

Figure 18C:
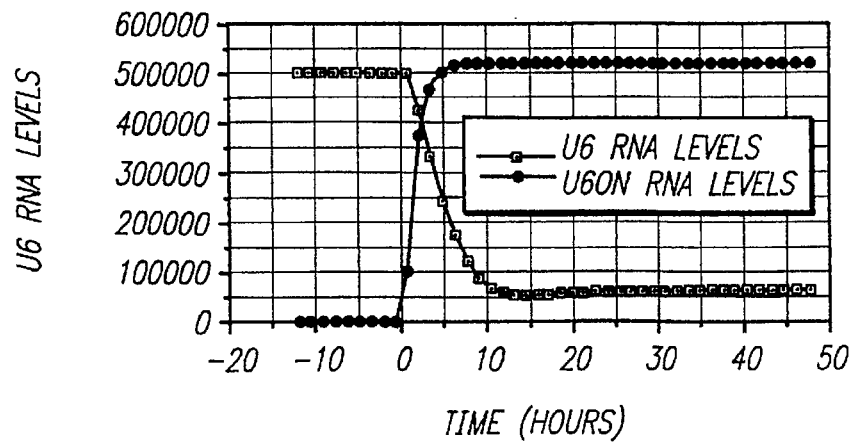
FIG. 18C shows transient and steady-state levels of expression of U6 after reduction of transcript stability by U6ON production.

In FIG. 18C, the profile of U6 expression following transfection with 20 μg of the U6ON-producing gene was plotted. The effect of production of U6ON on U6 RNA was modeled as a first order exponential smoothed step function of degradation from an initial value derived from a 24 hour $t_{1/2}$ to a final value derived from a 3 hour $t_{1/2}$. As expected, upon transfection, U6 RNA levels dropped by a factor of 8, and the subsequent U6 expression profile demonstrated a second order appearance (illustrated by slight overshoot at 12 h). In addition, the experimental observation that this new steady-state value was reached by 24 hours is consistent with this model. The reduction in U6 RNA levels modeled solely by the impact of reduced RNA stability, in comparison with the experimentally-derived observations presented in this and previous Examples, support further the notion that reduced U6 RNA stems primarily from reduced stability rather than reduced production.

From the results presented above, several important conclusions can be drawn. Firstly, upon transfection with ≧20 μg of a gene for stable (capped) RNA oligonucleotides, total U6 RNA levels were decreased. Secondly, this decrease in U6 RNA could be attributed primarily to a decrease in RNA stability rather than a decrease in RNA production. Thirdly, a saturation of capping enzymes and/or cofactors with subsequent production of uncapped U6 RNA was the most likely explanation for the decrease in U6 RNA stability. Finally, these conclusions taken together support the inference that transcription and capping are uncoupled in the U6 gene.

The observation of decreased levels of U6 RNA 24 to 48 hours after transfection with ≧20 μg of the chimeric U6ON-producing gene placed a clear upper limit on the gene dosage above which cells were affected by the production of the stable RNA oligonucleotide. This 20 μg value was estimated in two unrelated cell lines, 293 and MDA453, suggesting that the type of cell transfected probably did not play a large role in defining this upper limit. However, the conditions of electroporation (i.e., the voltage and capacitance that sets the dimensions of the electrical pulse) would be expected to play a large role. In these experiments, a setting of 250 V, 960 μF led to a cell survival rate post-electroporation of roughly 40 to 60%. At higher voltage settings, the survival percentage would be reduced, but those surviving might contain higher doses of transfected gene, leading to possible reductions of U6 RNA levels at lower than 20 μg doses.

Several lines of evidence lead to the conclusion that the reduction in U6 RNA was a result of decreased RNA stability rather than decreased RNA production. In strongest support is the finding of dramatically reduced U6 RNA $t_{1/2}$ in the presence of a high concentrations of U6ON. Thus, a decrease in U6 RNA must play a role in overall decreased levels, but does it play the primary role? The observation that U6 RNA levels were not reduced in the presence of similar transfection doses with a gene for an unstable RNA oligonucleotide lends additional support to the above hypothesis. Given all previous evidence of needing only upstream U6 promoter sequences and downstream termination sequences for proper initiation and termination of transcription, one can assume that the unstable RNA oligonucleotide (U6AS) was generated equally as often and used the same transcription factors as the stable RNA oligonucleotide (U6ON). Given equal gene copy numbers of U6AS and U6ON, each should have bound to the same amount of transcription factors if there existed no system of negative feedback control for U6. To date, no such regulatory system has been described.

Saturation of the capping apparatus appears the most likely cause of decreased total U6 RNA in the presence of abundant levels of capped U6ON RNA. U6 RNA stability has previously been attributed primarily to its 5' cap and its substantial 3' hybridizations. Since U6ON contains no regions amenable to self or U4 hybridizations, but does obtain the 5' cap, the dramatic decrease in U6 stability should therefore resulted from the loss of the 5' cap. In further support, evidence of an 8- to 9-fold loss of U6 RNA stability has previously been reported for intracellular non-capped U6 by two independent laboratories (Terns, M. P. et al. (1993) Genes and Devt. 7: 1898–1908; and Shumyatsky, G. et al. (1993) Nuc. Acids Res. 21:4756–4761). This reduction corresponded well to the 8-fold decrease in U6 RNA $t_{1/2}$ seen upon production of high concentrations of U6ON. Therefore, if the above two properties are indeed primarily responsible for the 24 hour $t_{1/2}$ of U6 RNA, the contribution of extensive hybridization with self and U4 RNA to the stability of native U6 RNA can be estimated as roughly 3-fold.

To date, all other known capped RNA (including mRNA and other small nuclear U-rich RNA such as U1, U2, etc.) are thought to have transcription coupled to capping (Reddy R. et al. (1992) Pharm Ther. 54: 249–267). If this U6 RNA with reduced stability does represent non-capped U6, this finding demonstrates for the first time in vivo (and corroborates observations in vitro (Gupta et al. (1990) J. Biol. Chem. 265: 9491–9495) that transcription and capping are uniquely uncoupled for the U6 gene.

Example 16

Effect of Intracellular RNA Oligonucleotides On General Properties of Transcription and Translation The effect of U6ON expression on 7SK, U1, U3, and GAPDH RNA levels and β-HCG protein levels was studied to make an initial assessment of possible toxic effects of the chimeric oligonucleotide-producing gene on cellular transcription and translation. Whereas levels of U6 RNA are significantly decreased upon transfection with ≧20 µg of a chimeric gene producing a stable, capped RNA oligonucleotide, no such effects were seen in any of the above RNA species. Relative levels were equally unaffected by the inherent stability of the intracellularly-generated oligonucleotide. Transcription arrests with Actinomycin D demonstrated that the presence of an RNA oligonucleotide did not perceptively alter the >24 hour $t_{1/2}$ of the small nuclear RNA. No increases in GAPDH RNA levels were seen at successive time points 48 hours to 96 hours after transfection as the oligonucleotide-producing gene was becoming increasingly diluted within cells. Expression of the oligonucleotide-producing gene also did not demonstrate any effect on cellular translation as measured by immunoradiometric protein quantitation of a co-transfected exogenous gene for β-HCG. Taken together, these results suggest that neither stable nor unstable intracellularly generated RNA oligonucleotides significantly alter the cellular properties of transcription or translation.

Constitutive production of abundant intracellular RNA oligonucleotides from an exogenous gene source may be expected to utilize a significant quantity of cellular energy and resources. A variety of cellular factors, both general and specific, could, in theory, be overwhelmed by the increased demands brought about by high doses of the oligonucleotide-producing gene. Evidence for saturation by U6ON of factors involved in the 5' capping of U6, with subsequent decrease in RNA stability, is one example of how a cell might be adversely affected by the RNA oligonucleotides. This adverse effect was found to diminish as transfection dose, and thus intracellular U6ON levels, were decreased, in Example 15 above.

To extend this investigation of possible cellular toxicity to include the more general processes of cellular transcription and translation, the expression of four other genes were monitored. Two of these genes, 7SK and U1, have basal promoter structures similar to U6, and thus the oligonucleotide-producing gene. The other two genes, U3 and GAPDH, share relatively few promoter features with U6 and the oligonucleotide-producing gene. The study of the RNA expression from these four genes provided a means for monitoring not only polymerase and transcription factor availability, but also nuclease and nucleotide saturation.

The structural features of the 7SK promoter has previously been described as nearly identical to those found in U6 (Wasserman DA and Steitz, JA. (1991) Molecular and Cellular Biology 11: 3432–3445; and Murphy S, et al. (1987) Cell 51: 81–87). Both contain a TATA box, a PSE, as well as the upstream DCR. Both are transcribed by RNA polymerase III and terminated by a series of thymine residues. In addition, both receive the unique 5' non-nucleotide γ-monomethyl phosphate cap. More recent studies, however, suggest that despite the high degree of homology in promoter structure and polymerase-specificity, the critical TBP is complexed differently in the two genes and are not mutually exchangeable (Surig, D. et al. (1993) Gene Expression 3: 175–185). Aside from the U6 gene itself, 7SK represents the gene with the greatest degree of promoter similarity and transcriptional requirements to that of the oligonucleotide-producing gene. The function of this RNA gene product is still unknown.

The spliceosomal U1 gene is transcribed by RNA polymerase II, rather than RNA polymerase III, and does not contain a TATA box; however, it does share the same requirement for the PSE and the DCR. Interestingly, the same PBP can activate both promoters, but, as was found for 7SK, the TBP resides in different complexes—TFIIB vs TFIIIB (Bernues J, et al. (1993) EMBO J. 12: 3573–3585). This difference is thought to provide the means for differential polymerase selectivity. Both U1 and 7SK are nuclear (but nonnucleolar), abundant, constitutively expressed, and stable (t½≧24 h) as is U6. In addition, U1 is functionally related to U6 in the formation of an active spliceosome. Thus, the structural and functional similarities of 7SK and U1 to U6 and the oligonucleotide-producing gene make them important genes to monitor for signs of transcriptional dysfunction.

U3 is also a small nuclear RNA gene, but does not function within the mRNA spliceosome, and is confined in location to the nucleolus (Carmo-Fonseca, M., et al. (1991) EMBO J. 10: 195–206). It is believed to play an important role in the splicing of ribosomal RNA. Glyceraldehyde-3-phosphate dehydrogenase (GAPDH) is a translated gene encoding an enzyme within the glycolytic pathway of glucose metabolism. Both of these genes are transcribed by RNA polymerase II and share only few common transcriptional factors with U6 or the oligonucleotide-producing gene. In addition, neither RNA reside primarily in the same subcellular component as U6 or the RNA oligonucleotide. The RNA from these genes allow monitoring of availability of more general transcription factors or substrates, which would lead to RNA downregulation, and nucleases, which would lead to RNA upregulation.

To test for interference with the translational apparatus, a co-transfected, non-native gene was introduced. Monitoring of protein levels from this gene provided unambiguous information about the ability to synthesize a protein from a genomic template. Artifacts based upon differential or extended stabilities of endogenous proteins or mRNA cannot arise with this approach. In addition, the rapid expression of the RNA oligonucleotide upon transfection allowed for an examination of protein induction in the presence of virtually steady-state levels of the RNA oligonucleotide.

Using the above described gene products as potential markers of RNA oligonucleotide-induced cellular toxicity, indications of RNA downregulation, upregulation or altered stability were examined. Neither general nor specific effects of RNA oligonucleotide production on cellular transcription could be detected in any of the above RNA, even at concentrations previously found detrimental to U6. Protein synthesis was similarly unaffected by the expression of the RNA oligonucleotides (stable oligonucleotides or unstable oligonucleotides). These findings suggest that, upon initial investigation, only U6, the gene most closely related to the oligonucleotide-producing gene, was adversely affected by RNA oligonucleotide expression. Other more distantly related cellular RNA appear to retain normal levels of expression and degradation in the presence of RNA oligonucleotide expression, and the protein synthesis pathway appears to function normally.

Materials and Methods

See the Examples above for details on construction of the chimeric genes, cells and cell culture, electroporation, transcription arrest, RNA isolation and polyacrylamide gel Northern blotting. The following Materials and Methods are relevant to this Example.

Agarose gel Northern blotting

A 1% agarose gel was prepared in 1× 3-(n-morpholino) propanesulfuric acid (MOPS) with formaldehyde and diethylpyrocarbonate (DEPC) treated water. Total cellular RNA was prepared for electrophoresis with the addition of 1× MOPS, 13.2% formaldehyde, 36.8% formamide, and 5% bromophenol blue/xylene cyanol loading buffer. Samples were heated for 10 min at 65° C. followed by the addition of 0.045 µg/ml ethidium bromide. The gel was electrophoresed in 1× MOPS at a constant 100 V, washed in DEPC-treated water and photographed. RNA was transferred to Hybond N nylon filters (Amersham, Arlington Heights, Ill.) by passive capillary transfer in 10× standard sodium citrate (SSC) overnight, followed by UV crosslinking for 2 min. Hybridization and washing conditions were as described in Example 6.

Construction of U6mini

The chimeric gene producing an RNA oligonucleotide referred to as U6mini was designed to contain strings of 4 thymines within the oligonucleotide insert region (at base positions 31–34 and 40–43) to terminate the transcript prematurely. The sequence of the upper strand of the inserted duplex fragment was:
5' TCGACTTTTCTCCATTTTAGCTTCCT-TAGCTCCTGATGCA 3'(SEQ ID NO:6)
The digestion, ligation, and sequencing of this gene was as described in the previous chapter, Materials and Methods, "Construction of the chimeric gene."

β-HCG quatitation

Determination of cellular β-HCG was performed 48 hours after MDA453 cell electroporation with 2 µg of the β-HCG gene added to 20 µg of the chimeric oligonucleotide producing gene or promoterless control DNA using the Tandem R total β-HCG immunoradiometric assay (Hybritech, San Diego, Calif.). In this kit, anti-β-HCG antibodies were coupled to plastic beads which are then incubated with the supernatant from transfected cells. A secondary $I^{125}$ radio-labeled anti-β-HCG antibody was then added, and after a 1 hour incubation at 37° C., beads are washed in 0.01% sodium azide and quantitated by a gamma counting.

Results

Figure 19:
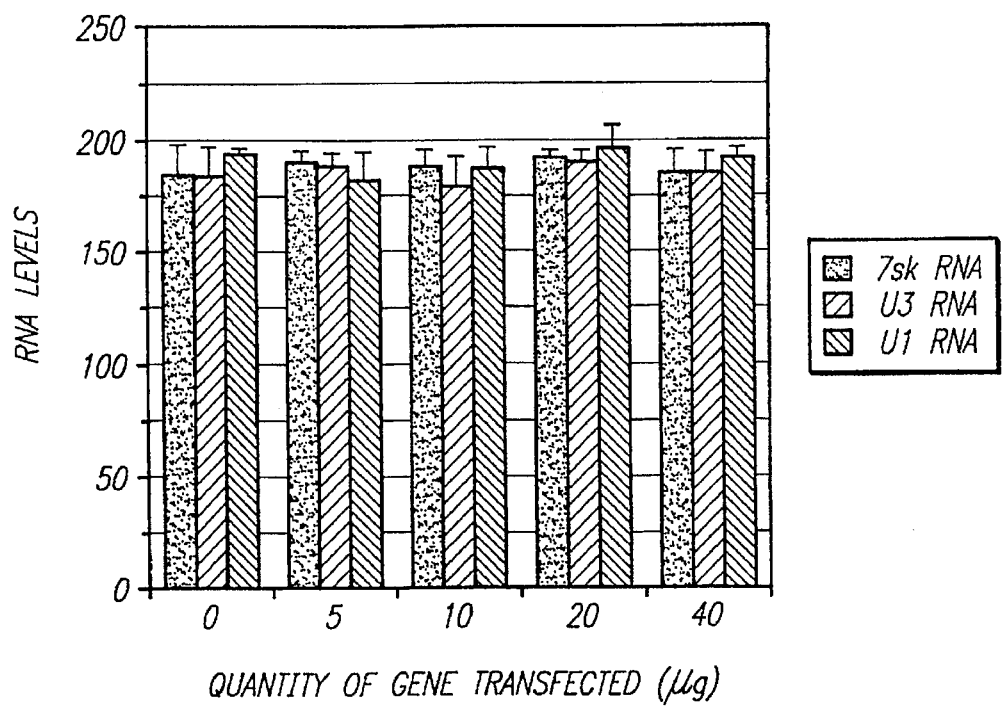
FIG. 19 is a graph demonstrating the dose dependence of U6ON on 7SK, U1, and U3 RNA levels. The nylon filter used to generate FIG. 14A for 293 cells was stripped at 70° C. in prehybridization buffer for 40 minutes followed by reprobing with 7SK, U1 and U3 probes. Quantitative data was obtained by densitometry analysis.

FIG. 19 illustrates the lack of perturbation in 7SK, U1, or U3 RNA levels following transfection with increasing doses (5 to 40 µg DNA/$10^7$ cells) of the chimeric gene for U6ON in 293 cells. This gene has been demonstrated to generate RNA oligonucleotide levels ranging from $5 \times 10^4$ to $5 \times 10^6$ copies/cell and at higher levels was demonstrated to lead to a downregulation of U6 RNA. The absence of any detectable small nuclear RNA downregulation argues strongly that neither polymerases nor TBP or PBP transcription factors were in limiting supply. The absence of detectable RNA upregulation argues analogously that cellular nucleases were not saturated by the presence of additional RNA oligonucleotides.

Figure 20A:
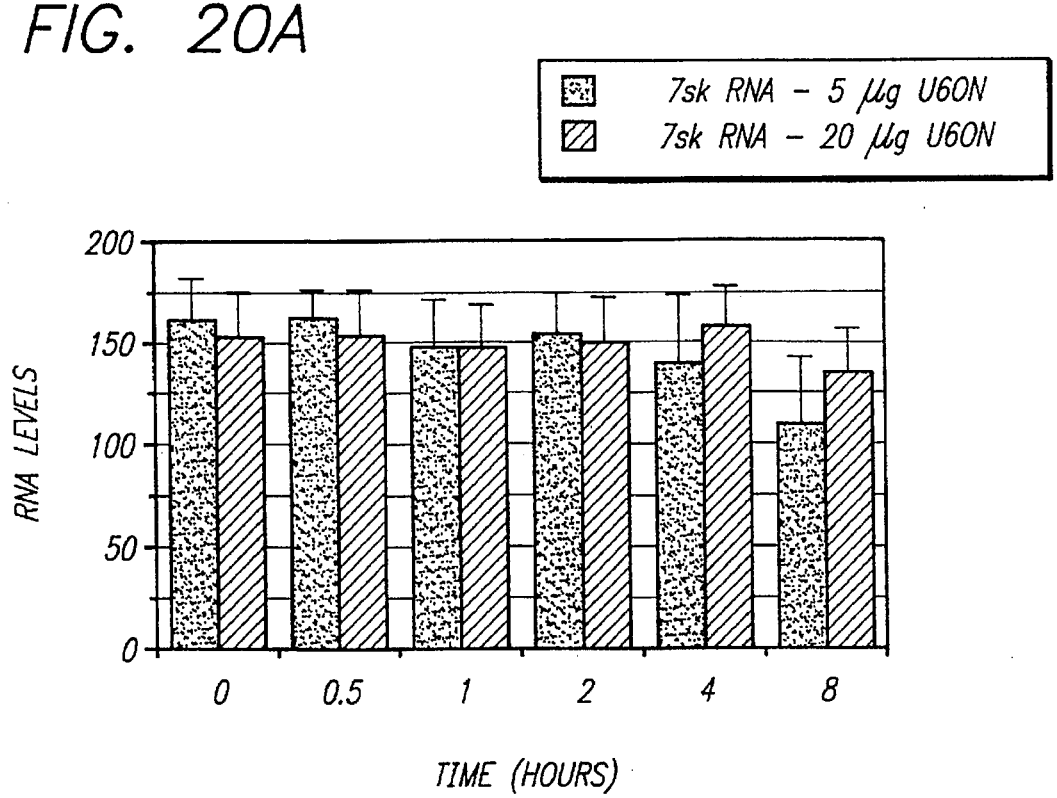
FIG. 20 is a series of three graphs, demonstrating the stabilities of 7SK (FIG. 20A), U1 (FIG. 20B), and U3 (FIG. 20C) RNA in the presence of U6ON. The nylon filters used to generate FIG. 17 for 20 μg and 5 μg gene transfections were stripped and reprobed as described for the previous figure. Quantitative data was obtained by densitometry analysis.
Figure 20B:
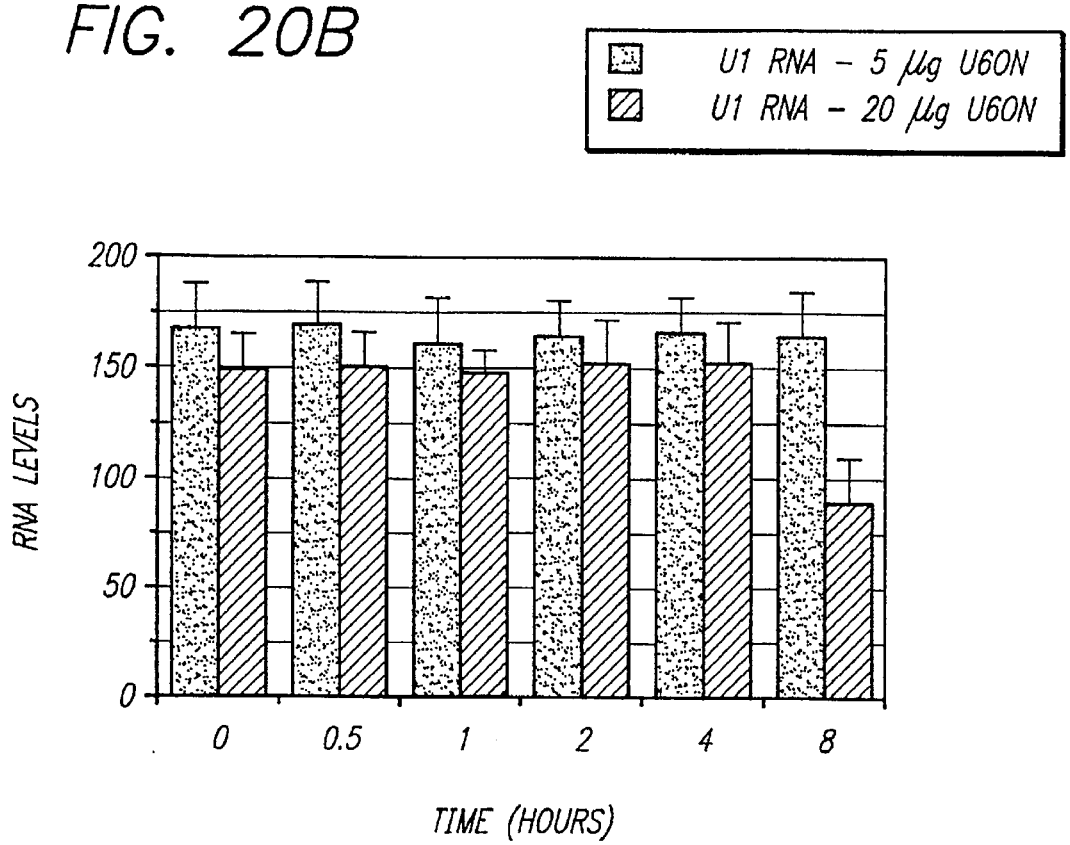
Figure 20C:
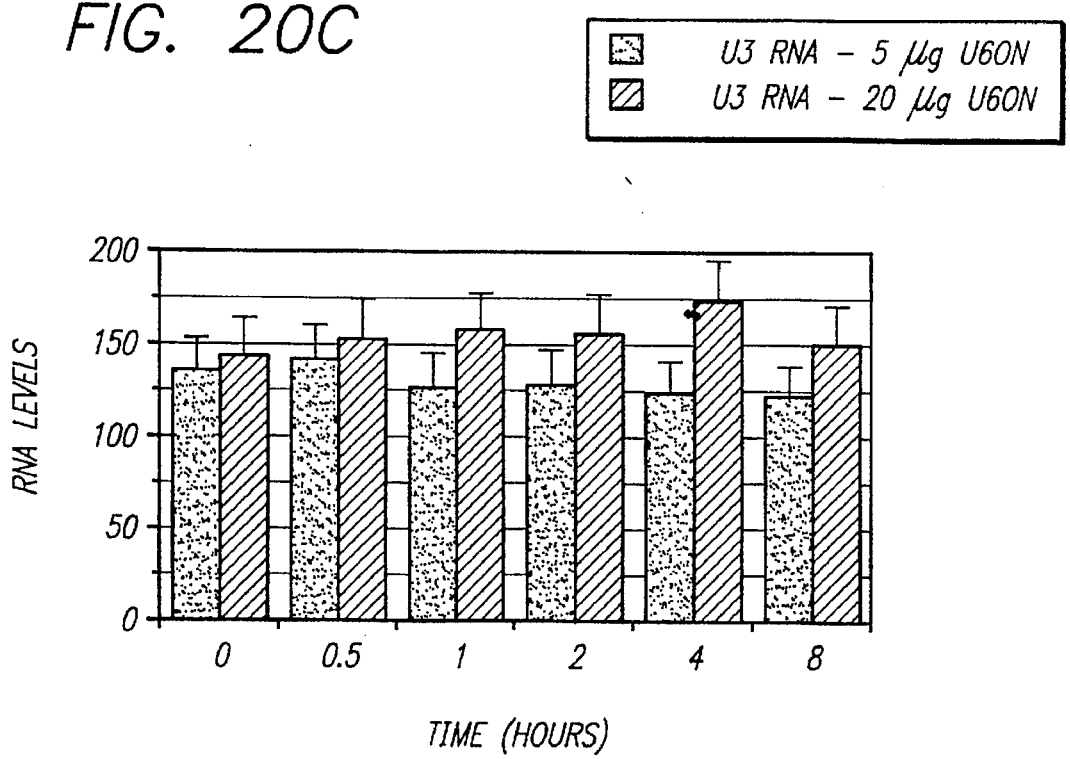

FIG. 20 illustrates a similar lack of perturbation in 7SK, U1, or U3 RNA stability. The nearly constant levels of these small nuclear RNA following transcription arrest 48 hours after electroporation with either 5 µg or 20 µg of the chimeric U6ON-producing gene demonstrated that these RNA retained their normal $\geq 24$ hour $t_{1/2}$. This finding was not surprising for U1 or U3 RNA which obtain a trimethyl guanine 5' cap which has proven to contribute substantially to RNA stability. This cap is structurally distinct from that found on U6 and U6ON, and has been believed to be coupled to the process of transcription (Reddy R. et al. (1992) Pharm Ther. 54: 249–267). However, 7SK RNA is believed to obtain the same 5' γ-monomethyl phosphate cap found on U6 and U6ON. By the same reasoning used to explain U6 downregulation, one might expect that the saturation of the capping apparatus should similarly reduce 7SK stability and therefore overall 7SK levels. However, certain factors could explain this disparity. Most importantly, the increase in RNA stability afforded by the presence of the 5' cap has been shown to be far greater for U6 than for 7SK (>3-fold difference in cap dependence at 8 h) (Shumyatsky G et al. (1993) Nucleic Acids Res 21: 4756–4761). Secondly, the absolute $t_{1/2}$ value has not been adequately determined for 7SK. If it is substantially larger than that of U6, one may need to carry out the transcription arrests for longer than 8 hours to see an effect. Finally the 330 nucleotide length of 7SK may involve more secondary structure or protein binding sites than the 108 nucleotide length of U6, protecting the RNA from more substantial degradation.

Figure 21:
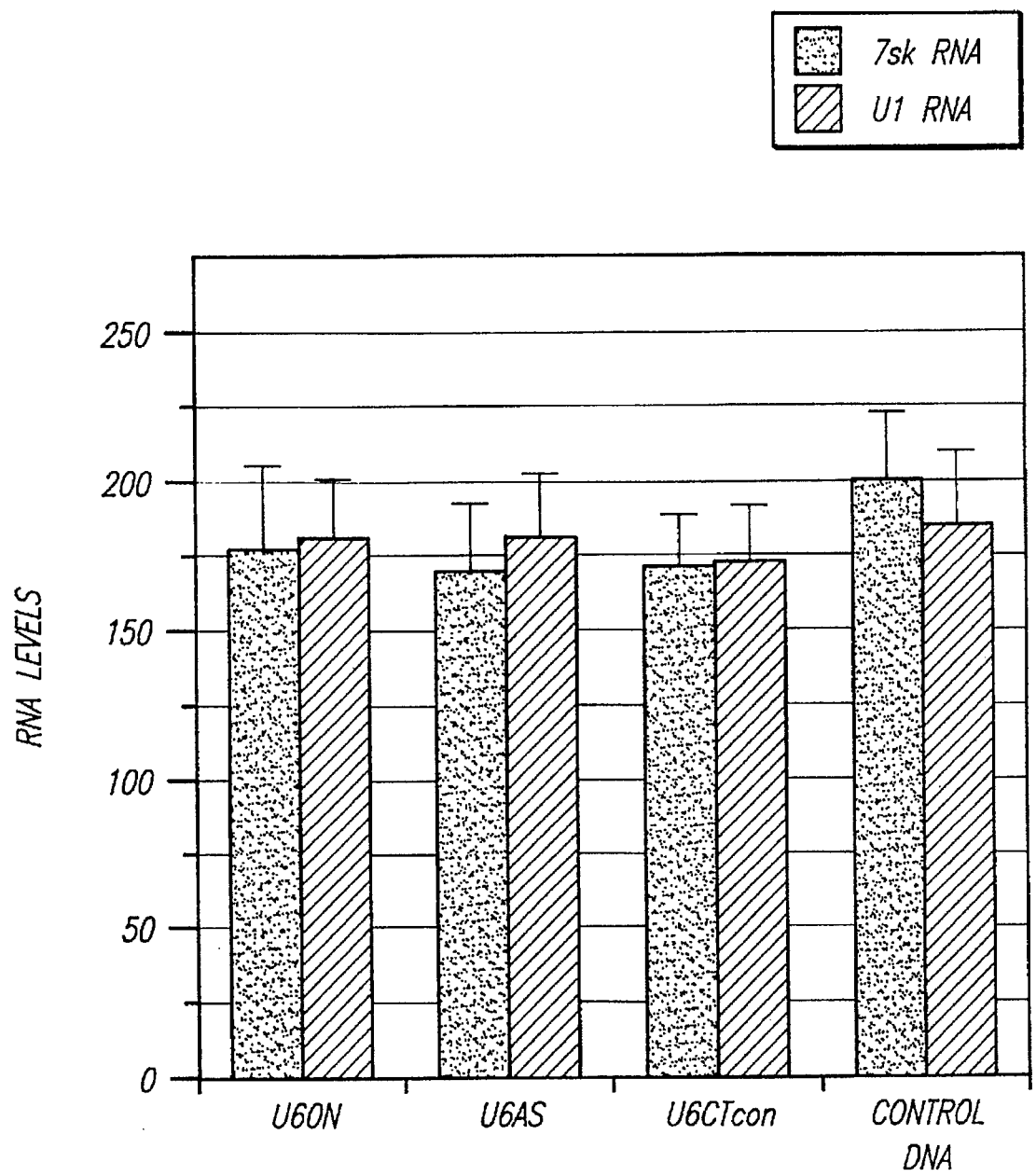
FIG. 21 is a graph demonstrating the effect of RNA oligonucleotide stability on 7SK and U1 RNA levels. 20 μg of the gene for U6ON, U6CTcon, U6AS, or promoterless plasmid control DNA was transfected in MDA453 cells followed by RNA isolation and Northern blotting at 48 hours with 7SK and U1 probes. U6ON and U6CTcon are stable RNA oligonucleotides while U6AS is unstable. Quantitative data was obtained by densitometry analysis.
Figure 22:
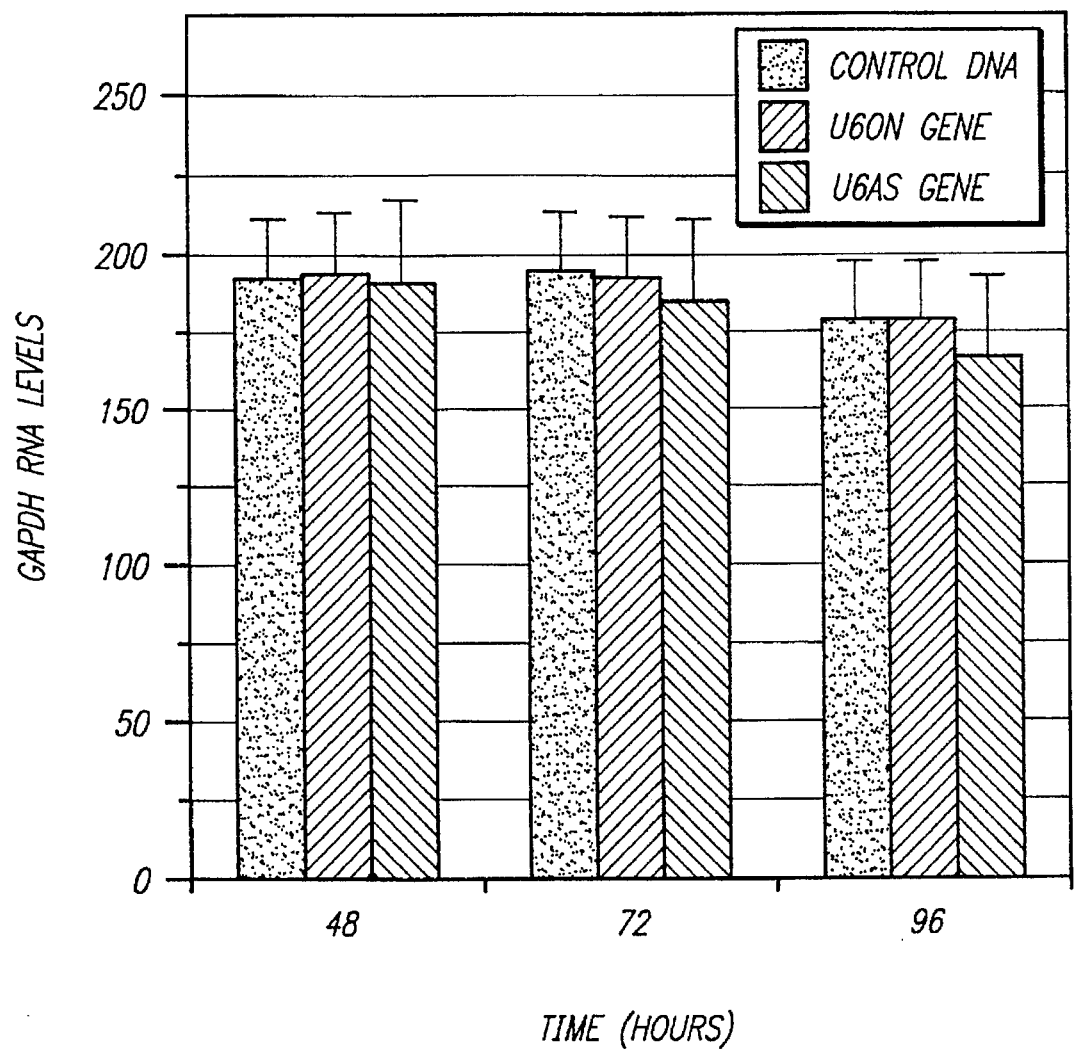
FIG. 22 is a graph demonstrating the effect of U6ON on GAPDH RNA levels. MDA453 cells were transfected with 20 μg of U6ON, U6AS or promoterless plasmid control DNA followed by RNA isolations at 48 hour, 72 hour, and 96 hour time points. Agarose gel Northern blotting (as opposed to polyacrylamide Northern blotting) with a GAPDH probe and densitometry followed.

The absence of an effect on the inherent stability of the generated RNA on 7SK and U1 RNA levels is demonstrated in FIG. 21. In the Examples above U6ON and U6CTcon were both found to be stable and abundant RNA oligonucleotides, whereas U6AS was found to be highly unstable and present at only barely detectable levels. Neither 7SK nor U1 RNA levels were altered perceptively by the different RNA oligonucleotide sequences, stabilities, or overall levels in MDA453 cells. Cellular GAPDH RNA levels were similarly unaffected by a 20 µg transfections of the chimeric gene for U6ON or U6AS monitored 48 to 96 hours post-transfection as seen in FIG. 22.

Figure 23A:
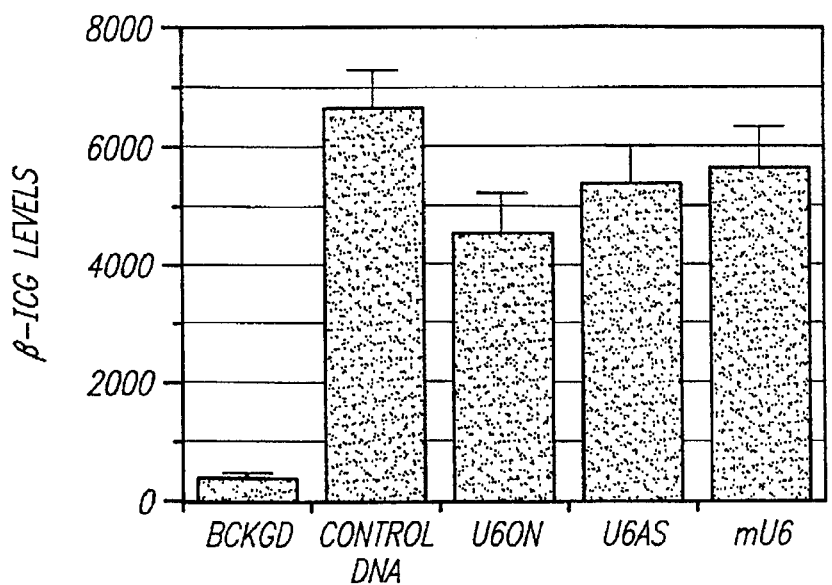
FIG. 23 is a set of two graphs, demonstrating the effect of U6ON on co-transfected β-HCG. MDA453 cells were co-transfected with 20 μg of a chimeric oligonucleotide-producing gene or promoterless plasmid DNA followed by β-HCG quantitation by an immunoradiometric assay described in the Examples below. Two representative experiments are provided to demonstrate the variability in β-HCG expression, but lack of correlation with RNA oligonucleotide presence, levels, lengths, or stabilities.
Figure 23B:
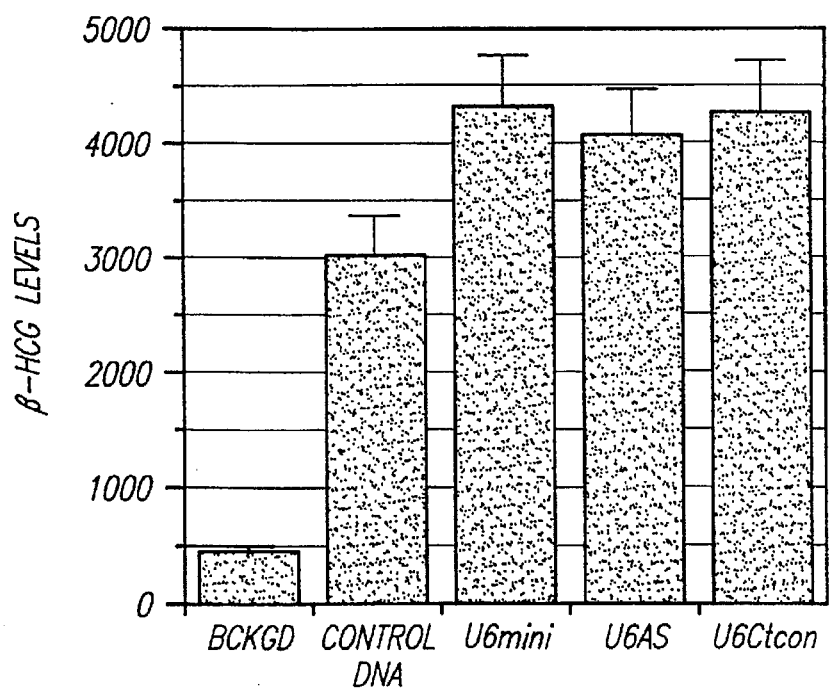

FIG. 23 illustrates two representative examples of β-HCG protein quantitation 48 hours after co-transfection with 20 µg of various chimeric oligonucleotide-producing genes or promoterless control DNA in MDA453 cells. The presence of substantial levels of β-HCG attests to the presence of an intact protein synthesis pathway after transfection with different chimeric genes and subsequent production of RNA oligonucleotides. U6mini refers to construct which terminates at 34 nucleotides. Absolute levels of the protein were highly variable, but did not demonstrate any detectable trend correlating with oligonucleotide levels or oligonucleotide stability. Variations were assumed to result primarily from differences in transfection efficiency, cell survival rate post-electroporation, and experimental error. As expected, β-HCG levels were found to be positively affected by total co-transfected DNA concentrations; however, supplementing DNA concentrations with U6ON or promoterless control DNA gave rise to similar increases in total β-HCG levels (data not shown).

A first analysis of the possible cellular toxicity arising from intracellular production of RNA oligonucleotides in high concentrations was undertaken in Examples 16 and 17.

Upon transient transfections with increasing doses of a variety of chimeric genes, adverse effects were seen only in the U6 gene. This adverse effect took the form of a decrease in U6 stability leading to a decrease in overall U6 RNA levels; however, it was present only after transfection doses of $\geq 20$ µg/$10^7$ cells and only with chimeric genes giving rise to stable RNA oligonucleotides. Lowering the transfection dose relieved both the decrease in stability as well as the decrease in overall U6 RNA levels. Interestingly, even in total cellular RNA samples demonstrating a significant decrease in U6 RNA from normal levels, no longer length non-spliced RNA from either the GAPDH or the human HER2 gene (as described in Example 14) could be detected. Thus, it is possible that lowered U6 levels would not negatively impact the general health of a cell. The finding that U6 is normally in 2–3 fold excess over U4 and U5 (found with U6 in bi-and tri-small nuclear riboprotein complexes) is consistent with this possibility (Sauterer R, et al. (1988) Exptl Cell Research 176:344–359).

The conditions upon which U6 stability was decreased, along with the amount by which it was decreased, suggest strongly that the 5' capping apparatus can be saturated by large amounts of stable RNA oligonucleotides giving rise to a population of uncapped U6 RNA. This suggestion, while not yet definitively proven, leads to in vivo evidence that in U6, capping and transcription are uncoupled. Such evidence is consistent with a previous report demonstrating in vitro evidence of uncoupling (Gupta et al. (1990) J. Biol. Chem. 265: 9491–9495), as well as with a previous report that the activity of a purified capping factor on labeled U6 RNA could be quenched by excess unlabeled U6 RNA (Shimba S. and Reddy R. (1994) J. Biol. Chem. 269:12419–12423).

No other adverse effects of RNA oligonucleotide production could be detected in several other small nuclear RNA with differing transcription factor, polymerase, and capping requirements. U1, U3, and 7SK demonstrated no apparent upregulation or downregulation upon transfection with increasing doses on a variety of chimeric genes. Levels of the "house-keeping" RNA, GAPDH, were similarly unaffected by oligonucleotide production as were protein levels arising from a non-natural co-transfected gene for β-HCG. These results imply that, upon first analysis, transient transfection with subsequent production of high concentrations of an RNA oligonucleotide does not significantly impair the general properties of cellular transcription or translation. Further experimentation with cells stably transfected with the chimeric gene will provide much needed additional information on toxicity.

Example 17

Specificity of Triplex Formation with Intracellularly Generated RNA Oleonucleotides Triplex formation with RNA oligonucleotides and double-stranded DNA provides a means of controlling gene expression from specific promoters and/or creating more selective DNA cleaving agents. The development of a novel technique, Triplex blotting, designed to detect RNA species capable of triplex formation with radiolabeled double-stranded DNA probes within a background of total cellular RNA is described. Triplex blotting offers a new approach for screening potential RNA sequences for triplex formation with double-stranded DNA targets, for comparing relative binding affinities of various triplex-forming RNAs, and for confirming the specificity of triplex formation of a DNA target probe within total cellular RNA. In addition, the technique allows for repeated probing of the same filter while varying critical hybridization conditions such as pH, temperature, or ionic strength.

Interest in oligonucleotides designed to form triple helices on double-stranded DNA has been steadily increasing, primarily due to their potential as artificial repressors of gene expression (Helene, C. (1991) Anticancer Drug Design 6:569–584; Ing, N. H. et al. (1993) Nuc. Acids Res. 21:2789–2796; Maher III, L. J. et al (1989) Science 245:725–730; and Postel, E. H. et al. (1991) Proc. Natl. Acad. Sci. USA 88:8227–8231) and their potential as mediators of site-specific DNA cleavage (Moser, H. E. and Dervan, P. B. (1987) Science 238:645–650; and Strobel, S. A. and Dervan, P. B. (1992) Met. Enzymol. 216:309–321). While the majority of reports cite activity from DNA oligonucleotides, recent reports demonstrate that triplex formation with RNA oligonucleotides may result in a marked increase of free energy of formation over their DNA oligonucleotide counterparts (Roberts, R. W. and Crothers, D. M. (1992) Science 258:1463–1467).

A general technique is described in this Example for the detection of specific RNA molecules capable of triplex formation by a method referred to as Triplex blotting. Similar in nature to standard Northern and Southern blotting techniques, Triplex blotting allows for the detection of a single species of cellular or in vitro generated RNA by triplex formation on radiolabeled double-stranded DNA probes. The benefits of triplex blotting include the sensitive and specific detection of homopurine or homopyrimidine RNA sequences, the rapid screening of duplex DNA target sequences against potential triplex forming RNAs (with direct comparison of relative binding affinities), and the confirmation of specificity of triplex formation amidst a background of total cellular RNA. Moreover, a single blot can be probed multiple times allowing for direct comparison of triplex binding in a variety of hybridization conditions.

Materials and Methods

In vitro generation of triplex RNA

CU-rich RNA was generated in vitro from a pBluescript (Stratagene, La Jolla, Calif.) derivative in which the multi-cloning site was replaced with a 28 base-pair synthetic oligonucleotide duplex. When linearized with SstI and transcribed by T3 RNA polymerase (GIBCO BRL/Life Technologies, Gaithersberg, Md.) the transcript 5' UCC UCU UCC UCC UCC CCC UCC UCC UCCC 3' was generated. When linearized with KpnI and transcribed by T7 RNA polymerase (GIBCO BRL) in the opposite orientation, the corresponding antisense GA-rich strand was generated. Both transcripts also contained approximately 12 nucleotides of flanking RNA derived from cloning and the polymerase start sequences. Control RNA was generated by linearizing pBluescript with EcoR1 in the center of its multicloning site and transcribing with T3 RNA polymerase to give similar full length transcripts. All restriction enzymes were purchased from GIBCO/BRL.

In vivo generation of triplex RNA oligonucleotides

Sequence-specific CU-rich RNA oligonucleotides were generated intracellularly after electroporation with 10 or 20 µg of the chimeric gene producing the RNA oligonucleotide U6ON per $10^7$ cells. Details on the construction of this chimeric gene is found in the Examples above. Control SKBR3 cell populations were electroporated with 20 µg of promoterless plasmid DNA. RNA was isolated 48 hours after transfection by the guanidine isothiocyanate/CsCl method (Glisin, V. R. et al. (1974) Biochem. 13:2633–2643).

Cells and cell culture

Intracellular triplex RNA oligonucleotides were generated in the human breast cell line, SKBR3 (ATCC, Rockville, Md.). These cells were grown in McCoy's medium without Tricine supplemented with 10% fetal calf serum and 100 U/ml of penicillin/streptomycin, and were maintained before and after transfection at 5% $CO_2$. Transfection occurred by electroporation (Biorad, Cambridge, Mass.) using settings as previously described in Example 5.

Radiolabeling the duplex probe

The double-stranded probe for Triplex blotting was generated by annealing a 43-mer oligonucleotide with a short 10-mer primer and extending with a$^{32}$P-labeled dCTP, 0.5 mM dATP, dTTP, and dGTP and Exo Klenow fragment (Stratagene, La Jolla, Calif.) for 25 minutes followed by a 10 minute chase with 0.5 mM cold dCTP. The radiolabel was constrained to the strand unable to form a Watson-Crick duplex with the generated RNA oligonucleotide. The 43 base-pair duplex corresponds to −76 to −34 of the human HER2 promoter within which is a 28 base-pair triplex target (FIG. 24).

Triplex blotting

Triplex blots were obtained by first electrophoretically fractionating in vivo or in vitro generated RNA on 7 M urea, 6% polyacrylamide gels, transferring to nylon Hybond-N filter (Amersham, Arlington Heights, Ill.) by electroblotting in a buffer composed of 17 mM $NaH_2PO_4$/8 mM $Na_2HPO_4$, followed by UV crosslinking for 2 min. Filters were prehybridized for 1 hour at 20° C. in a solution containing 500 mM sodium acetate, 5 mM EDTA brought to pH 5.5 with glacial acetic acid (5× NAE), 5× Denhardt's solution, 1% sodium dodecyl sulfate (SDS), and 20 µg/ml of salmon sperm DNA. Prehybridization was followed by overnight hybridization with 10 pmoles of the radiolabeled probe in the same solution at room temperature with gentle shaking. Filters were subsequently washed twice with shaking in 2× NAE pH 5.5, 0.1% SDS for 20 minutes at room temperature.

FIG. 24 illustrates the double-stranded triplex target within the HER2 proximal promoter and the CU-rich, GA-rich, and control RNA sequences. Note the presence of a single mismatch within the homopurine/homopyrimidine region. CU-rich triplex RNA and DNA oligonucleotides have been shown to bind tightly to double-stranded DNA in a pH-dependent fashion, oriented parallel to the purine strand in the major groove (Felsenfeld, G. et al. (1957) J. Am. Chem. Soc. 79:2023–2024; and Moser, H. E. and Dervan, P. B. (1987) Science 238:645–650). GA-rich triplex DNA oligonucleotides have been demonstrated to bind in a $Mg^{++}$dependent fashion, oriented antiparallel to the purine strand in the major groove (Beal, P. A. and Dervan, P. B. (1991) Science 251:1360–1363). Neither GA-rich nor GU-rich triplex RNA oligonucleotides have been documented to form triple helices with double-stranded DNA under any known conditions (Skoog, J. U. and Maher, L. J. (1993) Nuc. Acids Res. 21:2131–2138).

Figure 25:
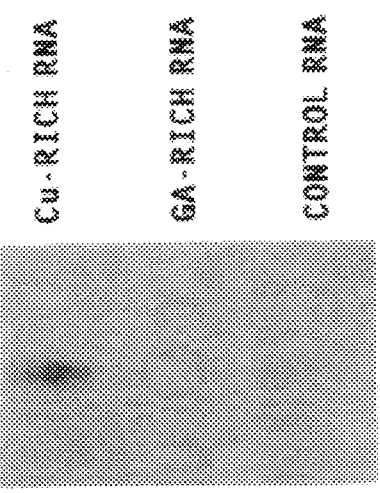
FIG. 25 is a half-tone reproduction of an autoradiogram, demonstrating triplex blotting with in vitro generated RNA. CU-rich, GA-rich, or control RNA strands were generated in vitro by T3 or T7 RNA polymerases from approximately 0.2 pmoles of linearized plasmid. Equal aliquots from these reactions were added to formamide loading buffer, fractionated by electrophoresis and Triplex blotted as described in Example 18.

Given the orientational preferences and the homopurine/pyrimidine nature of the triplex oligonucleotides, both GA-rich and CU-rich triplex RNAs could be generated in vitro from a single plasmid with oppositely directed bacterial promoters. The control RNA was generated by run-off transcription from pBluescript linearized at the center of the multicloning site. After in vitro transcription, RNA samples were electrophoretically fractionated, transferred and crosslinked to a nylon filter, and hybridized with the $^{32}$P-labeled double-stranded DNA probe bearing the triplex target sequence. FIG. 25 demonstrates the sensitive and precise detection of triplex-forming CU-rich RNA by triplex blotting. GA-rich and mixed-sequence control RNA are not detected as they are unable to form triplex structures. Parallel experiments using $^{32}$P-labeled UTP or GTP in the in vitro transcription reaction confirmed that the transcripts' mobility corresponded to those of the triplex RNA oligonucleotides.

This Triplex blotting technique was tested on total cellular RNA samples after triplex RNA transcripts were generated intracellularly through a plasmid bearing the U6 gene with its internal 25–87 nucleotide sequence replaced by the CU-rich triplex-forming RNA sequence shown in FIG. 24. The U6 gene has previously been shown to be transcribed by RNA polymerase III, however it does not contain any intragenic control regions characteristic of other class III genes (Kunkel, G. R. et al. (1987) Proc. Natl. Acad. Sci. USA 83:8575–8579; and Kunkel, G. R. and Pederson, T. (1989) Nuc. Acids Res. 18:7371–7379). Therefore, the internal U6 sequence can be replaced by a triplex-forming (or antisense) sequence and hybrid RNA sequences can be generated intracellularly. The generated triplex RNA oligonucleotide has previously been referred to as U6ON.

Figure 26A:
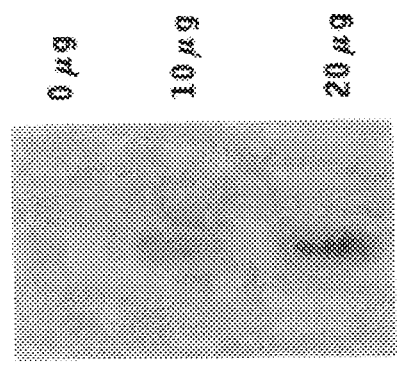
FIG. 26A shows equal amounts of total cellular RNA (11 μg per lane) which were added to formamide loading buffer, fractionated by electrophoresis and Triplex blotted as described in Example 17.

In FIG. 26a, SKBR3 cells were transfected with either 10 or 20 µg (lanes 2 and 3) of the modified U6 triplex-forming RNA generating plasmid, and after 48 hours RNA was isolated, fractionated and blotted as performed with the in vitro generated RNA. Control SKBR3 cell populations were transfected with 20 µg of promoterless plasmid DNA (lane 1). FIG. 26a demonstrates that the double-stranded probe cleanly detects the specific triplex-forming RNA species, U6ON, amidst the background of total cellular RNA. This filter was then stripped in 0.5× NAE, pH 7.5 at 70° C. for 1 hour and reprobed by a standard Northern blot to verify transcript generation and mobility (FIG. 28b).

Figure 26B:
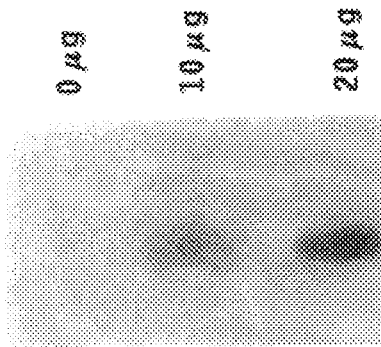
FIG. 26B shows the same filter after stripping at pH 7.5 and reprobing by Northern blot with radiolabeled single-stranded DNA generated by random priming.

To determine optimal binding conditions or to investigate stringency of triplex interactions, ionic strength or pH can be altered in the hybridization buffer. For instance, hybridization and washing at pH 7.5 eliminated virtually all triplex signal from both the in vitro generated RNA filter of FIG. 25 as well as the in vivo generated RNA filter of FIG. 26.

These results clearly demonstrate the feasibility, sensitivity, and specificity of Triplex blotting to detect triplex RNA and establishes this technique as a new tool to aid researchers investigating the potential biological applications of triplex technology.

The results presented in this Example accomplish several major goals. The ability of CU-rich RNA sequences but not GA-rich RNA sequences to form triplexes with a double-stranded homopurine/homopyrimidine DNA target is confirmed. This target sequence (corresponding to a 28 bp region of the HER2/c-erbB2/neu proto-oncogene promoter) and CU-rich triplex RNA are thus justified for use in further investigation of the in vivo effect of an intracellularly generated triplex RNA oligonucleotide.

The technique of Triplex blotting also confirms the specificity of triplex binding to the target sequence. Within a background of total cellular RNA, only the CU-rich in vivo generated RNA is detected by the duplex probe. Thus, probability is reduced that another cellular RNA transcript will interfere by triplex interactions with the target sequence. This technique also offers a means of testing the optimal pH, temperature, and ionic strength conditions for RNA triplex oligonucleotides as has been previously tested for DNA triplex oligonucleotides. The distinct advantage of this new method over those currently in use (such as gel retardation assays and DNase I footprinting) is the ability to repeatedly change hybridization conditions on the same filter instead of needing to repeat the entire experiment with each new set of conditions, thus reducing experimental error. Finally, Triplex blotting offers a means to test not only the specificity of triplex formation, but also the stringency of triplex formation. By creating in vivo generated CU-rich triplex RNA oligonucleotides with various mismatches, the tolerance to these mismatches can be studied in a variety of hybridization conditions.

We claim:

1. A construct for generating a specific oligonucleotide within a cell, which construct comprises a nucleotide sequence from which the transcript is the specific oligonucleotide, said nucleotide sequence being flanked in the 5' direction by a stabilizing region and in the 3' direction by a termination sequence, and a promoter, which initiates transcription by RNA polymerase III, and which promoter is in the 5' direction from the stabilizing region.

2. An oligonucleotide generator, comprising from 5' to 3':
   (a) an U6-type RNA polymerase III promoter;
   (b) a specific nucleotide sequence from which a specific oligonucleotide can be transcribed; and
   (c) a termination sequence; wherein the components of the oligonucleotide generator are operably linked; and wherein the oligonucleotide generator is capable of being transcribed by RNA polymerase III to produce a transcript comprising the specific oligonucleotide.

3. The oligonucleotide generator of claim 2, further comprising:
   a stabilizing region from which a first hairpin-forming sequence can be transcribed; wherein the stabilizing region is operably linked and positioned between the U6-type RNA polymerase III promoter and the specific nucleotide sequence; and wherein the oligonucleotide generator is capable of being transcribed by RNA polymerase III to produce a transcript comprising from 5' to 3' the first hairpin-forming sequence and the specific oligonucleotide.

4. The oligonucleotide generator of claim 3, further comprising a capping segment; wherein the capping segment is operably linked and positioned between the stabilizing region and the specific nucleotide sequence; and wherein the oligonucleotide generator is capable of being transcribed by RNA polymerase III to produce a transcript comprising from 5' to 3' the first hairpin-forming sequence, a capping segment of AUAUCC or AUAUAC, and the specific oligonucleotide.

5. The oligonucleotide generator of claim 4, wherein the first hairpin-forming sequence of the transcript consist of the first 20 nucleotides of the naturally-occurring human U6 transcript.

6. The oligonucleotide generator of claim 4, wherein the capping segment of the RNA transcript is AUAUAC.

7. The oligonucleotide generator of claim 2, wherein the U6-type RNA polymerase III promoter is selected from the group consisting of the U6 promoter, the 7SK promoter, the H1 RNA gene promoter, the plant U3 snRNA gene promoter, the MRP gene promoter, and recombinant promoters thereof, which recombinant promoters are capable of initiating transcription by RNA polymerase III from a position upstream of the transcribed DNA.

8. The oligonucleotide generator of claim 7, wherein the U6-type RNA polymerase III promoter is the human U6 promoter.

9. The oligonucleotide generator of claim 2, wherein the specific oligonucleotide is selected from the group consisting of antisense, triplex-forming, ribozyme oligonucleotides, and combinations thereof.

10. The oligonucleotide generator of claim 9, wherein the specific oligonucleotide is an antisense oligonucleotide.

11. The oligonucleotide generator of claim 9, wherein the specific oligonucleotide is a triplex-forming oligonucleotide.

12. The oligonucleotide generator of claim 9, wherein the specific oligonucleotide is a ribozyme oligonucleotide.

13. The oligonucleotide generator of claim 3, further comprising:

a 3' tail from which a second hairpin-forming sequence can be transcribed;

wherein the 3' tail is operably linked and positioned between the specific nucleotide sequence and the termination sequence; and wherein the oligonucleotide generator is capable of being transcribed by RNA polymerase III to produce a transcript comprising from 5' to 3' the first hairpin-forming sequence, the specific oligonucleotide, and the second hairpin-forming sequence.

14. The oligonucleotide generator of claim 3, further comprising:

a 3' tail from which a lariat-forming sequence can be transcribed;

wherein the 3' tail is operably linked and positioned between the specific nucleotide sequence and the termination sequence;

wherein the oligonucleotide generator is capable of being transcribed by RNA polymerase III to produce a transcript comprising from 5' to 3' the first hairpin-forming sequence, the specific oligonucleotide, and the lariat-forming sequence; and wherein the transcript is predicted to from a stable lariat structure by Watson-Crick base pairing between the nucleotides of the first hairpin-forming region and the lariat-forming region.

15. The oligonucleotide generator of claim 2, further comprising:

a 5' tail from which a first lariat-forming sequence can be transcribed; and a 3' tail from which a second lariat-forming sequence can be transcribed;

wherein the 5' tail is operably linked and positioned between the U6-type RNA polymerase III promoter and the specific nucleotide sequence;

wherein the 3' tail is operably linked and positioned between the specific nucleotide sequence and the termination sequence;

wherein the oligonucleotide generator is capable of being transcribed by RNA polymerase III to produce a transcript comprising from 5' to 3' the first lariat-forming sequence, the specific oligonucleotide, and the second lariat-forming sequence; and wherein the transcript is predicted to from a stable lariat structure by Watson-Crick base pairing between the nucleotides of the first lariat-forming region and the second lariat-forming region.

16. The oligonucleotide generator of claim 4, further comprising two oligonucleotides operably linked and position of either side of the termination sequence such that the first 20 nucleotides downstream of the specific nucleotide sequence on the sense strand is identical to the final 20 nucleotide of the 3' portion of the human U6 gene:

5' GTCCTAGGCTTTTGCACTTTT 3'(SEQ ID NO:8);

wherein the U6-type RNA polymerase III promoter is the U6 promoter; and wherein the first hairpin-forming sequence and the capping segment of the transcript consist of the first 25 nucleotides of the naturally-occurring human U6 transcript.

17. The oligonucleotide generator of claim 16, wherein the sense strand of the specific nucleotide sequence is U6ON:

5' TCGACTCCTCTTCCTCCTCCACCTCCTC-CTCCCATGCA 3'(SEQ ID NO:1).

18. The oligonucleotide generator of claim 2, further comprising a viral vector capable of inducing integration of the oligonucleotide into a chromosome of a target cell.

19. A method for generating oligonucleotides intracellularly, comprising administering an oligonucleotide generator of claim 2, in a form that permits entry of the oligonucleotides into a target cell.

20. A method for continuously generating oligonucleotides intracellularly, comprising administering an oligonucleotide generator of claim 18 in a form that permits entry of the oligonucleotides into a cell.

21. A generator vector, comprising from 5' to 3':

(a) a U6-type promoter;

(b) a stabilizing region from which a hairpin-forming sequence can be transcribed; and (c) a termination sequence; wherein the components of the generator vector are operably linked.

22. The generator vector of claim 21, further comprising from 5' to 3':

a first restriction enzyme site; and a second restriction enzyme site; wherein the first and second restriction enzyme sites are operably linked and positioned between the stabilizing region and the termination sequence.

23. The generator vector of claim 22, further comprising a capping segment selected from the group consisting of ATATCC and ATATAC;

wherein the capping segment is operably linked and positioned between the stabilizing region and the first restriction enzyme site.

24. The generator vector of claim 23, wherein the U6-type promoter is the human U6 promoter; wherein the hairpin-forming sequence of the transcript consist of the first 20 nucleotides of the naturally-occurring human U6 transcript; and wherein the capping segment is ATATCC.

25. The generator vector of claim 24, wherein the first restriction enzyme site is an XhoI site; and wherein the second restriction enzyme site is an NsiI site.

26. The generator vector of claim 24, further comprising two oligonucleotides operably linked and position of either side of the termination sequence such that the first 20 nucleotides downstream of the second restriction enzyme site on the sense strand is identical to the final 20 nucleotide of the 3' portion of the human U6 gene:

5' GTCCTAGGCTTTTGCACTTTT 3'(SEQ ID NO:7).

27. A method of measuring triplex formation, which method comprises:

(a) attaching a single-stranded nucleic acid to a solid support;

(b) contacting the solid support with a fluid comprising a labeled double-stranded probe;

(c) separating the unbound probe from the solid support; and (d) quantifying the amount of labeled double-stranded probe bound to the solid support.

28. A method of measuring triplex blotting, which method comprises:

(a) attaching a double-stranded nucleic acid to a solid support;

(b) contacting the solid support with a fluid comprising a labeled single-stranded probe;

(c) separating the unbound probe from the solid support; and (d) quantifying the amount of labeled single-stranded probe bound to the solid support.

* * * * *

Disclaimer 5,624,803—Sarah B. Noonberg, Berkeley; C. Anthony Hunt, San Francisco, both of Calif. IN VIVO OLIGONUCLEOTIDE GENERATOR, AND METHODS OF TESTING THE BINDING AFFINITY OF TRIPLEX FORMING OLIGONUCLEOTIDES DERIVED THEREFROM. Patent dated April 29, 1997. Disclaimer filed Jun. 3, 2004, by the inventor.

Hereby enters this disclaimer to claims 27 and 28 of said patent.

*(Official Gazette, August 17, 2004)*

(12) EX PARTE REEXAMINATION CERTIFICATE (5604th)
United States Patent
Noonberg et al.

(10) Number: US 5,624,803 C1
(45) Certificate Issued: Nov. 14, 2006

(54) IN VIVO OLIGONUCLEOTIDE GENERATOR, AND METHODS OF TESTING THE BINDING AFFINITY OF TRIPLEX FORMING OLIGONUCLEOTIDES DERIVED THEREFROM

(75) Inventors: Sarah B. Noonberg, Berkeley, CA (US); C. Anthony Hunt, San Francisco, CA (US)

(73) Assignee: The Regents of the University of California, Oakland, CA (US)

Reexamination Request:
No. 90/007,138, Jul. 27, 2004

Reexamination Certificate for:
Patent No.: 5,624,803
Issued: Apr. 29, 1997
Appl. No.: 08/324,001
Filed: Oct. 13, 1994

Related U.S. Application Data

(63) Continuation-in-part of application No. 08/138,666, filed on Oct. 14, 1993, now abandoned.

(51) Int. Cl.
*C12Q 1/68* (2006.01)
*C12P 19/34* (2006.01)
*C12N 15/00* (2006.01)
*C07H 21/02* (2006.01)

(52) U.S. Cl. .............. 435/6; 435/91.1; 435/172.3; 435/320.1; 536/23.1; 536/24.1

(58) Field of Classification Search .............. 435/6, 435/91.1, 320.1; 536/23.1, 24.1
See application file for complete search history.

(56) References Cited

PUBLICATIONS

Waldschmidt, R. et al. (1991). "Identification of transcription factors required for the expression of mammalian U6 genes in vitro" *EMBO J.* 10(9):2595–2603.

*Primary Examiner*—Jeffrey Fredman

(57) ABSTRACT

The present invention encompasses improved methods and materials for the delivering of antisense, triplex, and/or ribozyme oligonucleotides intracellularly, and RNA polymerase III-based constructs termed "oligonucleotide generators" to accomplish the delivery of oligonucleotides. Also encompassed by the present invention are methods for screening oligonucleotide sequences that are candidates for triplex formation.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 27 and 28 were previously disclaimed.

Claims 1–10, 16, 21–23 and 26 are cancelled.

Claims 11–15, 17–19 and 24 are determined to be patentable as amended.

Claims 20 and 25, dependent on an amended claim, are determined to be patentable.

New claims 29–39 are added and determined to be patentable.

11. [The] *An* oligonucleotide generator [of claim 9,] *comprising from 5' to 3':*
   (*a*) *an U6-type RNA polymerase III promoter;*
   (*b*) *a specific nucleotide sequence from which a specific oligonucleotide can be transcribed; wherein the specific oligonucleotide is a triplex-forming oligonucleotide; and*
   (*c*) *a termination sequence;*
   *wherein the components of the oligonucleotide generator are operably linked, and the oligonucleotide generator is capable of being transcribed by RNA polymerase III to produce a transcript comprising the specific oligonucleotide.*

12. [The] *An* oligonucleotide generator [of claim 9,] *comprising from 5' to 3':*
   (*a*) *an U6-type RNA polymerase III promoter;*
   (*b*) *a specific nucleotide sequence from which a specific oligonucleotide can be transcribed, wherein the specific oligonucleotide is a ribozyme oligonucleotide; and*
   (*c*) *a termination sequence;*
   *wherein the components of the oligonucleotide generator are operably linked, and the oligonucleotide generator is capable of being transcribed by RNA polymerase III to produce a transcript comprising the specific oligonucleotide.*

13. [The] *An* oligonucleotide generator [of claim 3, further] *comprising from 5' to 3':*
   (*a*) *an U6-type RNA polymerase III promoter;*
   (*b*) *a specific nucleotide sequence from which a specific oligonucleotide can be transcribed;*
   (*c*) *a termination sequence, wherein (a), (b), and (c) are operably linked;*
   *further comprising*
   (*d*) *a stabilizing region from which a first hairpin-forming sequence can be transcribed, wherein the stabilizing region is operably linked and positioned between the U6-type RNA polymerase III promoter and the specific nucleotide sequence, and*
   (*e*) *a 3' tail from which a second hairpin-forming sequence can be transcribed;*
   *wherein the 3' tail is operably linked and positioned between the specific nucleotide sequence and the termination sequence; and*
   *wherein the oligonucleotide generator is capable of being transcribed by RNA polymerase III to produce a transcript comprising from 5' to 3' the first hairpin-forming sequence, the specific oligonucleotide, and the second hairpin-forming sequence.*

14. [The] *An* oligonucleotide generator [of claim 3, further] *comprising from 5' to 3':*
   (*a*) *an U6-type RNA polymerase III promoter;*
   (*b*) *a specific nucleotide sequence from which a specific oligonucleotide can be transcribed;*
   (*c*) *a termination sequence, wherein (a), (b), and (c) are operably linked;*
   *further comprising*
   (*d*) *a stabilizing region from which a first hairpin-forming sequence can be transcribed, wherein the stabilizing region is operably linked and positioned between the U6-type RNA polymerase III promoter and the specific nucleotide sequence; and*
   (*e*) *a 3' tail from which a lariat-forming sequence can be transcribed;*
   *wherein the 3' tail is operably linked and positioned between the specific nucleotide sequence and the termination sequence;*
   *wherein the oligonucleotide generator is capable of being transcribed by RNA polymerase III to produce a transcript comprising from 5' to 3' the first hairpin-forming sequence, the specific oligonucleotide, and the lariat-forming sequence; and*
   *wherein the transcript is predicted to* [from] *form a stable lariat structure by Watson-Crick base pairing between the nucleotides of the first hairpin-forming region and the lariat-forming region.*

15. [The] *An* oligonucleotide generator [of claim 2, further] *comprising from 5' to 3':*
   (*a*) *an U6-type RNA polymerase III promoter;*
   (*b*) *a specific nucleotide sequence from which a specific oligonucleotide can be transcribed;*
   (*c*) *a termination sequence, wherein (a), (b), and (c) are operably linked;*
   *further comprising*
   (*d*) *a 5' tail from which a first lariat-forming sequence can be transcribed; and*
   (*e*) *a 3' tail from which a second lariat-forming sequence can be transcribed;*
   *wherein the 5' tail is operably linked and positioned between the U6-type RNA polymerase III promoter and the specific nucleotide sequence;*
   *wherein the 3' tail is operably linked and positioned between the specific nucleotide sequence and the termination sequence;*
   *wherein the oligonucleotide generator is capable of being transcribed by RNA polymerase III to produce a transcript comprising from 5' to 3' the first lariat-forming sequence, the specific oligonucleotide, and the second lariat-forming sequence; and*
   *wherein the transcript is predicted to* [from] *form a stable lariat structure by Watson-Crick base pairing between the* nucleotides of the first lariat-forming region and the second lariat-forming region.

17. [The] An oligonucleotide generator [of claim 16,] comprising from 5' to 3':
(a) an U6-type RNA polymerase III promoter;
(b) a specific nucleotide sequence from which a specific oligonucleotide can be transcribed, wherein the sense strand of the specific nucleotide sequence is U6ON: 5' TCGACTCCTCTTCCTCCTCCACCTCCTC-CTCCCATGCA 3'(SEQ ID NO:1);
(c) a termination sequence, wherein (a), (b), and (c) are operably linked;
further comprising
(d) a stabilizing region from which a first hairpin-forming sequence can be transcribed, wherein the stabilizing region is operably linked and positioned between the U6-type RNA polymerase III promoter and the specific nucleotide sequence;
(e) a capping segment, wherein the capping segment is operably linked and positioned between the stabilizing region and the specific nucleotide sequence and wherein the oligonucleotide generator is capable of being transcribed by RNA polymerase III to produce a transcript comprising from 5' to 3' the first hairpin-forming sequence, a capping segment of AUAUCC or AUAUAC, and the specific oligonucleotide; and
(f) two oligonucleotides operably linked and positioned on either side of the termination sequence such that the first 20 nucleotides downstream of the specific nucleotide sequence on the sense strand is identical to the final 20 nucleotides of the 3' portion of the human U6 gene: 5' GTCCTAGGCTTTTGCACTTTT 3'(SEQ ID NO:8);
wherein the U6-type RNA polymerase III promoter is the U6 promoter, and
wherein the first hairpin-forming sequence and the capping segment of the transcript consist of the first 25 nucleotides of the naturally-occurring human U6 transcript.

18. [The] An oligonucleotide generator [of claim 2, further] comprising from 5' to 3':
(a) an U6-type RNA polymerase III promoter;
(b) a specific nucleotide sequence from which a specific oligonucleotide can be transcribed;
(c) a termination sequence wherein the components of the oligonucleotide generator are operably linked and wherein the oligonucleotide generator is capable of being transcribed by RNA polymerase III to produce a transcript comprising the specific oligonucleotide;
further comprising
(d) a viral vector capable of inducing integration of the oligonucleotide into a chromosome of a target cell.

19. A method for generating oligonucleotides intracellularly, comprising administering an oligonucleotide generator [of claim 2,] in a form that permits entry of the oligonucleotides into a target cell, wherein the oligonucleotide generator comprises from 5' to 3':
(a) an U6-type RNA polymerase III promoter;
(b) a specific nucleotide sequence from which a specific oligonucleotide can be transcribed;
(c) a termination sequence, wherein the components of the oligonucleotide generator are operably linked, and the oligonucleotide generator is capable of being transcribed by RNA polymerase III to produce a transcript comprising the specific oligonucleotide.

24. [The] A generator vector [of claim 23], comprising from 5' to 3':
(a) a U6-type promoter;
(b) a stabilizing region from which a hairpin-forming sequence can be transcribed; and
(c) a termination sequence; wherein the components of the generator vector are operably linked;
(d) a first restriction enzyme site, and a second restriction enzyme site; wherein the first and second restriction enzyme sites are operably linked and positioned between the stabilizing region and the termination sequence; and
(e) a capping segment selected from the group consisting of ATATCC and ATATAC; wherein the capping segment is operably linked and positioned between the stabilizing region and the first restriction enzyme site;
wherein the U6-type promoter is the human U6 promoter; wherein the hairpin-forming sequence of the transcript consist of the first 20 nucleotides of the naturally-occurring human U6 transcript; and wherein the capping segment is ATATCC.

29. A construct for generating a specific oligonucleotide within a cell, which construct comprises a chimeric gene comprising a nucleotide sequence from which the specific oligonucleotide is transcribed, said nucleotide sequence being flanked in the 5' direction by a stabilizing region and in the 3' direction by a termination sequence, and a promoter, which initiates transcription by RNA polymerase III, and which promoter is in the 5' direction from the stabilizing region.

30. A chimeric oligonucleotide generator, comprising from 5' to 3':
(a) an U6-type RNA polymerase III promoter;
(b) a specific nucleotide sequence from which a specific oligonucleotide can be transcribed; and
(c) a termination sequence; wherein the components of the oligonucleotide generator are operably linked; and wherein the oligonucleotide generator is capable of being transcribed by RNA polymerase III to produce a transcript comprising the specific oligonucleotide.

31. The chimeric oligonucleotide generator of claim 30 further comprising:
a stabilizing region from which a first hairpin-forming sequence can be transcribed; wherein the stabilizing region is operably linked and positioned between the U6-type RNA polymerase III promoter and the specific nucleotide sequence; and wherein the oligonucleotide generator is capable of being transcribed by RNA polymerase III to produce a transcript comprising from 5' to 3' the first hairpin-forming sequence and the specific oligonucleotide.

32. The chimeric oligonucleotide generator of claim 31, further comprising:
a capping segment; wherein the capping segment is operably linked and positioned between the stabilizing region and the specific nucleotide sequence; and wherein the oligonucleotide generator is capable of being transcribed by RNA polymerase III to produce a transcript comprising from 5' to 3' the first hairpin-forming sequence, a capping segment of AUAUCC or AUAUAC, and the specific oligonucleotide.

33. The chimeric oligonucleotide generator of claim 32, wherein the first hairpin-forming sequence of the transcript consists of the first 20 nucleotides of the naturally-occurring human U6 transcript.

34. The chimeric oligonucleotide generator of claim 32, wherein the capping segment of the RNA transcript is AUAUAC.

35. The chimeric oligonucleotide generator of claim 30, wherein the U6-type RNA polymerase III promoter is selected from the group consisting of the U6 promoter, the 7SK promoter, the H1 RNA gene promoter, the plant U3 snRNA gene promoter, the MRP gene promoter, and recombinant promoters thereof, which recombinant promoters are capable of initiating transcription by RNA polymerase III from a position upstream of the transcribed DNA.

36. The chimeric oligonucleotide generator of claim 35, wherein the U6-type RNA polymerase III promoter is the human U6 promoter.

37. The chimeric oligonucleotide generator of claim 30, wherein the specific oligonucleotide is selected from the group consisting of antisense, triplex-forming, ribozyme oligonucleotides, and combinations thereof.

38. The chimeric oligonucleotide generator of claim 37, wherein the specific oligonucleotide is an antisense oligonucleotide.

39. The chimeric oligonucleotide generator of claim 38, wherein the antisense oligonucleotide comprises a self complementary sequence.

\* \* \* \* \*

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
TCGACTCCTC TTCCTCCTCC ACCTCCTCCT CCCATGCA                    38
```

( 2 ) INFORMATION FOR SEQ ID NO:2:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
TCGACCTCCC TTCCCTTCCC TTCCCCTTCC TCCATGCA                    38
```

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
TCGACATGAG CATTCATCAG GCGGGCAAGA ATGTGATGCA                  40
```

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
TCGAGCATGG CCCCTGCGCA AGGATGACAC GCAAATGCA                   39
```

( 2 ) INFORMATION FOR SEQ ID NO:5:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
TCGACCGCCC CGCCCTGCCA CTCATCGCAG TACATGCA                    38
```

( 2 ) INFORMATION FOR SEQ ID NO:6:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TCGACTTTTC TCCATTTTAG CTTCCTTAGC TCCTGATGCA                    40

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GTCCTAGGCT TTTGCACTTT T                                        21

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:8:

GTCCTAGGCT TTTGCACTTT T                                        21

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i v ) ANTI-SENSE: YES ( x i ) SEQUENCE DESCRIPTION: SEQ ID NO:9:

AAAAGTCCAA AAGCCTAGGA C                                        21

( 2 ) INFORMATION FOR SEQ ID NO:10:

( i ) SEQUENCE CHARACTERISTICS:
        ( A ) LENGTH: 50 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:10:

ATTCTTATAC TTCCTCAAGC AGCCCTCCTC CTCCACCTCC TCCTTCTCCT         50

( 2 ) INFORMATION FOR SEQ ID NO:11:

( i ) SEQUENCE CHARACTERISTICS:
        ( A ) LENGTH: 50 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:11:

AGGAGAAGGA GGAGGTGGAG GAGGAGGGCT GCTTGAGGAA GTATAAGAAT         50

( 2 ) INFORMATION FOR SEQ ID NO:12:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

UCCUCUUCCU CCUCCCCUC CUCCUCCC                                                    28

( 2 ) INFORMATION FOR SEQ ID NO:13:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

GGGAGGAGGA GGGGGAGGAG GAAGAGGA                                                   28

( 2 ) INFORMATION FOR SEQ ID NO:14:

( i ) SEQUENCE CHARACTERISTICS:
    ( A ) LENGTH: 82 base pairs
    ( B ) TYPE: nucleic acid
    ( C ) STRANDEDNESS: single
    ( D ) TOPOLOGY: both ( x i ) SEQUENCE DESCRIPTION: SEQ ID NO:14:

GUGCUCGCUU CGGCAGCACA UAUCCUCGAC CUCCCUUCCC UUCCCUUCCC CUUCCUCCAU                 60

GCAUGAAGCG UUCCAUAUUU UU                                                         82

( 2 ) INFORMATION FOR SEQ ID NO:15:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: both ( x i ) SEQUENCE DESCRIPTION: SEQ ID NO:15:

GUGCUCGCUU CGGCAGCACA UAUCCUCGAC AUGAGCAUUC AUCAGGCGGG CAAGAAUGUG                 60

AUGCAUGAAG CGUUCCAUAU UUUU                                                       84

( 2 ) INFORMATION FOR SEQ ID NO:16:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

UCCUCUUCCU CCUCCCCUC CUCCUCCC                                                    28

( 2 ) INFORMATION FOR SEQ ID NO:17:

( i ) SEQUENCE CHARACTERISTICS:
    ( A ) LENGTH: 58 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:17:

CCCAATCACA GGAGAAGGAG GAGGTGGAGG AGGAGGGCTG CTTGAGGAAG TATAAGAA                   58

( 2 ) INFORMATION FOR SEQ ID NO:18:

( i ) SEQUENCE CHARACTERISTICS:
    ( A ) LENGTH: 58 base pairs
    ( B ) TYPE: nucleic acid ( C ) STRANDEDNESS: double
( D ) TOPOLOGY: linear ( i v ) ANTI-SENSE: YES ( x i ) SEQUENCE DESCRIPTION: SEQ ID NO:18:

TTCTTATACT TCCTCAAGCA GCCCTCCTCC TCCACCTCCT CCTTCTCCTG TGATTGGG    58

( 2 ) INFORMATION FOR SEQ ID NO:19:

( i ) SEQUENCE CHARACTERISTICS:
        ( A ) LENGTH: 43 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:19:

CAAGCAGCCC TCCTCCTCCA CCTCCTCCTT CTCCTGTGAT TGG    43

( 2 ) INFORMATION FOR SEQ ID NO:20:

( i ) SEQUENCE CHARACTERISTICS:
        ( A ) LENGTH: 43 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:20:

CCAATCACAG GAGAAGGAGG AGGTGGAGGA GGAGGGCTGC TTG    43

( 2 ) INFORMATION FOR SEQ ID NO:21:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

UCCUCUUCCU CCUCCCCCUC CUCCUCCC    28

( 2 ) INFORMATION FOR SEQ ID NO:22:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GGGAGGAGGA GGGGGAGGAG GAAGAGGA    28

( 2 ) INFORMATION FOR SEQ ID NO:23:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GGGCCCCCCC UCGAGGUCGA CGGUAUCG    28

( 2 ) INFORMATION FOR SEQ ID NO:24:

( i ) SEQUENCE CHARACTERISTICS:
        ( A ) LENGTH: 323 base pairs
        ( B ) TYPE: nucleic acid -continued ( C ) STRANDEDNESS: single
( D ) TOPOLOGY: linear ( x i ) SEQUENCE DESCRIPTION: SEQ ID NO:24:

| | | | | | | |
|---|---|---|---|---|---|---|
| TTCCCATGAT | TCCTTCATAT | TTGCATATAC | GATACAAGGC | TGTTAGAGAG | ATAATTAGAA | 60 |
| TTAATTTGAC | TGTAAACACA | AAGATATTAG | TACAAAATAC | GTGACGTAGA | AAGTAATAAT | 120 |
| TTCTTGGGTA | GTTTGCAGTT | TTTAAAATTA | TGTTTTAAAA | TGGACTATCA | TATGCTTACC | 180 |
| GTAACTTGAA | AGTATTTCGA | TTTCTTGGCT | TTATATATCT | TGTGGAAAGG | ACGAAACACC | 240 |
| GTGCTCGCTT | CGGCAGCACA | TATCCTCGAG | CATGGCCCCT | GCGCAAGGAT | GACACGCAAA | 300 |
| TGCATGAAGC | GTTCCATATT | TTT | | | | 323 |

( 2 ) INFORMATION FOR SEQ ID NO:25:

( i ) SEQUENCE CHARACTERISTICS:
( A ) LENGTH: 322 base pairs
( B ) TYPE: nucleic acid
( C ) STRANDEDNESS: single
( D ) TOPOLOGY: linear ( x i ) SEQUENCE DESCRIPTION: SEQ ID NO:25:

| | | | | | | |
|---|---|---|---|---|---|---|
| TTCCCATGAT | TCCTTCATAT | TTGCATATAC | GATACAAGGC | TGTTAGAGAG | ATAATTAGAA | 60 |
| TTAATTTGAC | TGTAAACACA | AAGATATTAG | TACAAAATAC | GTGACGTAGA | AAGTAATAAT | 120 |
| TTCTTGGGTA | GTTTGCAGTT | TTTAAAATTA | TGTTTTAAAA | TGGACTATCA | TATGCTTACC | 180 |
| GTAACTTGAA | AGTATTTCGA | TTTCTTGGCT | TTATATATCT | TGTGGAAAGG | ACGAAACACC | 240 |
| GTGCTCGCTT | CGGCAGCACA | TATCCTCGAC | TCCTCTTCCT | CCTCCACCTC | CTCCTCCCAT | 300 |
| GCATGAAGCG | TTCCATATTT | TT | | | | 322 |